(12) United States Patent
Gibson et al.

(10) Patent No.: US 9,358,019 B2
(45) Date of Patent: Jun. 7, 2016

(54) PATIENT-MATCHED INSTRUMENTS

(75) Inventors: Luke Andrew Gibson, Southaven, MS (US); Aashiish Agnihotri, Memphis, TN (US); Abraham Biglari Salehi, Bartlett, TN (US); Michael Dean Hughes, Cordova, TN (US); David L. Evans, Bartlett, TN (US); Jeffrey A. Sharp, Salt Lake City, UT (US); Thomas S. Wolfe, Collierville, TN (US)

(73) Assignee: Smith & Nephew, Inc., Memphis, TN (US)

( * ) Notice: Subject to any disclaimer, the term of this patent is extended or adjusted under 35 U.S.C. 154(b) by 399 days.

(21) Appl. No.: 13/817,160

(22) PCT Filed: Aug. 23, 2011
(Under 37 CFR 1.47)

(86) PCT No.: PCT/US2011/048857
§ 371 (c)(1),
(2), (4) Date: Sep. 25, 2013

(87) PCT Pub. No.: WO2012/027402
PCT Pub. Date: Mar. 1, 2012

(65) Prior Publication Data
US 2014/0094814 A1    Apr. 3, 2014

Related U.S. Application Data

(60) Provisional application No. 61/402,095, filed on Aug. 23, 2010, provisional application No. 61/393,643, filed on Oct. 15, 2010.

(51) Int. Cl.
*A61B 17/17* (2006.01)
*A61B 17/15* (2006.01)
*A61B 17/00* (2006.01)
*A61B 17/56* (2006.01)
*A61F 2/38* (2006.01)
*A61F 2/30* (2006.01)

(52) U.S. Cl.
CPC ........... *A61B 17/1764* (2013.01); *A61B 17/155* (2013.01); *A61B 17/157* (2013.01); *A61B 17/1767* (2013.01); *A61B 2017/00526* (2013.01); *A61B 2017/568* (2013.01); *A61F 2/38* (2013.01); *A61F 2002/30952* (2013.01)

(58) Field of Classification Search
CPC .. A61B 17/17; A61B 17/1764; A61B 17/155; A61B 2017/568
USPC .......................................... 606/87–89, 86 R
See application file for complete search history.

(56) References Cited

U.S. PATENT DOCUMENTS

| | | | | |
|---|---|---|---|---|
| 7,695,477 B2 * | 4/2010 | Creger et al. | ................. | 606/87 |
| 2008/0281426 A1 * | 11/2008 | Fitz et al. | ................. | 623/17.16 |
| 2009/0088754 A1 * | 4/2009 | Aker et al. | ................. | 606/79 |

* cited by examiner

*Primary Examiner* — Christopher Beccia
(74) *Attorney, Agent, or Firm* — Taft Stettinius & Hollister LLP

(57) ABSTRACT

Patient-matched surgical instruments, and methods for making patient-matched surgical instruments, may include patient-matched surgical instruments having an anatomy facing side with several discrete, physically separate anatomy contacting portions configured to match the anatomy of a particular patient. The anatomy contacting portions may be one or more of non-uniform in distribution, non-uniform in shape or non-uniform in surface area.

22 Claims, 52 Drawing Sheets

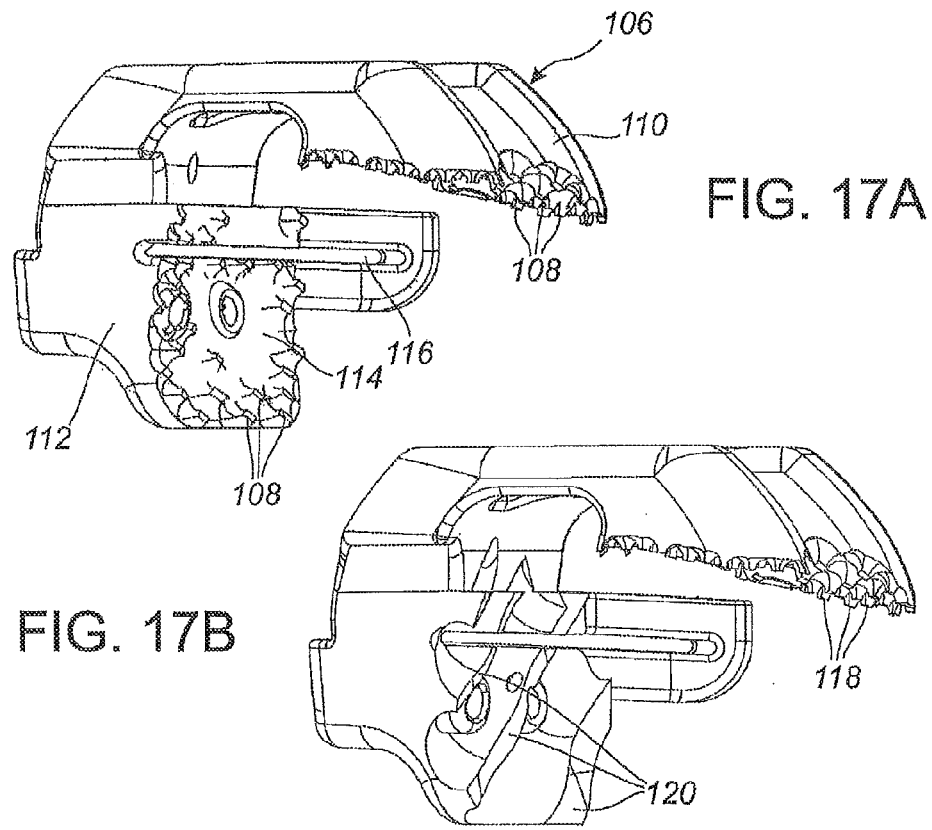
FIG. 17A
FIG. 17B
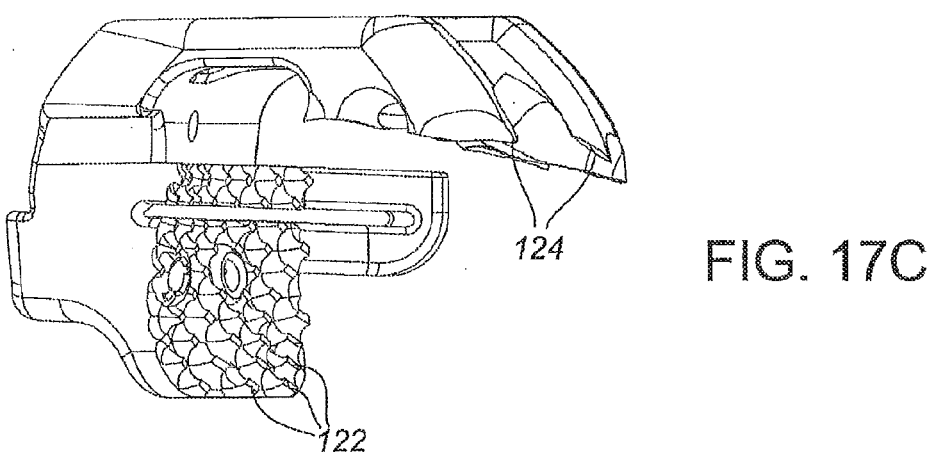
FIG. 17C

PATIENT-MATCHED INSTRUMENTS

RELATED APPLICATIONS

This application is a United States National Phase filing of International Application No. PCT/US11/048857 filed on Aug. 23, 2011 which claims the benefit of U.S. Provisional Application Ser. No. 61/393,643 filed Oct. 15, 2010 for "Patient-Matched Instruments Having Non-Continuous Contact Surfaces, and U.S. Provisional Application Ser. No. 61/402,095 filed Aug. 23, 2010 for "Patient-Matched Instrumentation," the entire contents of each of which are incorporated by reference into this application.

RELATED FIELDS

Surgical instruments and methods for the treatment of bones or joints, in some instances surgical instruments which are matched to a particular patient's anatomy, are described herein. Also described are methods of designing and using such surgical instruments.

BACKGROUND

Conventional patient-matched instruments are provided with large surfaces that are configured to conform to a patient's unique anatomy. Successful surgical outcomes depend on the ability of patient-matched instruments to provide a reproducible, "confident" 3D-fit between the patient-matched instrument and the anatomy that they are designed to rest against. If there is any doubt by an end user that a patient-matched instrument fits well upon repeated engagement with a patient's unique anatomy, or if the instrument appears to fit well with the patient's anatomy in multiple spatial orientations with respect to the anatomy, the instrument is typically discarded, and the surgery is carried out with the use of conventional, non-patient specific instruments.

To date, at least some patient-matched surgical instruments for use in total knee arthroplasty have employed anatomy-contacting surfaces that are substantially "negatives" of distal femoral and proximal tibial articular joint surfaces. The anatomy-contacting surfaces are generally large surface areas that conform in a continuous manner to substantial areas of a patient's anatomy. In some instances, the custom surgical instruments are provided by obtaining 3D image data of the patient's anatomy (e.g., via an MRI scan), segmenting the 3D image data to clearly delineate surfaces of the bony and/or cartilegeneous anatomy from surrounding tissues, converting the segmented data to a computer model via CAD or other software, performing one or more optional secondary processes (e.g., smoothing functions), using a computer model to customize one or more surfaces of an instrument to the patient's anatomy, and manufacturing the custom instrument such that it is adapted to conform to the patient's anatomy in a single spatial orientation.

In at least some current practices, substantially all portions of the joint anatomy shown in each 3D image data slice are segmented and conventional patient-matched instruments are provided with anatomy-contacting portions that contact substantially continuous areas of the patient's anatomy. Such anatomy-contacting portions have large continuous surface areas of contact with the patient's bone and cartilage, and therefore, it is critical that the engineers or automated programs creating the patient-matched instruments maintain a high level of accuracy and precision throughout each step of the entire segmentation process. Even if only one or two points on anatomy-contacting surfaces of a patient-matched instrument are inaccurate, misaligned, or otherwise misrepresent the true unique anatomy of the patient, the patient-matched instrument may not fit well, sit proud, teeter, wobble, or may not fit at all. In such instances, an end user is less likely to use the instrument. In many cases, poor patient-matched instrument fit may be attributed to even a few minor errors in the segmentation process.

Another drawback to using at least some conventional patient matched instruments is that smooth anatomy-contacting surfaces potentially allow the instruments to slide or slip when engaged with the patient's unique anatomy. For example, in some instances, body fluids in combination with slippery bone and cartilage may work against frictional forces between the instruments and anatomical portions. Moreover, due to the highly-conforming nature of conventional patient-matched instruments, improper seating may be exhibited when used with anatomy having an abundance of osteophytes, legions, or tumors. Lastly, soft tissue (e.g., fatty tissues) may gather between patient-matched blocks and bone or cartilage and create a false impression to a user that the instrument is seated properly, when it is in fact, the contrary.

SUMMARY

Embodiments of the present invention include patient-matched instruments, such as cutting guides used in knee arthroplasty procedures, which include one or more anatomy contacting portions that are customized from patient-specific imaging or other types of patient-specific data to match the anatomy of the particular patient, and thus facilitate proper position and orientation of the patient-matched instrument relative to the patient's specific anatomy during a surgical procedure.

In some embodiments, there is provided a patient-matched surgical instrument matched to the anatomy of a particular patient, comprising: an anatomy facing side; wherein the anatomy facing side includes a plurality of discrete, physically separate anatomy contacting portions, the plurality of anatomy contacting portions configured to match the anatomy of the particular patient; wherein the anatomy facing side includes a plurality of discrete, physically separate recessed portions, wherein the plurality of recessed portions are recessed relative to parts of the anatomy contacting portions proximate the plurality of recessed portions; wherein the plurality of anatomy contacting portions are at least one of: non-uniform in distribution; non-uniform in shape; or non-uniform in surface area.

In some embodiments, there is further provided a pliant material located in at least one of the plurality of recessed portions.

In some embodiments, the plurality of anatomy contacting portions defines a first total area of the anatomy facing side and wherein the at least one recessed portion defines a second total area of the anatomy facing side; wherein the second total area is greater than the first total area.

In some embodiments, the patient-matched surgical instrument is a femoral cutting guide, wherein the anatomy facing side includes a patella-femoral groove portion, an intercondylar notch portion, a medial condyle portion, and a lateral condyle portion; wherein the plurality of anatomy contacting portions comprise at least one anatomy contacting portion proximate the patella-femoral groove portion, at least one anatomy contacting portion proximate the intercondylar notch portion, at least one anatomy contacting portion proximate the medial condyle portion, and at least one anatomy contacting portion proximate the lateral condyle portion.

In some embodiments, a total area of the anatomy contacting portions proximate the patella-femoral groove portion and the intercondylar notch portion is greater than a total area of the anatomy contacting portions proximate the medial condyle portion and the lateral condyle portion.

In some embodiments, a total area of the anatomy contacting portions proximate the patella-femoral groove portion and the intercondylar notch portion is less than a total area of the anatomy contacting portions proximate the medial condyle portion and the lateral condyle portion.

In some embodiments, a density of anatomy contacting portions proximate the patella-femoral groove portion and the intercondylar notch portion is greater than a density of anatomy contacting portions proximate the medial condyle portion and the lateral condyle portion.

In some embodiments, the plurality of anatomy contacting portions comprise at least one anatomy contacting portion defining an area contact.

In some embodiments, the plurality of anatomy contacting portions further comprise at least one anatomy contacting portion defining a substantially linear contact.

In some embodiments, the plurality of anatomy contacting portions further comprise at least one anatomy contacting portion defining a substantially point contact.

In some embodiments, the anatomy facing side of the patient matched surgical instrument includes areas of relatively greater contour and areas of relatively lower contour, wherein a concentration of the plurality of anatomy contacting portions is higher in the areas of relatively greater contour than in the areas of relatively lower contour.

In some embodiments, the anatomy facing side of the patient matched surgical instrument includes areas of relatively greater contour and areas of relatively lower contour, wherein a concentration of the plurality of anatomy contacting portions is lower in the areas of relatively greater contour than in the areas of relatively lower contour.

In some embodiments, at least one of the plurality of anatomy contacting portions extends along a periphery of the anatomy facing side.

In some embodiments, the patient-matched surgical instrument is a tibial cutting guide comprising a medial paddle including at least one of the anatomy contacting portions and a lateral paddle including at least one of the anatomy contacting portions.

In some embodiments, there is further provided a guide extending through the patient-matched surgical instrument.

In some embodiments, the guide is a through slot including at least one planar surface.

In some embodiments, there is provided a patient-matched surgical instrument matched to the anatomy of a particular patient, comprising: an anatomy facing side; wherein the anatomy facing side includes a plurality of discrete, physically separate anatomy contacting portions, the plurality of anatomy contacting portions configured to match anatomy of the particular patient; wherein the anatomy facing side includes a plurality of discrete, physically separate recessed portions, wherein the plurality of recessed portions are recessed relative to parts of the anatomy contacting portions proximate the plurality of recessed portions; and wherein the plurality of anatomy contacting portions define a first total area of the anatomy facing side and wherein the plurality of recessed portions define a second total area of the anatomy facing side; wherein the second total area is greater than the first total area.

In some embodiments, the patient-matched surgical instrument is a femoral cutting guide, wherein the anatomy facing side includes a patella femoral groove portion, an intercondylar notch portion, a medial condyle portion, and a lateral condyle portion; wherein the plurality of anatomy contacting portions comprise at least one anatomy contacting portion proximate the patella-femoral groove portion, at least one anatomy contacting portion proximate the intercondylar notch portion, at least one anatomy contacting portion proximate the medial condyle portion, and at least one anatomy contacting portion proximate the lateral condyle portion.

In some embodiments, a total area of the anatomy contacting portions proximate the patella-femoral groove portion and the intercondylar notch portion is greater than a total area of the anatomy contacting portions proximate the medial condyle portion and the lateral condyle portion.

In some embodiments, the anatomy facing side of the patient matched surgical instrument includes areas of relatively greater contour and areas of relatively lower contour, wherein a concentration of the plurality of anatomy contacting portions is lower in the areas of relatively greater contour than in the areas of relatively lower contour.

In some embodiments, the anatomy facing side of the patient matched surgical instrument includes areas of relatively greater contour and areas of relatively lower contour, wherein a concentration of the plurality of anatomy contacting portions is higher in the areas of relatively greater contour than in the areas of relatively lower contour.

In some embodiments, there is provided a patient-matched surgical instrument matched to the anatomy of a particular patient, comprising: an anatomy facing side; wherein the anatomy facing side includes a plurality of discrete, physically separate anatomy contacting portions, the plurality of anatomy contacting portions configured to match the anatomy of the particular patient; wherein the anatomy facing side includes a plurality of discrete, physically separate recessed portions, wherein the plurality of recessed portions are recessed relative to parts of the anatomy contacting portions proximate the plurality of recessed portions; wherein the plurality of anatomy contacting portions are at least one of: non-uniform in distribution; non-uniform in shape; or non-uniform in surface area; and wherein the plurality of anatomy contacting portions define a first total area of the anatomy facing side and wherein the plurality of recessed portions defines a second total area of the anatomy facing side; wherein the second total area is greater than the first total area.

In some embodiments, there is provided a method for making a patient-matched surgical guide matched to the anatomy of a particular patient, comprising: receiving data concerning the anatomy of a particular patient; designing a three-dimensional computer model of the anatomy of the particular patient from the received data; wherein the three-dimensional computer model includes at least one contact portion; positioning a mesh relative to the three-dimensional computer model to define at least one non anatomy contacting portion; designing the patient-matched surgical guide to match the at least one contact portion and to include a recess avoiding the at least one non-anatomy contacting portion; and manufacturing the designed patient-matched surgical guide.

In some embodiments, positioning the mesh relative to the three-dimensional computer model comprises positioning the mesh on the three-dimensional computer model.

In some embodiments, designing the patient-matched surgical guide comprises intersecting a blank of a surgical guide onto the three-dimensional computer model and the mesh.

In some embodiments, the method for making the patient-matched surgical guide further comprises creating an expanded mesh structure from the mesh positioned relative to the three-dimensional computer model.

In some embodiments, positioning the mesh relative to the three-dimensional computer model comprises positioning a first mesh relative to an anterior portion of a three-dimensional computer model of a distal femur and positioning a second mesh relative to a distal portion of the three-dimensional computer model of the distal femur.

In some embodiments, there is provided a method of designing a surgical instrument matched to a particular anatomic structure, wherein the surgical instrument comprises an anatomy facing side including at least one anatomy contacting portion and at least one recessed portion that is recessed relative to parts of the at least one anatomy contacting portion proximate the at least one recessed portion, the method comprising: accessing a three-dimensional computer model of the anatomic structure, the three-dimensional computer model of the anatomic structure including at least one portion corresponding to the at least one anatomy contacting portion of the surgical instrument; using a computer comprising a processor, modifying the three-dimensional computer model of the anatomic structure to create a modified three-dimensional computer model including at least one portion corresponding to the at least one recessed portion of the surgical instrument; and using the modified three-dimensional computer model of the anatomic structure to modify a computer model of an instrument blank to correspond to the surgical instrument.

In some embodiments, modifying the three-dimensional computer model of the anatomic structure comprises creating a raised portion on the three-dimensional computer model of the anatomic structure.

In some embodiments, modifying the three-dimensional computer model of the anatomic structure comprises positioning a mesh relative to the three dimensional computer model of the anatomic structure.

In some embodiments, there is further provided the step of creating an expanded mesh from the mesh.

In some embodiments, positioning the mesh comprises positioning a first mesh relative to an anterior portion of the three-dimensional computer model of the anatomic structure and positioning a second mesh relative to a distal portion of the three-dimensional computer model of the anatomic structure, wherein the three dimensional computer model is a model of a distal femur.

In some embodiments, positioning the mesh comprises wrapping the mesh around a portion of the three dimensional computer model of the anatomic structure.

In some embodiments, positioning the mesh comprises positioning a mesh having a uniform grid pattern.

In some embodiments, accessing the three-dimensional computer model of the anatomic structure comprises accessing a three-dimensional computer model of an anatomic structure of a particular patient.

In some embodiments, using the modified three-dimensional computer model of the anatomic structure to modify the computer model of the instrument blank comprises merging the computer model of the instrument blank with the modified three-dimensional computer model of the anatomic structure.

In some embodiments, using the modified three-dimensional computer model of the anatomic structure to modify the computer model of the instrument blank further comprises subtracting an intersecting volume of the modified three-dimensional computer model of the anatomic structure from a volume of the computer model of the instrument blank.

In some embodiments, there is further provided the step of manufacturing the surgical instrument.

In some embodiments, there is further provided the step of outputting the modified computer model of the instrument blank to a device configured to manufacture the surgical instrument.

In some embodiments, modifying the computer model of the instrument blank comprises removing portions from a computer model of an oversized instrument blank.

In some embodiments, modifying the computer model of the instrument blank to correspond to the surgical instrument comprises modifying the computer model of the instrument blank to correspond to a surgical instrument comprising a plurality of discrete, physically separate anatomy contacting portions, wherein the plurality of anatomy contacting portions are at least one of: (i) non-uniform in distribution; (ii) non-uniform in shape; or (iii) non-uniform in surface area.

In some embodiments, modifying the computer model of the instrument blank to correspond to the surgical instrument comprises modifying the computer model of the instrument blank to correspond to a surgical instrument wherein the at least one anatomy contacting portion defines a first total area of the anatomy facing side and wherein the at least one recessed portion defines a second total area of the anatomy facing side; wherein the second total area is greater than the first total area.

In some embodiments, there is provided a method of designing a surgical instrument matched to a particular anatomic structure, wherein the surgical instrument comprises an anatomy facing side including at least one anatomy contacting portion and at least one recessed portion that is recessed relative to parts of the at least one anatomy contacting portion proximate the at least one recessed portion, the method comprising: accessing a three-dimensional computer model of the anatomic structure, the three-dimensional computer model of the anatomic structure including at least one portion corresponding to the at least one anatomy contacting portion of the surgical instrument; using a computer comprising a processor, modifying the three-dimensional computer model of the anatomic structure to create a modified three-dimensional computer model including at least one portion corresponding to the at least one recessed portion of the surgical instrument, wherein modifying the three-dimensional computer model of the anatomic structure comprises positioning a mesh relative to the three dimensional computer model of the anatomic structure; and using the modified three-dimensional computer model of the anatomic structure to modify a computer model of an instrument blank to correspond to the surgical instrument.

In some embodiments, positioning the mesh comprises positioning a first mesh relative to an anterior portion of the three-dimensional computer model of the anatomic structure and positioning a second mesh relative to a distal portion of the three-dimensional computer model of the anatomic structure, wherein the three dimensional computer model is a model of a distal femur.

In some embodiments, positioning the mesh comprises wrapping the mesh around a portion of the three dimensional computer model of the anatomic structure.

In some embodiments, positioning the mesh comprises positioning a mesh having a uniform grid pattern.

In some embodiments, there is provided a method of designing a surgical instrument matched to a particular anatomic structure, wherein the surgical instrument comprises an anatomy facing side including at least one anatomy contacting portion and at least one recessed portion that is recessed relative to parts of the at least one anatomy contacting portion proximate the at least one recessed portion, the method comprising: accessing a three-dimensional computer model of the anatomic structure, the three-dimensional computer model of the anatomic structure including at least one portion corresponding to the at least one anatomy contacting portion of the surgical instrument; using a computer comprising a processor, modifying the three-dimensional computer model of the anatomic structure to create a modified three-dimensional computer model including at least one portion corresponding to the at least one recessed portion of the surgical instrument, wherein modifying the three-dimensional computer model of the anatomic structure comprises positioning a mesh relative to the three dimensional computer model of the anatomic structure; using the modified three-dimensional computer model of the anatomic structure to modify a computer model of an instrument blank to correspond to the surgical instrument by: merging the computer model of the instrument blank with the modified three-dimensional computer model of the anatomic structure; and subtracting an intersecting volume of the modified three-dimensional computer model of the anatomic structure from a volume of the computer model of the instrument blank; and outputting the modified computer model of the instrument blank to a device configured to manufacture the surgical instrument.

Further areas of applicability of the inventions and their embodiments described herein will become apparent from the detailed description provided hereinafter. It should be understood that the written description and accompanying drawings in this document, while illustrating particular embodiments of the invention, are intended for purposes of illustration only and are not intended to limit the scope of the inventions.

BRIEF DESCRIPTION OF FIGURES

FIGS. 17A-17C illustrate additional embodiments of patient-matched surgical instruments.

DETAILED DESCRIPTION OF DRAWINGS

Figure 1:
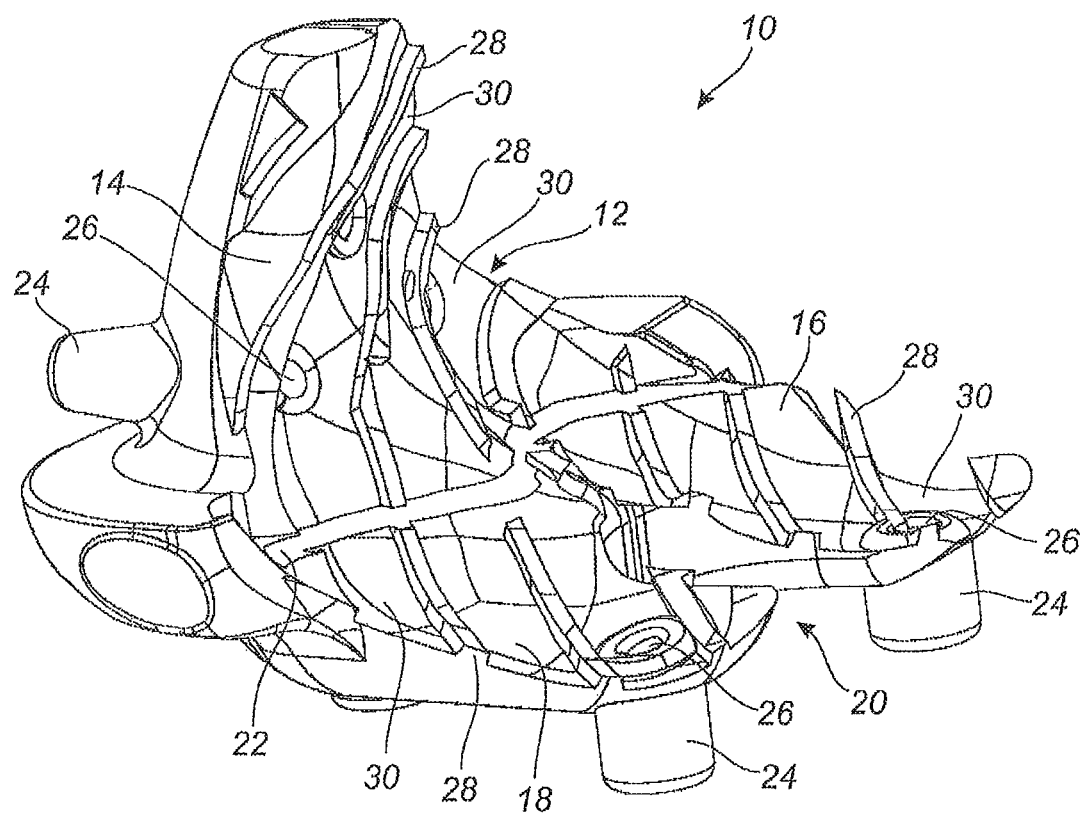
FIGS. 1-8 illustrate an embodiment of a patient-matched surgical instrument in the form of a femoral cutting guide.
Figure 2:
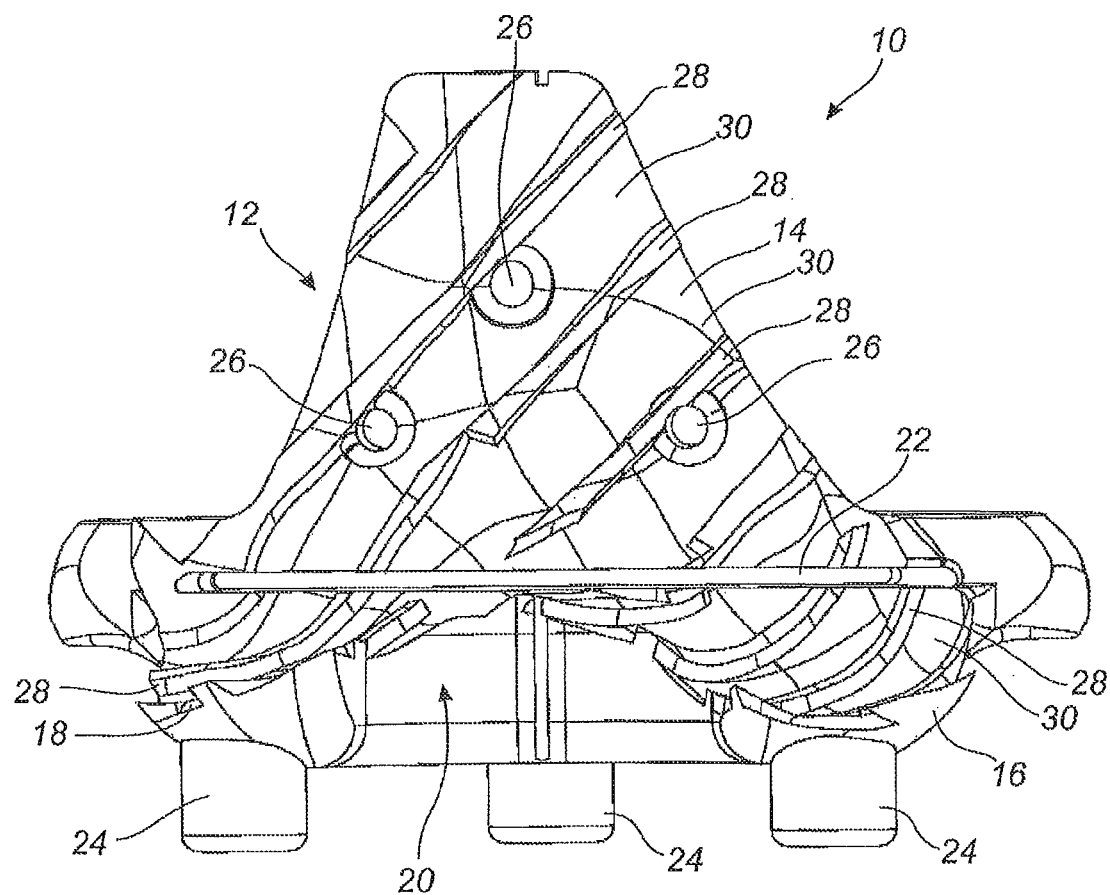
Figure 3:
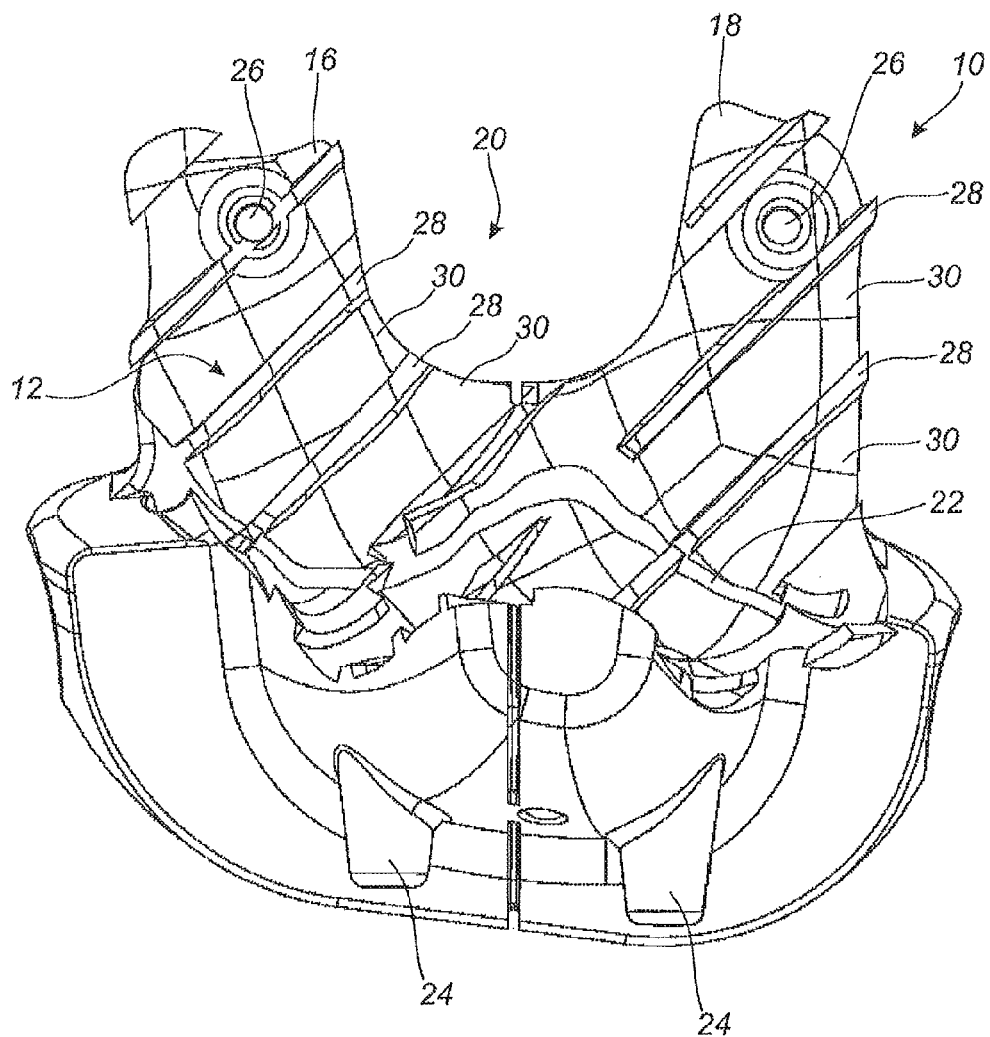
Figure 4:
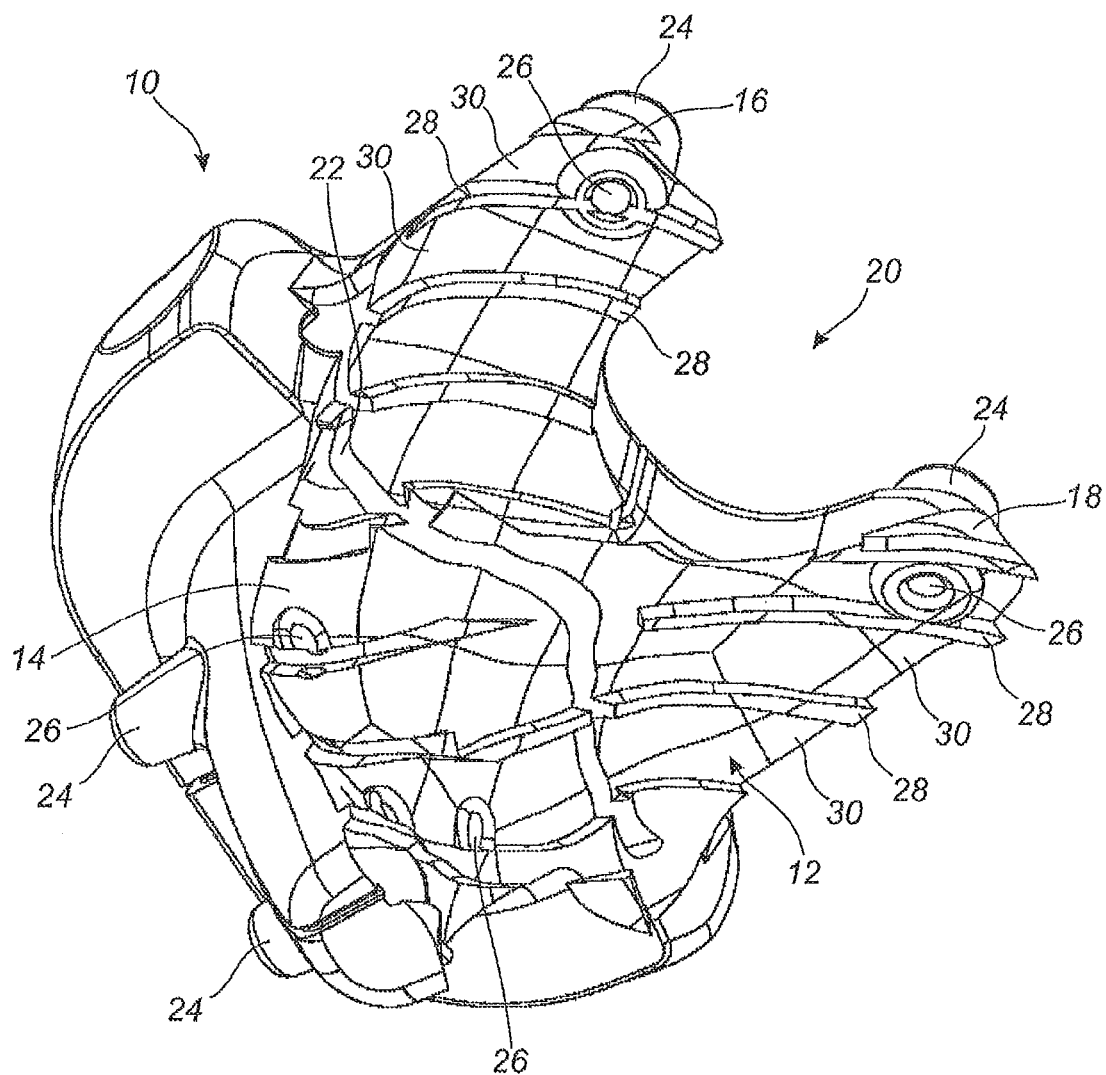
Figure 5:
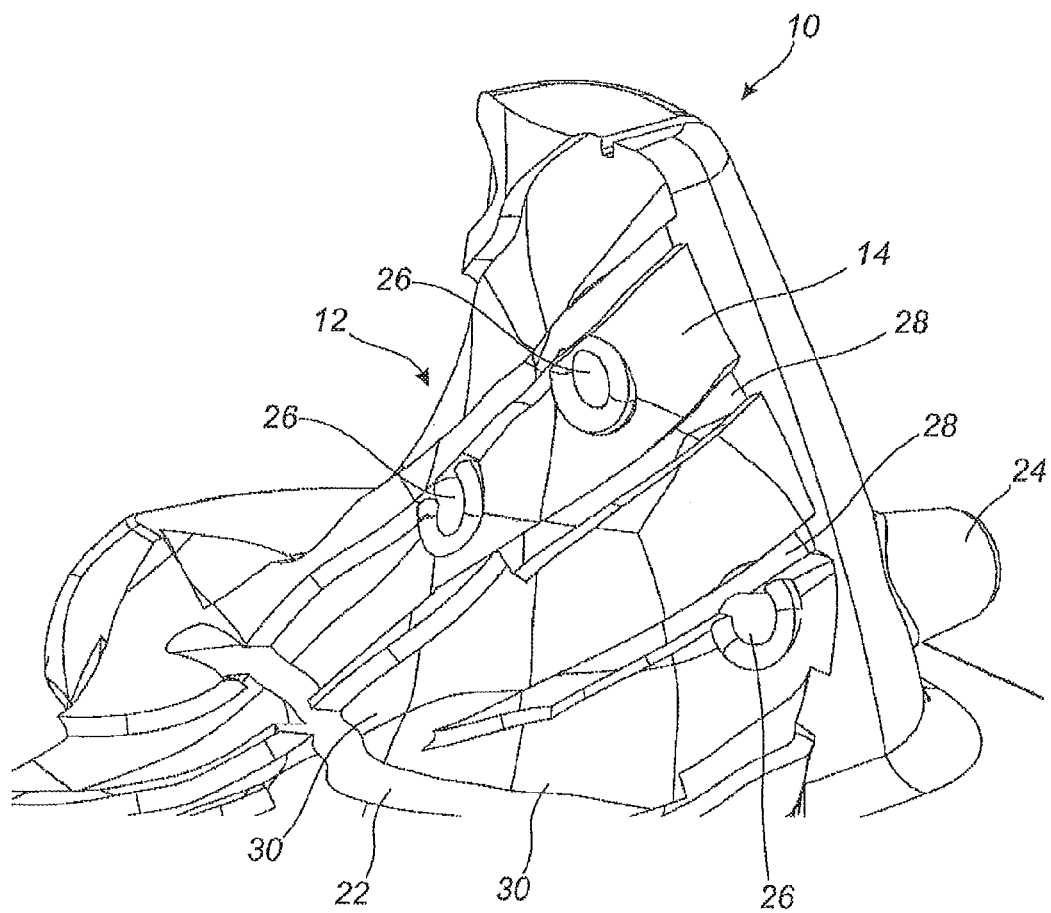
Figure 6:
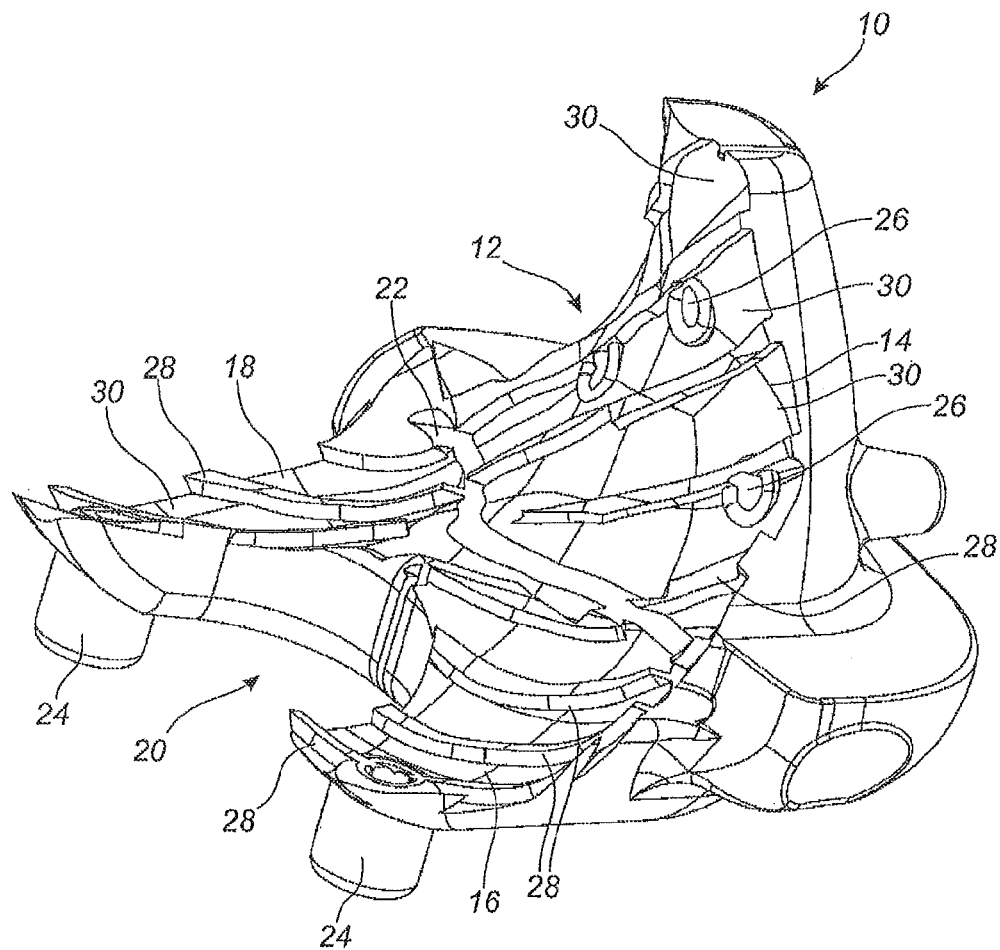
Figure 7:
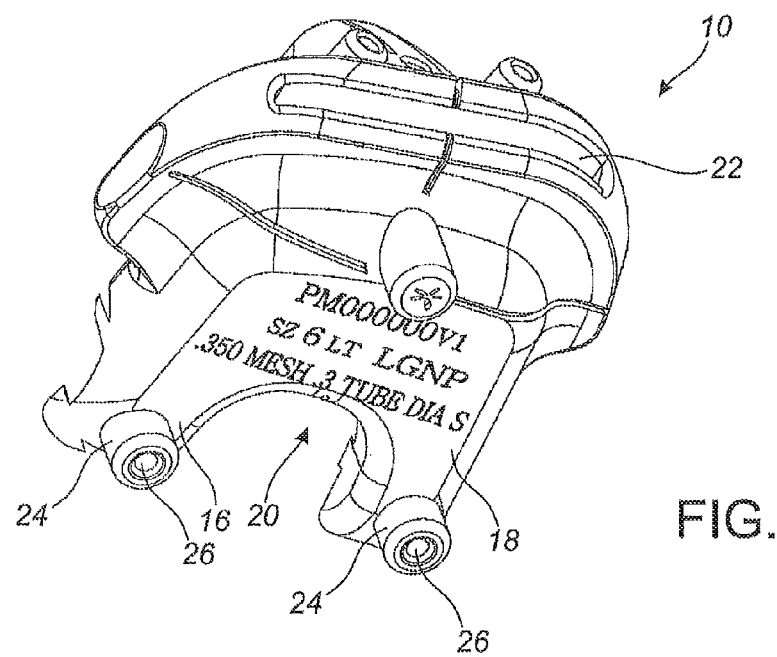
Figure 8:
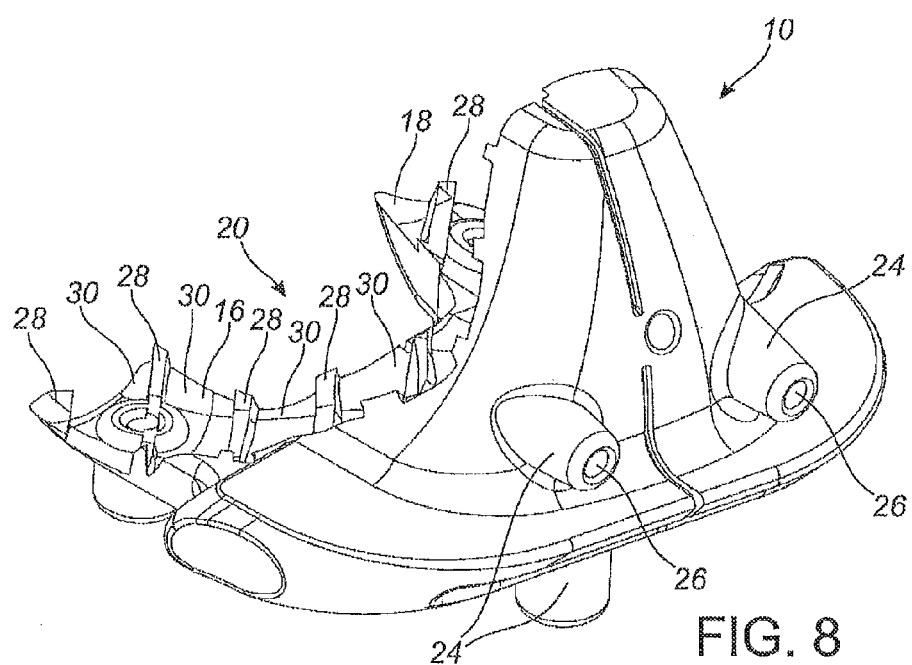

The following description of the drawings is merely exemplary in nature and is in no way intended to limit the invention, its application, or uses.

FIGS. 1-8 illustrate a first embodiment of a patient-matched surgical instrument, which, in this embodiment, is a femoral cutting guide 10. The femoral cutting guide 10 has an anatomy facing side 12 including an anterior portion 14 that is configured to face a patello-femoral groove and anterior cortex region of a distal femur. The instrument further comprises two condylar portions (a medial condyle portion 16 and a lateral condyle portion 18) separated by an intercondylar notch 20, in which the condylar portions are configured to face distal condylar portions of a patient's femur. The patient-matched femoral cutting guide 10 of FIGS. 1-8 also includes a through slot 22 for guiding a cutting instrument such as a saw blade. The cutting guide 10 additionally includes a plurality of bosses 24 having apertures 26 extending therethrough to guide one or more stabilizing fasteners or locating pins, which may or may not be pre-drilled using the apertures. For instance, apertures 26 may be located on the condylar portions and determine a rotation or peg hole location of an implanted femoral prosthetic component. The through slot 22 and apertures 26 are occasionally referred to herein as "guide structures," although that term may also encompass structures other than just apertures and slots. In some embodiments, the guide structures are optional and are not necessarily integrally incorporated into the patient-matched instrument. In some embodiments, guides, bosses, and other structure may be included in non-patient-matched, standardized modular components that are later connected to or otherwise associated with the patient-matched instrument.

Figure 49A:
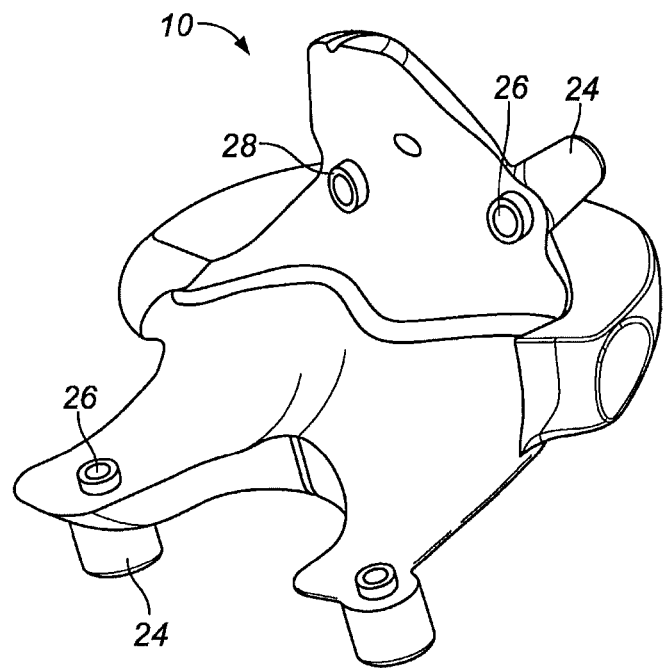
FIG. 49A illustrates an embodiment of a patient-matched instrument with four points of contact.
Figure 49B:
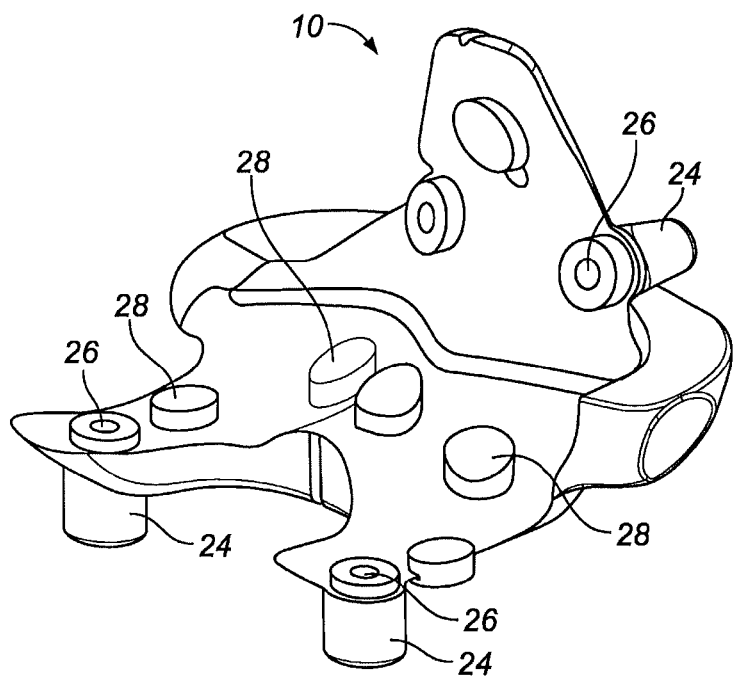
FIG. 49B illustrates an embodiment of a patient-matched instrument with ten points of contact.

The femoral cutting guide of FIGS. 1-8 includes a plurality of discrete, physically separate anatomy contacting portions 28 on the anatomy facing side 12. The anatomy contacting portions 28 are configured to match the anatomy of a particular patient, and, in some embodiments, may be customized to a particular patient based on pre-operatively obtained imaging data of that patient. The number of anatomy contacting portions 28 can vary. FIG. 49A shows a femoral cutting guide with four anatomy contacting portions and FIG. 49B shows a femoral cutting guide with ten anatomy contacting portions.

In other embodiments, the patient-matched surgical instrument and its anatomy contacting portions are matched to a particular patient by using the pre-operatively obtained imaging data of that patient to select a patient-matched surgical instrument from a set of pre-determined instruments. For instance, in one embodiment, the set of pre-determined instruments includes hundreds (e.g. 1200) of pre-determined instruments, such as CAD computer models of instruments, among which automated software or other automated or non-automated functionality may be used to select one instrument from the set that best fits the particular patient, thereby matching the selected surgical instrument to the anatomy of the particular patient.

In the embodiment of FIGS. 1-8, the anatomy contacting portions 28 define substantially linear contacts (in this particular embodiment, splines). Other substantially linear contacts may be utilized additionally or alternatively, including, but not limited to straight line segments, arcuate line segments, or curvilinear segments such as shown in some of the later described embodiments. Other types of anatomy contacting portions are substantial point contacts and area contacts. Non-limiting examples of anatomy contacting portions include teeth, ridges, undulations, serrations, spines, platforms, posts, nodules, tubes, pads, shapes specific to corresponding anatomical features or portions of such anatomical features, and/or various combinations thereof. The anatomy contacting portions may be spaced homogenously and evenly across an anatomy-facing side, or the anatomy contacting portions may be selected and distributed in random, non-random, pre-determined, optimized, or other fashion across the anatomy facing side. In some embodiments, the anatomy-contacting portions may create substantial line contacts with areas of bone and/or cartilage, but, in other embodiments, may contact bone, cartilage, and/or other anatomy in other manners (including point and area contacts). In some embodiments, the locations of the anatomy contacting portions may be determined using a random number generator or similar functionality.

The geometry of portions of the anatomy facing side of the instrument that do not contact bone or cartilage (the "recessed portions") may vary. In the example of FIG. 1, the recessed portions 30 are a series of flutes or channels extending between the anatomy contacting portions 28. These flutes or channels are shown to be generally rectangular or trapezoidal in cross-section, but any cross-section may be used in various embodiments. For example, as shown in FIGS. 9-14, rounded or partially cylindrically shaped flutes or channels 32 may alternatively provide clearance regions where the instrument is not designed to contact the patient's anatomy. In some instances, the recessed portions may be partially or wholly made up of apertures extending through the surgical instrument.

In some embodiments, such as the embodiment shown in FIG. 1, the total area of the recessed portions 30 of the anatomy facing side 12 of the instrument is greater than the total surface area of the anatomy contacting portions 28 of the anatomy facing side 12. In other words, in at least this particular embodiment, the anatomy contacting portions 28 make up only a small portion of the anatomy facing side 12 of the femoral cutting guide 10.

As shown in FIG. 25, in some embodiments, at least some of the recessed portions 34 may be provided with a pliant material 36 that partially or completely fills one or more of the "gaps" between the anatomy contacting portions and the recessed portions.

Returning to the embodiment of FIGS. 1-8, the anatomy contacting portions 28 may extend generally parallel across the anatomy facing side 12 of the femoral cutting guide 10. In other embodiments, however, the anatomy contacting portions are non-parallel and/or are provided at an angle with respect to one another (perpendicular, acute, or obtuse angles). Additionally, the anatomy contacting portions may be discontinuous so as to create dotted line or partial line or curve segment contacts between the instrument and the patient's unique anatomy.

In some embodiments, the anatomy contacting portions may be non-uniform in distribution, non-uniform in shape, and/or non-uniform in contact area. In some embodiments, such non-uniformities may relate to the degree of contour in the particular region of the patient-matched instrument.

Figure 18A:
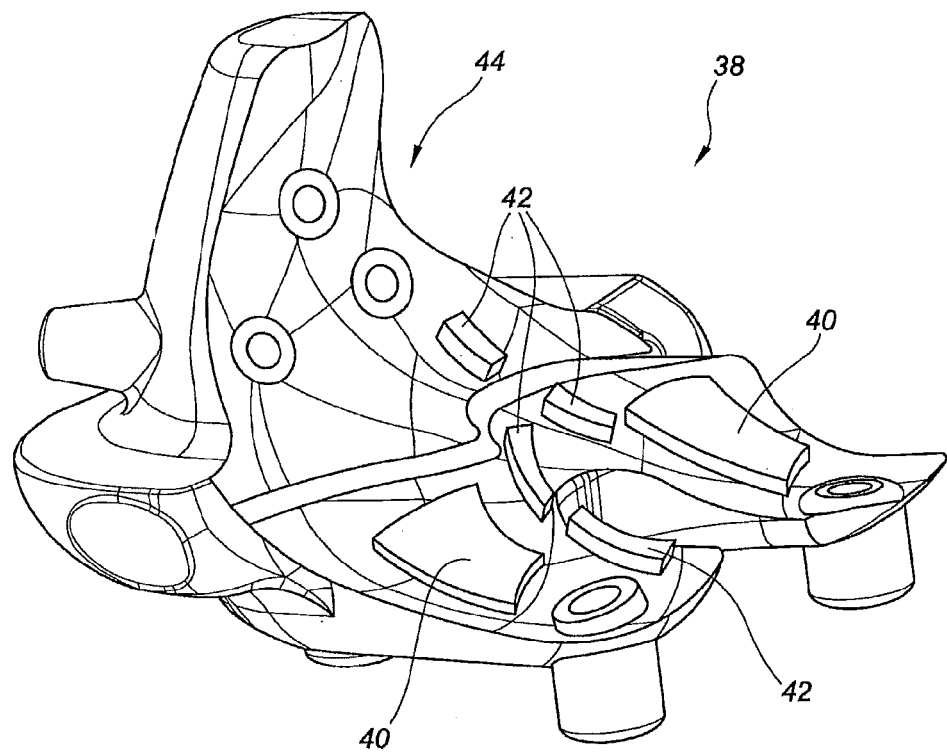
FIGS. 18A-E and 19 illustrate embodiments of a patient-matched surgical instrument in the form of femoral cutting guides, each having anatomy-contacting portions that vary in contact area, shape, and/or distribution.
Figure 18B:
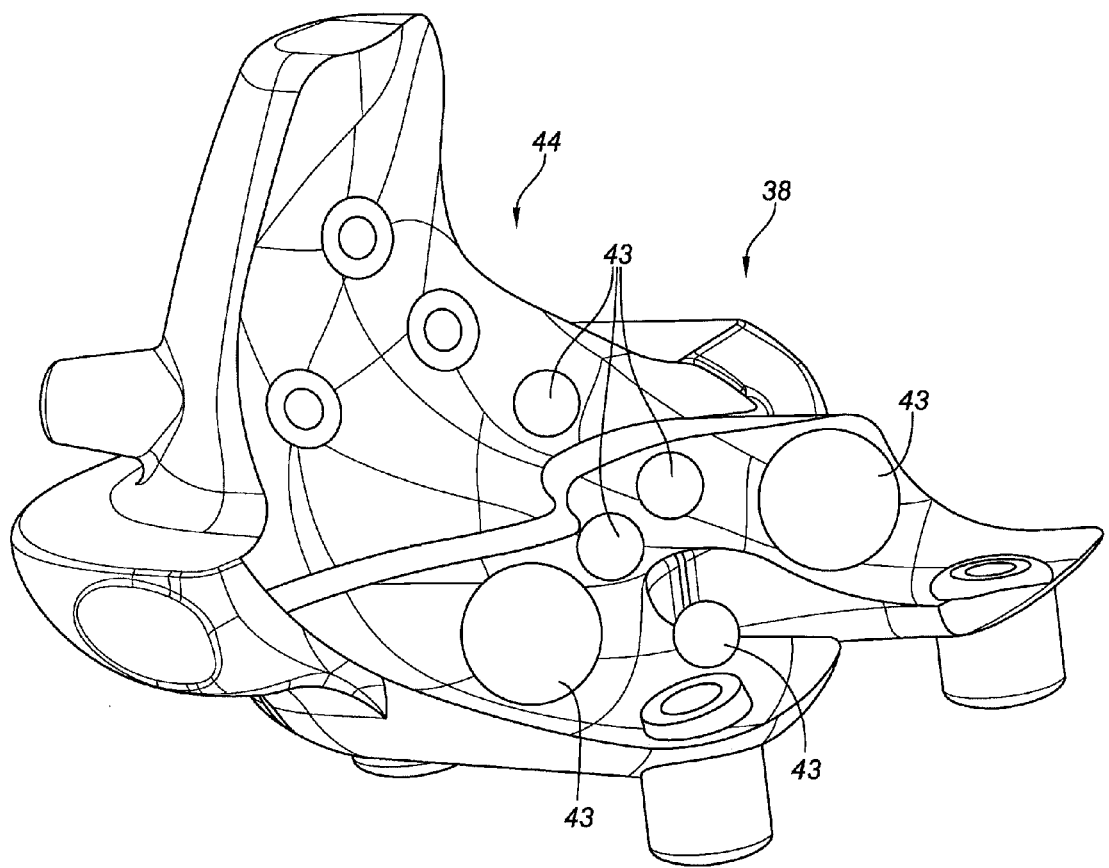
Figure 18C:
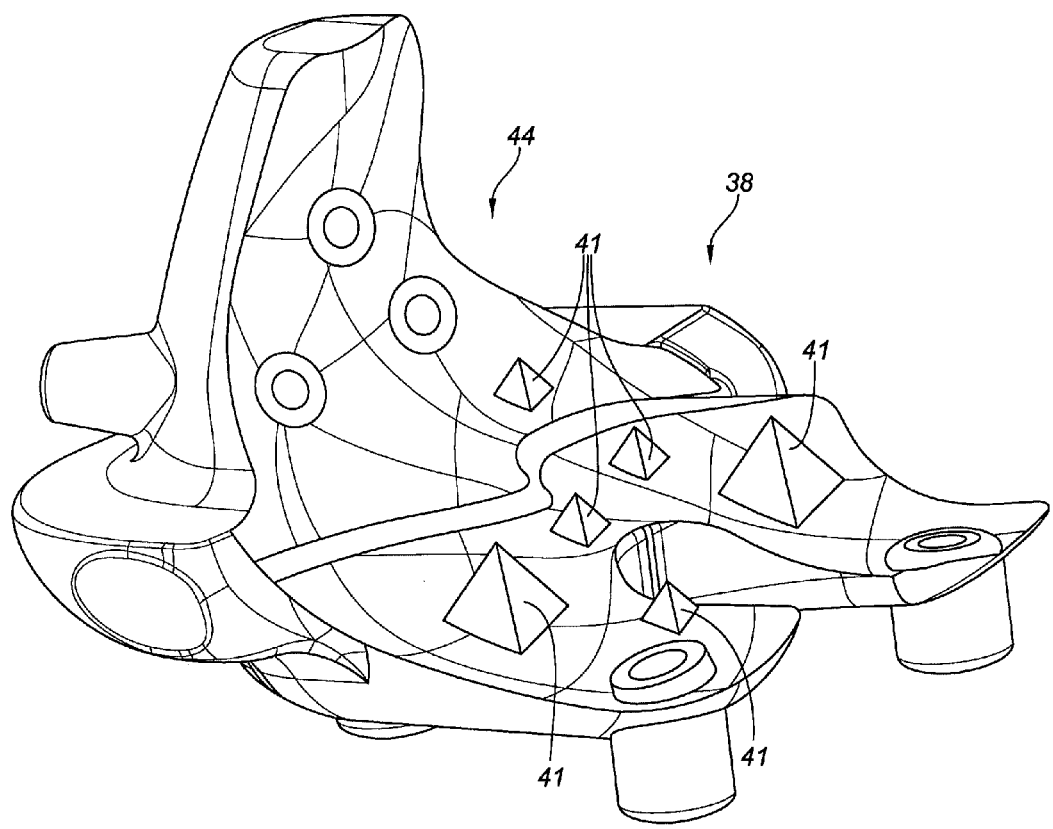
Figure 18D:
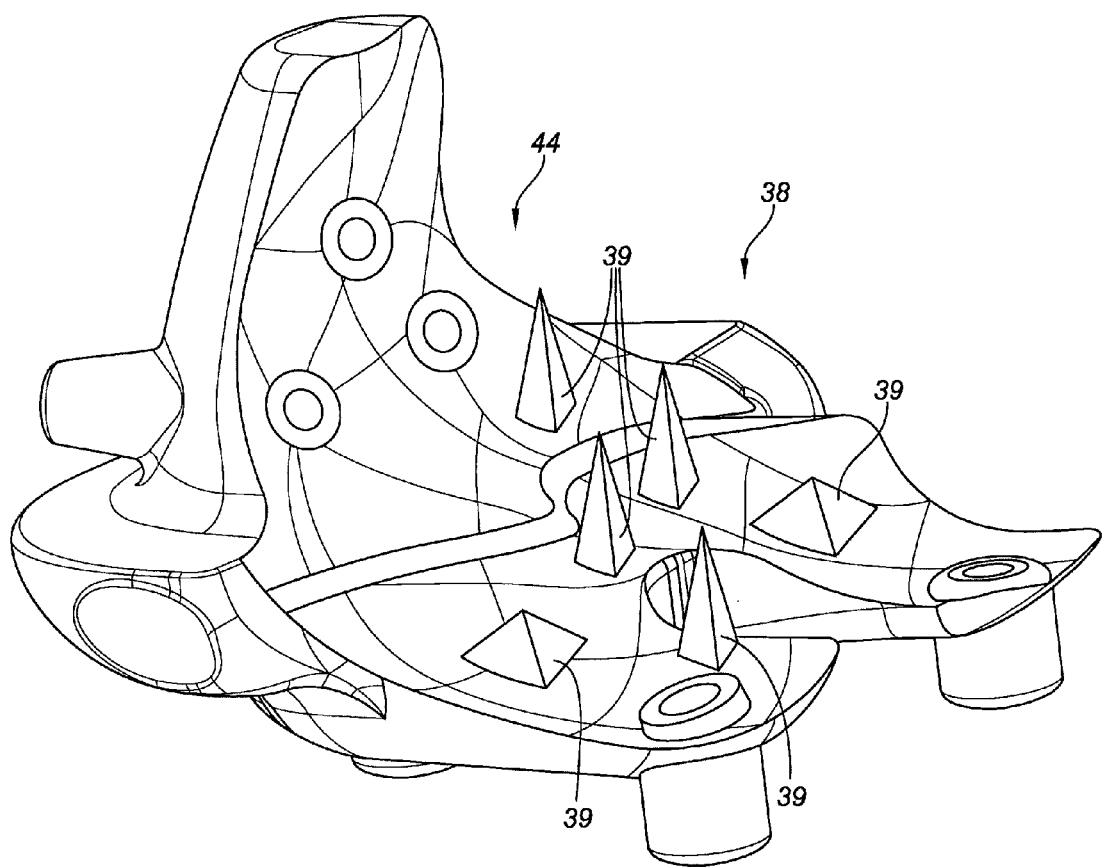

For example, FIG. 18A illustrates a femoral cutting guide 38 that includes anatomy contacting portions that define area contacts 40 (here, substantially rectangular shaped contacts) as well as anatomy contacting portions that define substantially linear contacts 42. In this particular embodiment, in less contoured areas of the anatomy facing side 44, the anatomy contacting portions have a larger contact area than anatomy contacting portions in areas having a greater contour. For example, the area proximate the femoral condyles is generally less contoured than the areas proximate the patella-femoral groove and intercondylar notch. Thus, area contacts 40 generally have a larger area than substantially linear contacts 42, which, in some embodiments, may not be "area" contacts at all and be splines, ridges or other structures that contact the anatomy along a discrete line. In some embodiments, the contacts 43 are spherical and the diameter of the contacting spheres is a function of the topology, as shown in FIG. 18B. Alternatively, the contacting portions 41 can be pyramidal shaped and the pyramid contact point size is a function of topology, as shown in FIG. 18C. In some embodiments, the anatomy contacting portions 39 may also vary in height depending on the contour of the surgical instrument, as shown in FIG. 18D. For example, the femoral condyles stand proud whereas the intercondylar notch is more recessed. Thus, anatomy contacting portions proximate the femoral condyles may be generally shorter than anatomy contacting portions proximate the intercondylar notch. In such embodiments, the substantially linear contact portions are narrow and tall, and thus approximate a discontinuous ridge that is dimensioned to contact a patient's anatomy along the deepest portion of the trochlear groove to provide internal/external rotational stability as well as stabilize the instrument with respect to the patient's femur in a varus/valgus aspect. (In other embodiments, an anatomy contacting portion shaped like a continuous ridge or line segment may be provided in this area.)

Figure 18E:
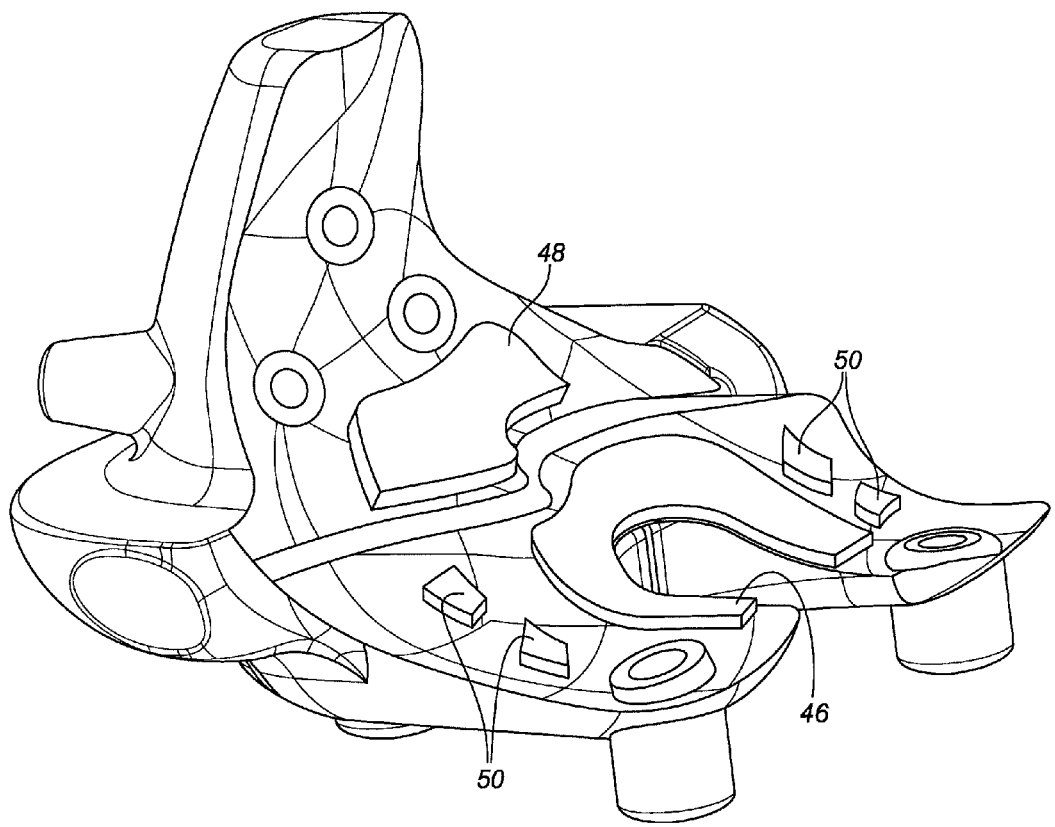

While contrary to the above teachings, it is also envisioned that larger contacting portions may be provided in areas with greater contouring (such as the intercondylar notch or trochlear groove), and smaller contacting portions may be provided in areas with less contouring (such as the femoral condyles). As one example, the embodiment shown in FIG. 18E includes a horseshoe-shaped contacting portion 46 proximate the intercondylar notch, and a large contacting portion 48 proximate the trochlear groove. In contrast, smaller contacting portions 50 are provided proximate the condyles where there is less contouring.

Figure 19:
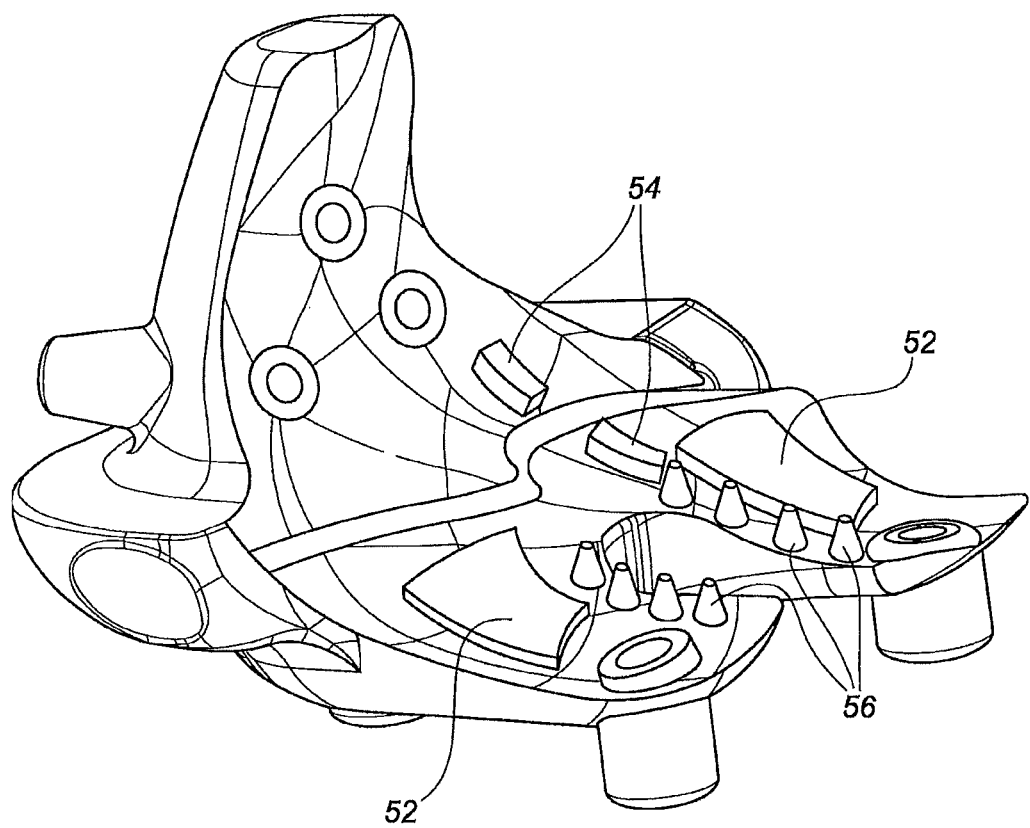

FIG. 19 illustrates another embodiment of a patient-matched surgical instrument that includes anatomy contacting portions that vary in shape depending upon the contour of the instrument. In this embodiment, contacting portions 52 and 54 are generally rectangular (but may vary in size and/or height), whereas contacting portions 56 are generally cone-shaped. The different shaped contacting portions provide for different types of contact between the surgical instrument and a patient's anatomy. For example, rectangular contacting portions 52 provide for increased area contact with the patient's anatomy, narrow contacting portions 54 provide line contact (or substantial line contact) to nest within the trochlear groove, and cone-shaped contacting portions 56 provide for point contact (or substantially point contact) with the patient's anatomy. The shapes of the anatomy contacting portions may be selected to provide for a particular type of contact with particular portions of the patient's anatomy. For example, narrow rectangular and/or wedge-shaped contacting portions (such as contacting portions 54) may be selected for mating with the trochlear groove of the patient's distal femur. In contrast, wider rectangular contacting portions 52 may be selected to provide maximum area contact against the femoral condyles, albeit in a discrete region or regions of the femoral condyles. Cone-shaped contacting portions 56 may be selected when it is desired to reduce the amount of segmentation of image data required by the CAD modeling functionality.

Additionally, FIG. 19 illustrates that the distribution (or density) of the anatomy contacting portions may vary depending on the contour of the instrument. In FIG. 19, a larger number of anatomy contacting portions are concentrated in areas of the instrument having greater contour. Thus, contacting portions 54 and 56 are positioned proximate to the patella-femoral groove and intercondylar notch portions of the instrument (areas having greater contour), whereas contacting portions 52 are provided proximate to the femoral condyle portions (an area having relatively less contour). There are only two contacting portions 52, whereas there are more than two contacting portions 54 and 56.

Figure 20:
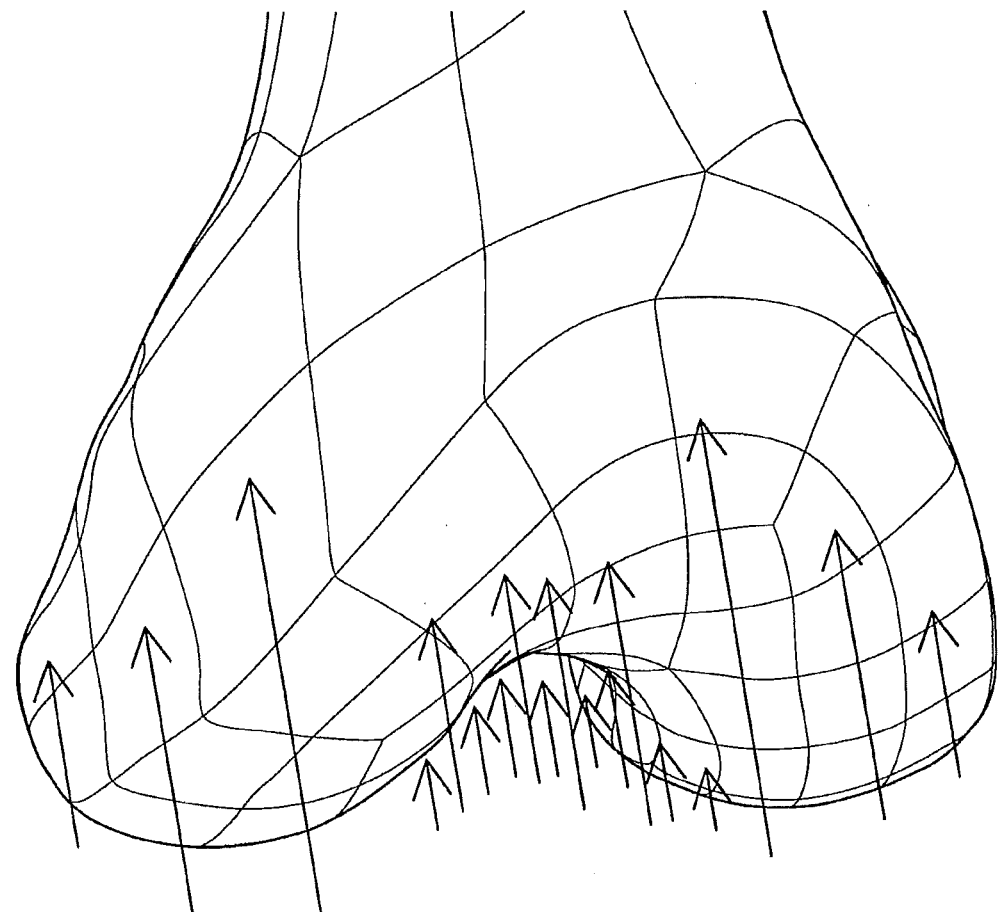
FIG. 20 illustrates potential points of contact between a femur bone and a patient-matched surgical instrument (not shown) according to another embodiment.

FIG. 20 shows several arrows conceptually illustrating substantially point contacts between a patient's anatomy and contacting portions of another embodiment of a surgical instrument. In the embodiment of FIG. 20, the arrows indicate that there are generally more points of contact proximate to areas of the patient's anatomy having more contour.

While contrary to the above teachings, it is also envisioned that a larger number of anatomy contacting portions may be concentrated in areas of the instrument having less contour. Thus, areas proximate to the femoral condyle portions of the instrument may be provided with more anatomy contacting portions than in areas proximate to the intercondylar notch portion of the instrument. In this way, the anatomy contacting portions are concentrated in areas where segmentation error may be less likely to exist (at least in some embodiments)—the larger, less contoured areas—rather than areas with a greater amount of contour. Since conventional patient scans (e.g., MRI) comprise a compilation of 2D image slices that are spaced by intervals of approximately 2-4 mm, interpolation algorithms or other methods are used to approximate anatomical geometries between the image data slices. By focusing contact portions in areas where there is less change in geometry between 2D image slices, instrument fit may be improved.

Figure 21:
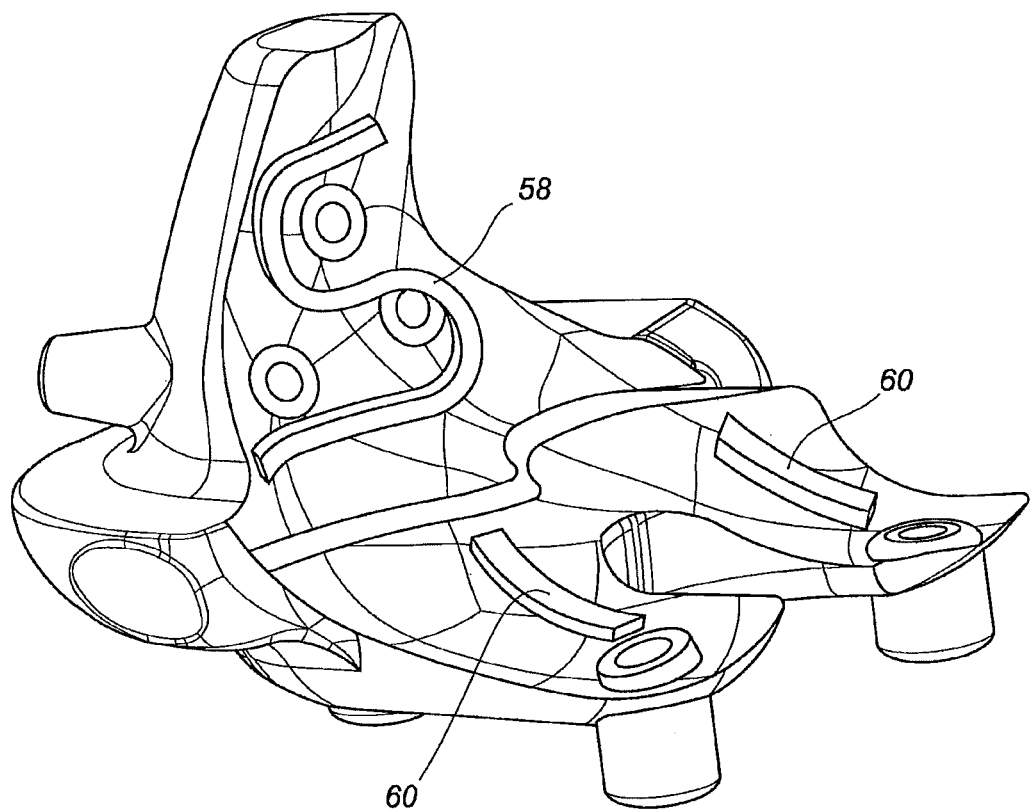
FIGS. 21 and 22 illustrate two embodiments of patient-matched surgical instruments in the form of femoral cutting guides, each having anatomy-contacting portions in the shape of substantial line segments.
Figure 22:
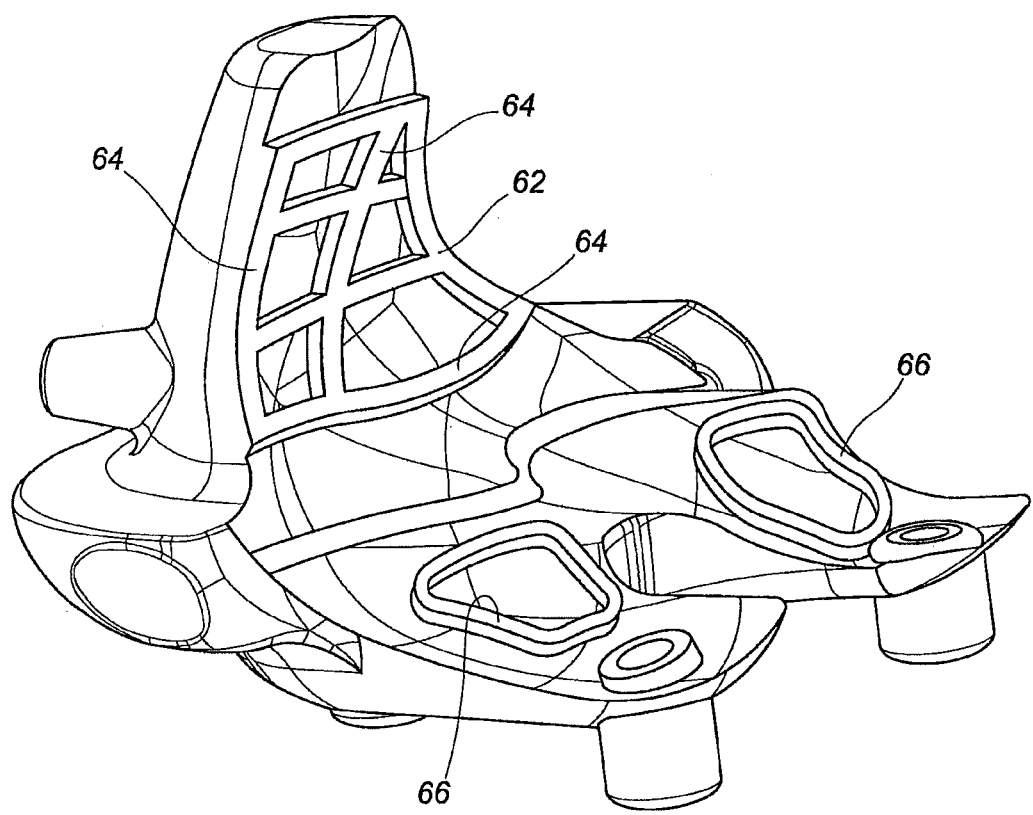

FIGS. 21 and 22 illustrate embodiments where the anatomy contacting portions are substantially linear contacts. The substantially linear contacts may be relatively straight (at least in two dimensions), or may have at least one curved segment. Thus, in the embodiment shown in FIG. 21, there is provided one "S-shaped" contacting portion 58 that provides greater contact with the patient's anatomy and may also increase internal and external rotational stability. As shown, there may also be other contacting portions 60 that are more linear than the S-shaped portion 58, contacting portions 60 being located proximate the condylar portions of the instrument. If desired, these two contacting portions 60 may be shaped to generally follow the apex contour of the condyles.

The anatomy contacting portions 58 and 60 shown in FIG. 21 are discreet in that they have a first end and a second end that are not connected to each other. In the embodiment shown in FIG. 22, the anatomy contacting portions connect with each other. Thus, there is provided a "waffle-shaped" contacting portion 62 including multiple line segments 64 connected to one another, and "ring-shaped" contacting portions 66 comprising a single curvilinear line segment connected at its ends. If desired, the ring-shaped contacting portions 66 may be located proximate the condylar portions of the instrument, such that the patient's condyles "nest" within the ring-shaped contacting portions 66. Any other type of hatch or grid pattern comprising multiple line segments, and/or oval or annulus-shaped line segments are also within the scope of this invention.

The anatomy contacting portions shown and described in FIGS. 21 and 22 may match to recessed portions of the patient's anatomy (such as the trochlear groove or intercondylar notch), but may also match portions of the anatomy that sit proud in relation to other anatomy (such as the medial and lateral distal condyles). The anatomy contacting portions may match either articulating or non-articulating portions of the patient's anatomy. If desired, one or more discrete substantially point contact portions (such as contacting portions 56 in FIG. 19) may be provided along with the line-segment contacting portions shown in FIGS. 21 and 22.

Figure 23:
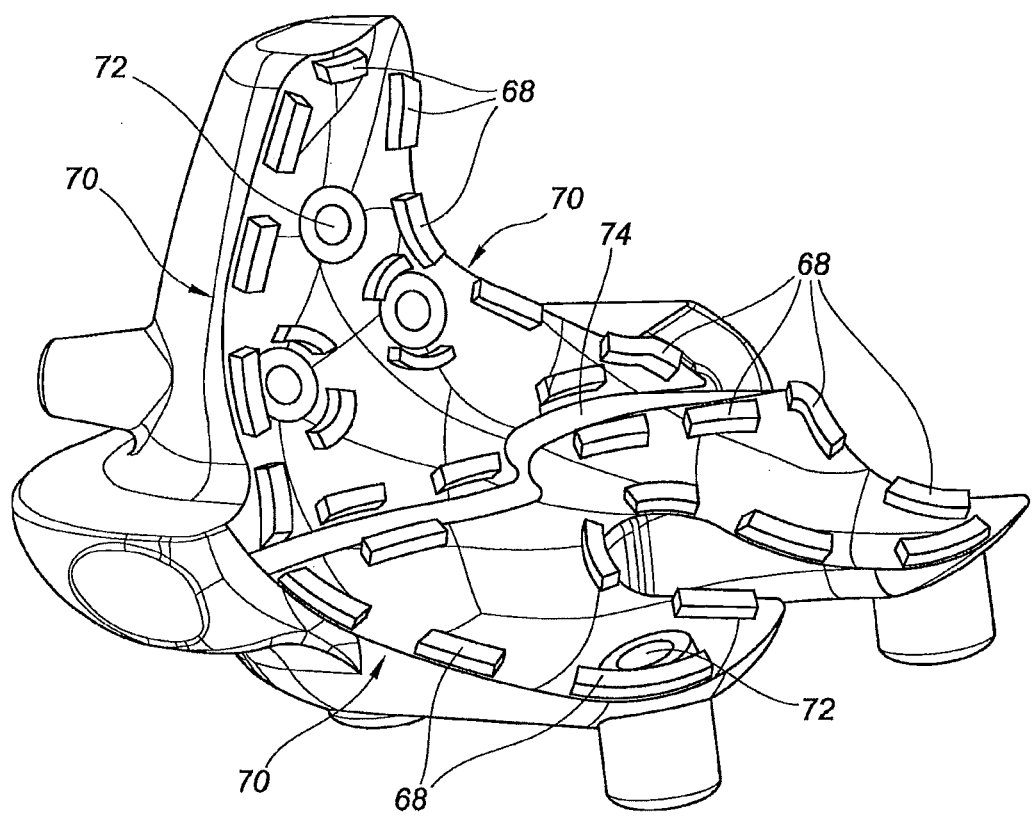
FIGS. 23 and 24A illustrate two embodiments of patient-matched surgical instruments in the form of femoral cutting guides, each having anatomy-contacting portions located generally around the peripheral areas of the instrument and/or guide structures of the instrument.
Figure 24A:
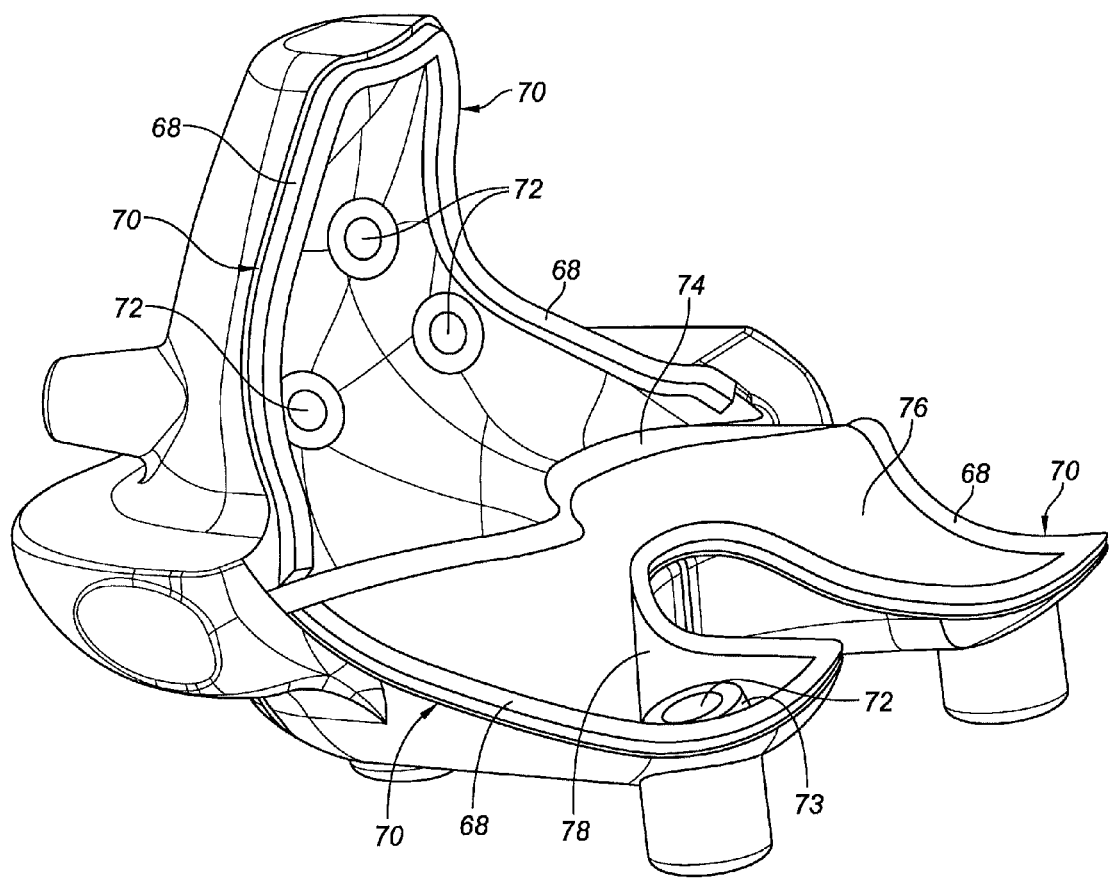
Figure 24B:
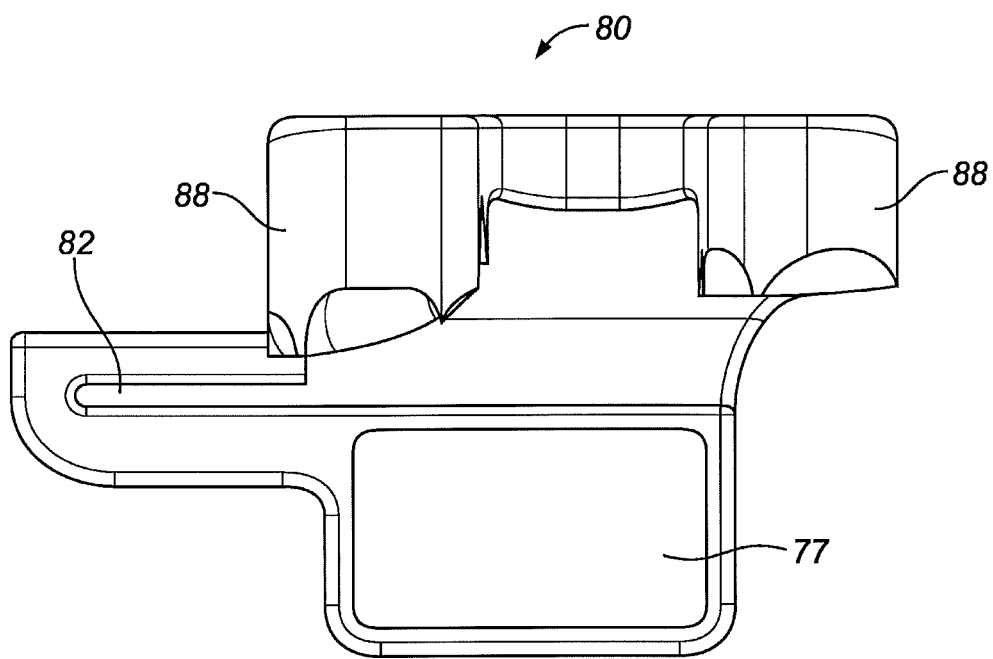
FIG. 24B illustrates an embodiment of a patient-matched surgical instrument in the form of a tibial cutting guide, having anatomy-contacting portions located generally around the peripheral areas of the instrument and/or guide structures of the instrument.

FIGS. 23, 24A, and 24B illustrate embodiments where the anatomy contacting portions 68 are more heavily concentrated in peripheral areas 70 of the instrument and/or guide structures (such as but not limited to apertures 72 to receive fixation pins, or through slots 74 to receive cutting instruments). It is not necessary in all embodiments for the anatomy contacting portions to extend completely around the perimeter of the surgical instrument. Rather, the contacting portions may only extend around a portion of the perimeter. Additionally, it is not necessary for the anatomy contacting portions to extend completely around the guide structures (the contacting portions may only be located on the top of the through-slot, for example), or for the contacting portions to extend around each of the guide structures (only some guide structures may be provided with contacting portions).

Locating the anatomy contacting portions in such peripheral areas may increase stability of the instrument when the instrument is placed on the patient's anatomy, or when the surgeon uses the guide structures (for example, when the through-slot receives a cutting instrument for cutting bone). In the embodiment shown in FIG. 23, the anatomy contacting portions 68 are discontinuous ridges that are shaped like rectangles or wedges. (Of course, other shapes may be provided, such as cylinders, cones, spheres, pyramids, or any other shape described herein.) In FIG. 24A, there is provided a single almost entirely continuous anatomy contacting portion 68 that extends around the perimeter 70 of the instrument. If desired, additional anatomy contacting portions may be placed in central regions of the patient-matched instrument.

Additionally, FIG. 24A shows that in certain embodiments of the femoral block, portions (e.g. portion 76) of the surgical instrument may be "hollow" such that they are defined by a sidewall 78, the top edges of which define the contacting portions 68 of the instrument. In FIG. 24A the bottom half of the surgical instrument is hollow, whereas the top half is non-hollow. In the bottom half, the anatomy contacting portions 68 extend into the surgical instrument and define the sidewalls 78 of the hollow bottom half. Thus, the bottom half of the instrument resembles a cup, where the lip of the cup comprises the anatomy contacting portions 68. In other embodiments, the entire surgical instrument may be hollow. In hollow portions of the instrument, pin bosses 73 define the pin apertures 72. Similarly, as illustrated in FIG. 24B, a tibial cutting block 80 can include hollow portions 77.

Any or all of the anatomy contacting portions described herein may be textured to improve the overall stability of the patient-matched instrument. For example, the texturing may include serration, points, cross-hatch, grooves, ridges, bumps, or barbs that increase the friction between the patient's anatomy and the patient-matched instrument. In certain embodiments the texturing at least slightly penetrates the patient's soft tissue or other anatomy, which may, in some embodiments, compensate for segmentation errors that may occur in regions having greater amounts of soft tissue. In some embodiments, it may be desirable to locate the textured portions proximate the perimeter of the instrument and/or guide structures. If desired, central regions of the condylar portions and anterior portion (where more hard tissue such as bone is located) may remain smooth for best fit.

Figure 25A:
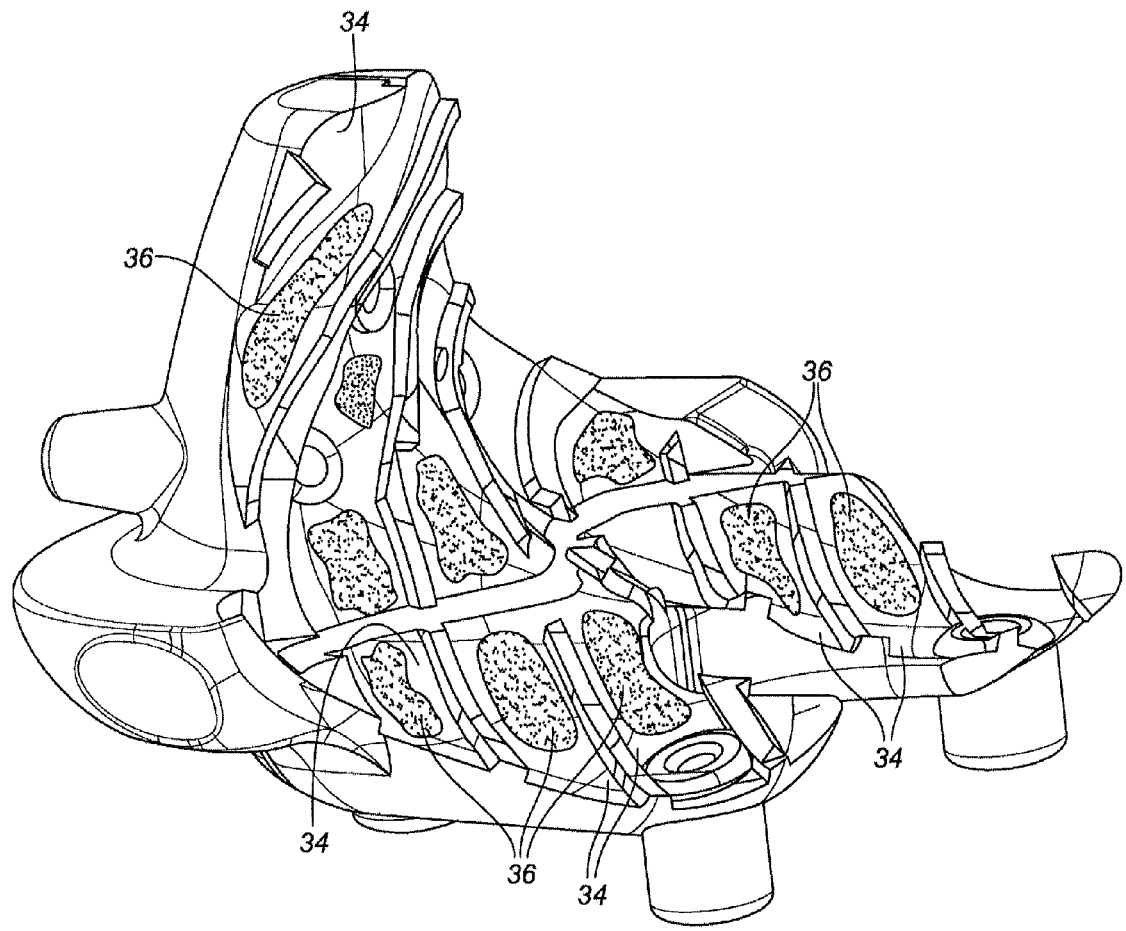
FIG. 25A illustrates a patient-matched surgical instrument including a pliant material.
Figure 25B:
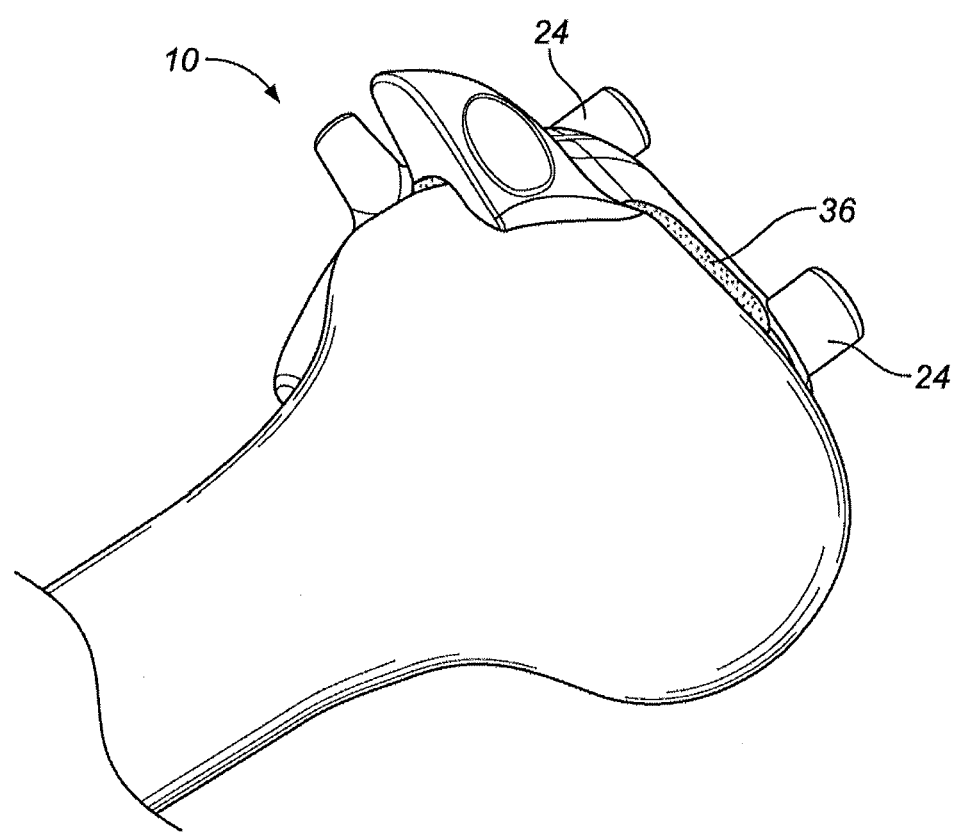
FIG. 25B illustrates a patient-matched surgical instrument including pliant material fitting to a bone.

FIGS. 25A and 25B illustrate an embodiment of a patient matched surgical instrument including pliant material 36 located in a recessed (or non-contacting) portion 34 of the instrument. With at least some of the embodiments described herein, when surgical instruments having anatomy contacting portions are placed against the patient's anatomy a gap or space may be left between the anatomy and the recessed portions (e.g. 34 in FIG. 25A) of the instrument that do not contact the anatomy. The gaps may give the perception of a non-conforming fit, and moreover, the gaps might contribute to instability of the instrument. Thus, at least one pliant portion may be provided within a recessed portion of the surgical instrument. In some embodiments, the pliant portion completely fills the respective recessed area (e.g. as shown in FIG. 25B), but in other embodiments, the pliant portion only fills a portion of the recessed area (e.g. as shown in FIG. 25A). The pliant portion may comprise a silicone material, polymer film, gauze, putty, or dough that presses against and at least partially takes on the shape of the patient's anatomy, filling any gaps that might otherwise be present between the discrete anatomy contacting portions. The pliant portions, together with the anatomy contacting portions, may in some embodiments approximate a continuous mirror-image surface of the patient's anatomy. Thus, the pliant portions provide the benefits of a continuous mirror-image surface (such as stability) to surgical instruments that only have discontinuous anatomy contacting portions. The pliant portions may be coupled to the surgical instrument either before or during surgery, using adhesive, mechanical fasteners, welding, or the like. Alternatively, the pliant portions may simply be placed within the recessed portions without any structure or substance to couple the pliant portion to the instrument. In some embodiments, a pliant material such as a polymer may be injected into the recesses of the instrument after manufacture.

Various embodiments of patient-matched surgical instruments may feature different fill depths of a pliant material in the recessed portions. For instance, in one embodiment, the pliant material may fill the recessed portions up to the level of the surrounding anatomy contacting portions; however, in other embodiments, the pliant material may be below the level of the surrounding anatomy contacting portions or above the level of the surrounding anatomy contacting portions. In embodiments where the fill level of the pliant material is below the level of the surrounding anatomy contacting portions, it may facilitate visualizing the fit of the instrument on the anatomy. In some embodiments where the pliant material is level with surrounding anatomy contacting portions, the pliant material may also contact the anatomy and add at least some degree of stability to the instrument/anatomy interaction. In some embodiments where the fill level of the pliant material is above the level of the surrounding anatomy contacting portions, pressing the instrument onto the anatomy may cause the pliant material to expand, filling in the recessed portions. In at least some these embodiments, such as the embodiment where the pliant material is above the level of the surrounding anatomy contacting portions, the pliant material may be held in place by pinning the instrument to the anatomy. In this and other embodiments, the pliant material may provide increased friction between the instrument and anatomy, such that the position and orientation of the instrument on the anatomy is further maintained during the pinning process.

In some embodiments, the pliant material may be more localized (partially or entirely) in areas configured for contact with bony anatomy (e.g. relatively superior, anterior portions of the anatomy facing side of a femoral cutting guide) and the anatomy contacting portions may be more localized (partially or entirely) in areas configured for contact with cartilagenous anatomy (e.g. condylar and other areas of a femoral cutting guide). In other embodiments, other distributions (either regular or irregular) of pliant material and anatomy contacting portions are possible.

Figure 11:
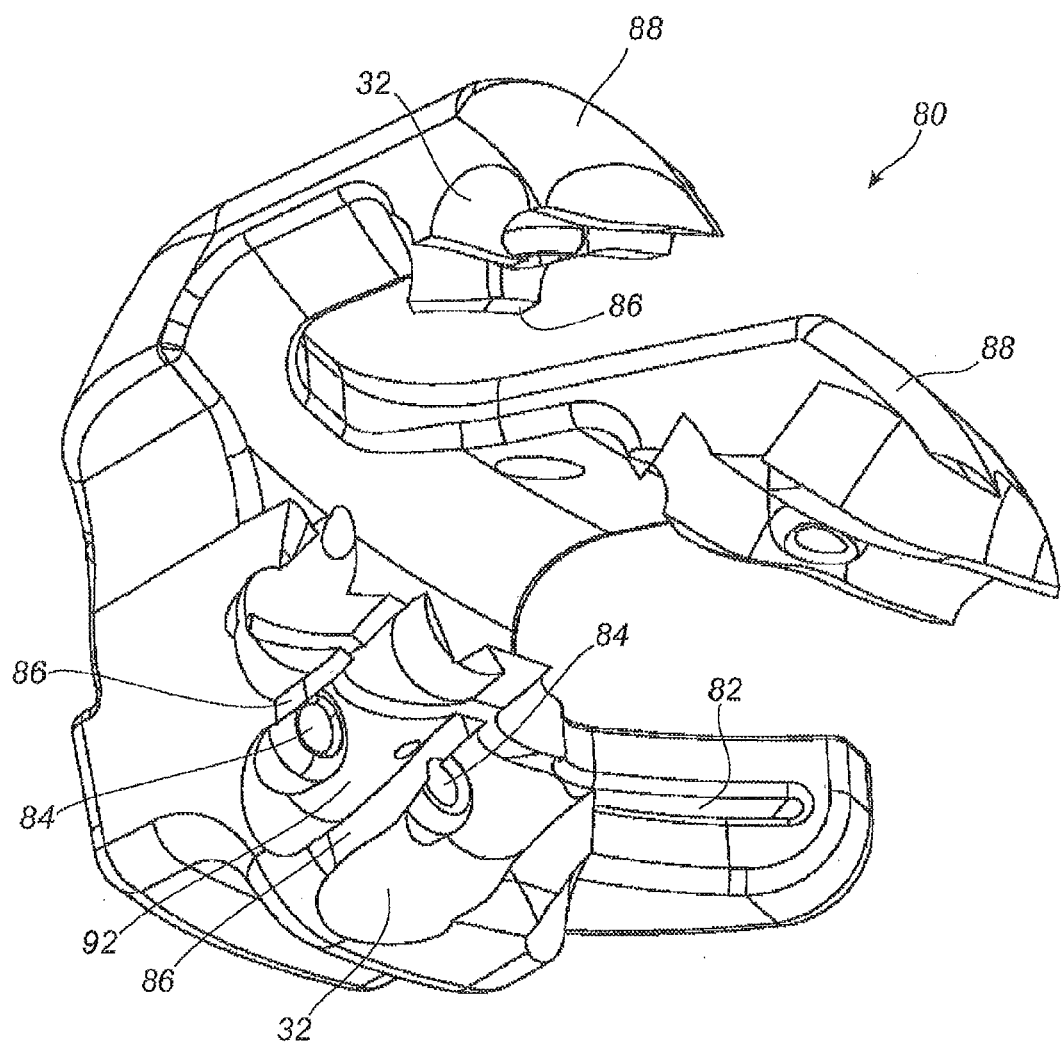
Figure 12:
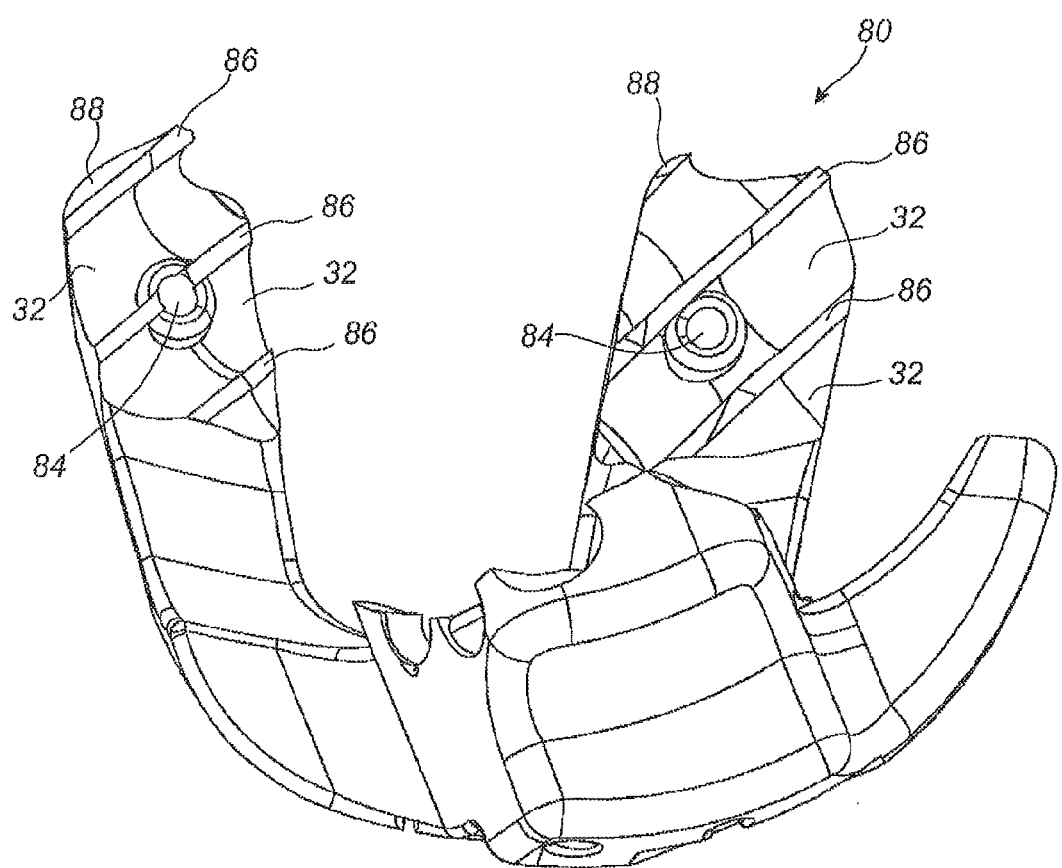
Figure 13:
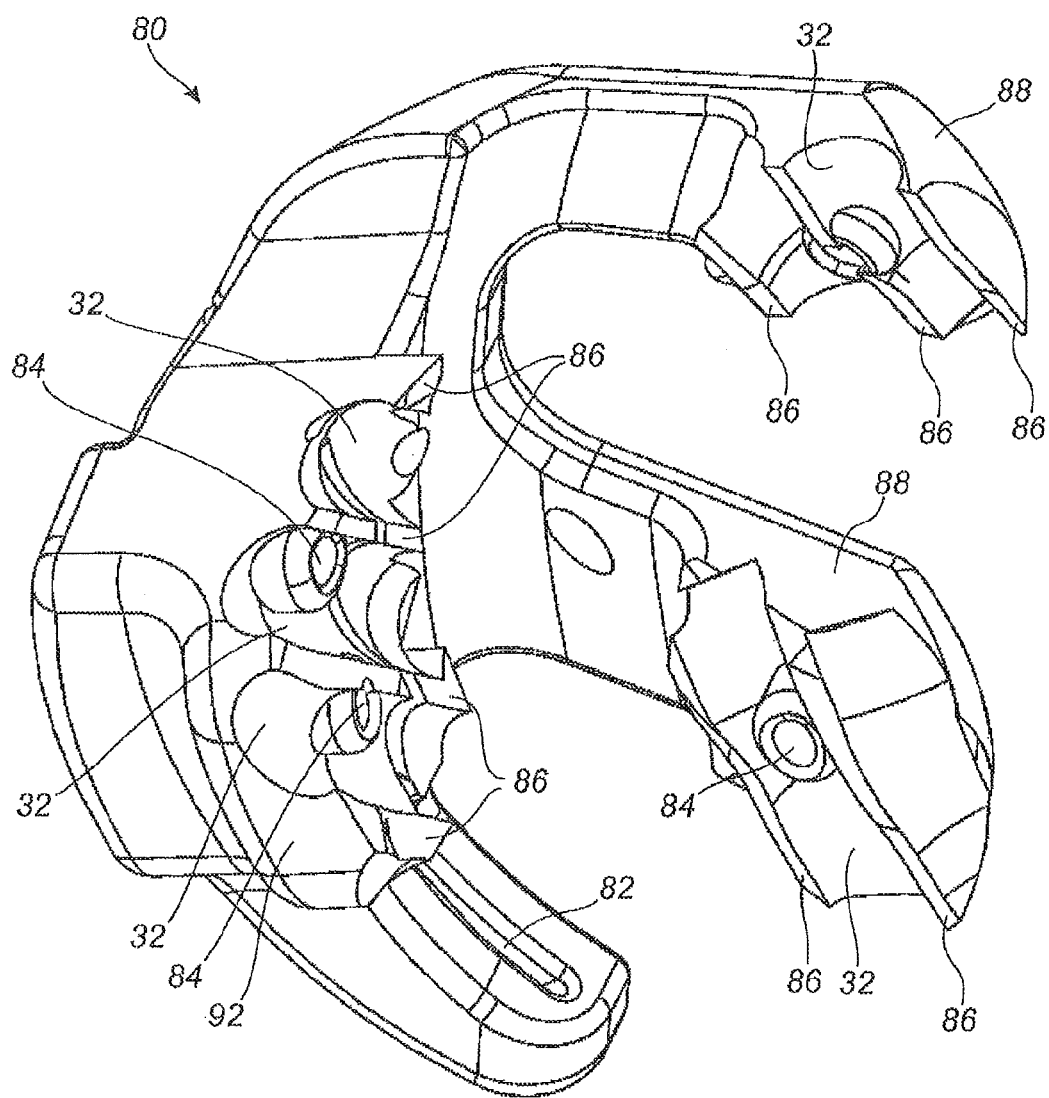
Figure 14:
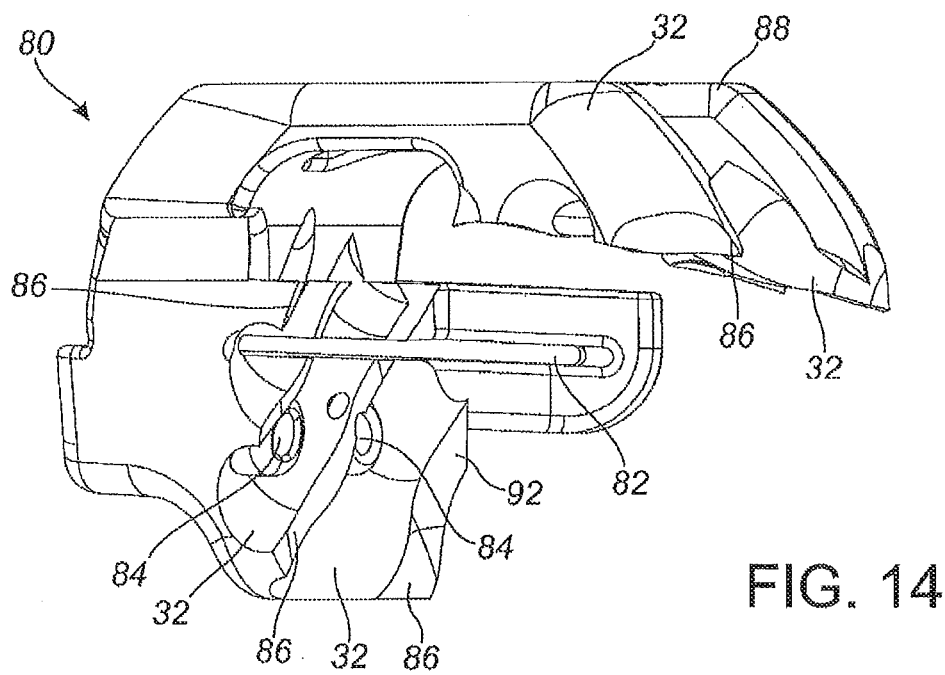

FIGS. 9-14 illustrate an embodiment of a patient-matched surgical instrument, in this instance a tibial cutting guide 80. The tibial guide 80 shown includes a guide 82 for directing a saw blade (or, in other embodiments, for directing other types of surgical tools such as a milling bit, osteotome, drill, wire, or pin) Although not shown, in some embodiments, the surgical instrument may have features for attaching modules for directing surgical tools rather than incorporating a surgical guide directly into the tool. The tibial cutting guide 80 shown in FIGS. 9-14 also includes several apertures 84 for receiving pins or other fasteners for securing the instrument to the patient. The guide portion 82 of the tibial cutting guide 80 shown in FIGS. 9-14 is partially cantilevered off of other portions, and may be configured to contact a patient's anatomy to some degree or may be configured to clear the patient's anatomy relative to anatomy contacting portions of the instrument. In the particular embodiment shown, as best seen in FIG. 11, the cantilevered portion of guide 82 is not configured to directly contact the patient's anatomy, whereas central portions of the guide 82 do include anatomy contacting portions 86 on the anatomy facing side of the tibial cutting guide 80.

Figure 9:
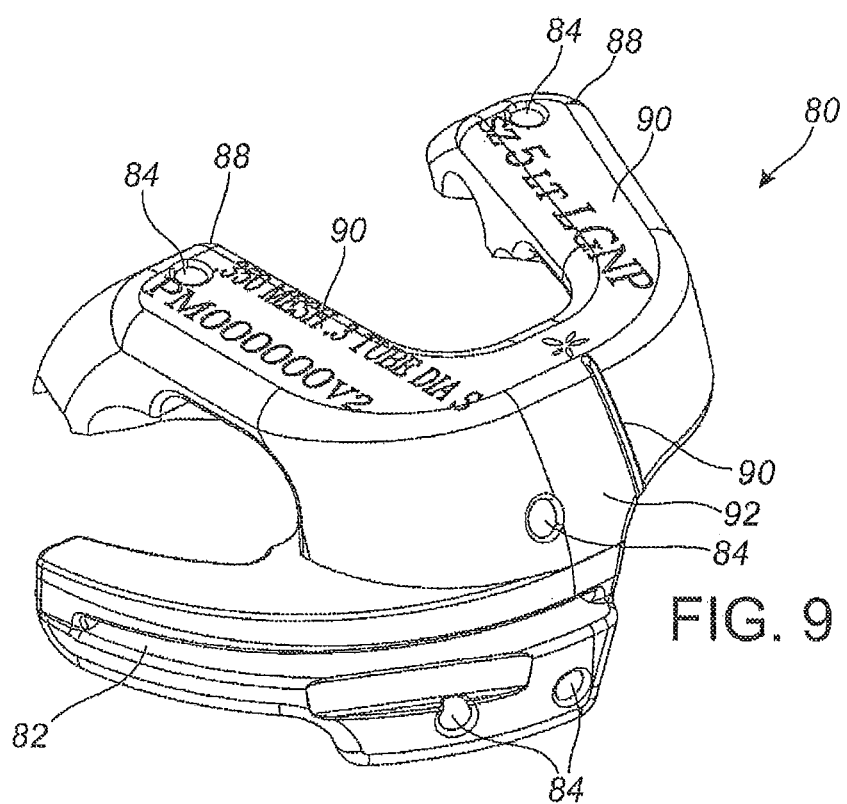
FIGS. 9-14 illustrate an embodiment of a patient-matched surgical instrument in the form of a tibial cutting guide.
Figure 10A:
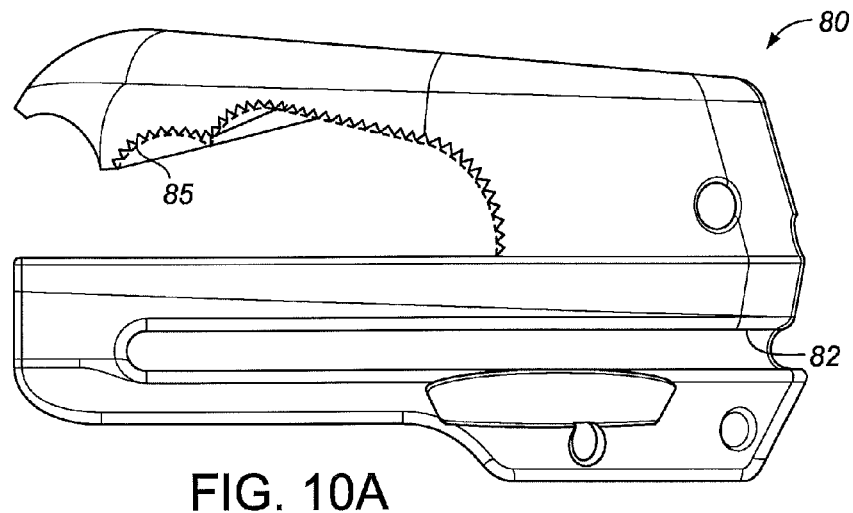
Figure 10B:
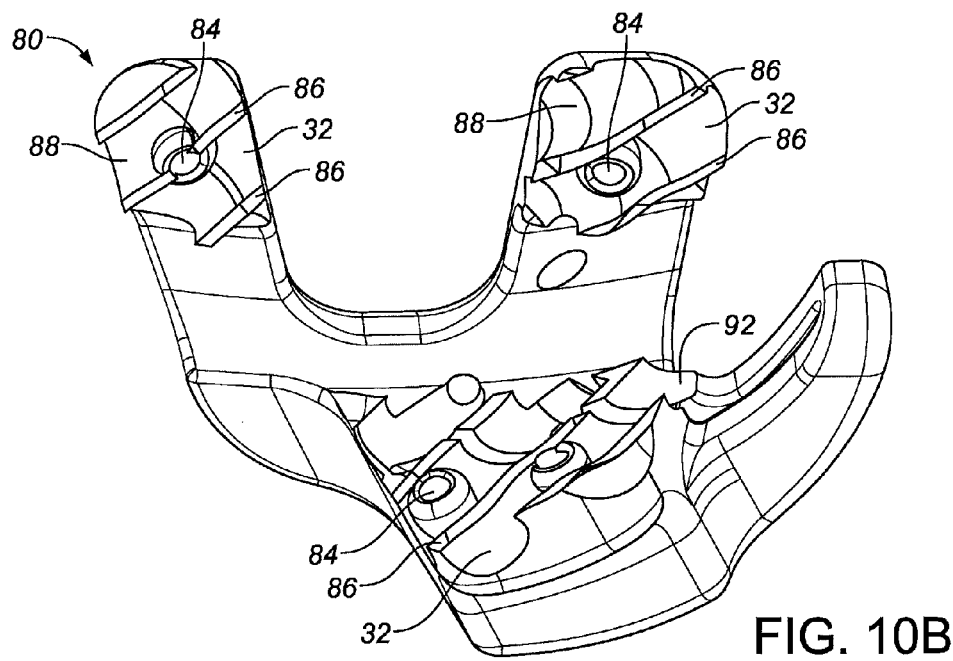

In the embodiment of FIGS. 9-14, the tibial cutting guide 80 also includes two paddles 88, portions of which are for contacting superior portions of a proximal tibia. In the particular embodiment shown, the two paddles 88 are provided for contacting points on medial and lateral articular zones of a proximal tibial plateau, adjacent the tibial eminence, although, in other embodiments, the paddles may be designed to contact other portions of the anatomy. As shown in FIG. 9, indicia 90 may be provided on the instrument for indicating relative mechanical axis alignment, size, patient data, data relative to the surgery to be performed, data regarding an orientation of the instrument, or surgeon data, without limitation.

The tibial cutting guide 80 of FIGS. 9-14 is similar to the femoral cutting guide of FIGS. 1-8 in that it employs anatomy contacting portions (here ridges 86) on the anatomy facing side of the instrument. The anatomy contacting portions 86 shown are configured to create spline contacts 85 between the instrument and the patient's tibial bone and/or cartilage as shown in FIG. 10A, although many other types, arrangements and distributions of anatomy contacting portions are also possible. An anterior portion 92 of the instrument is configured to partially engage cortical bone adjacent the anterior cortex and medial ⅓ of the tibial tubercle. The spline contacts shown are generally evenly distributed about the anterior portion 92 and distal paddle portions 88 of the instrument; however, as described above, the anatomy contacting portions may be randomized, or distributed in some other predetermined non-homogeneous fashion. Moreover, as previously stated, the number, location, orientation, size, width, profile, continuity, and shape of each anatomy contacting portion may be varied as needed to optimize interaction with a particular patient's unique anatomy or for other purposes.

Figure 15:
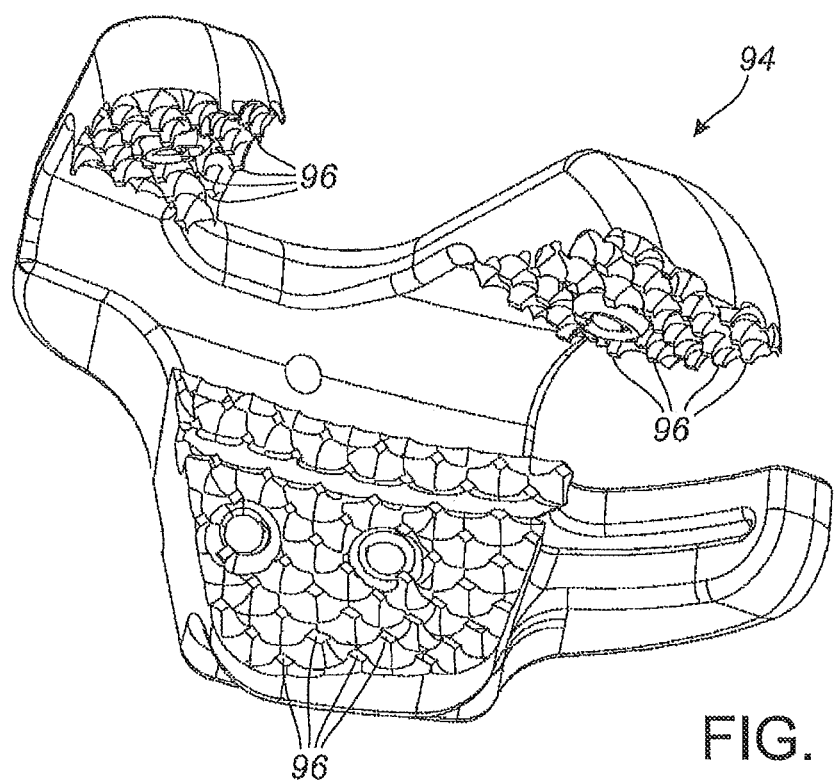
FIGS. 15-16 illustrate an embodiment of a patient-matched surgical instrument in the form of a tibial cutting guide.
Figure 16:
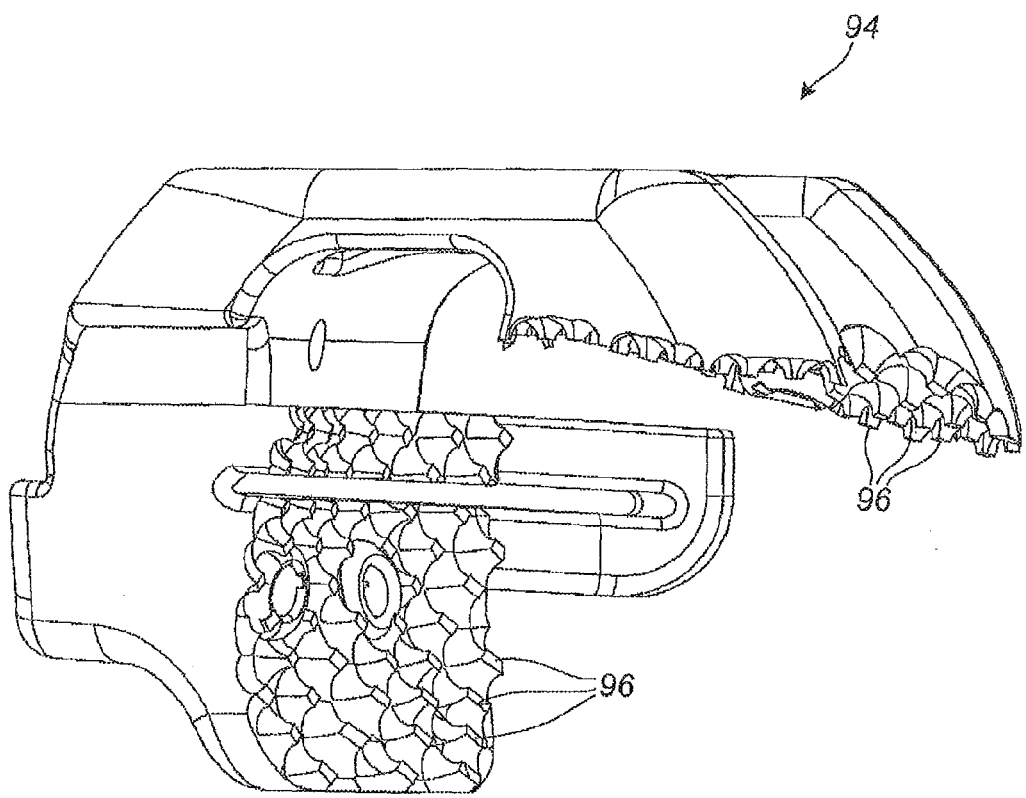
Figure 46:
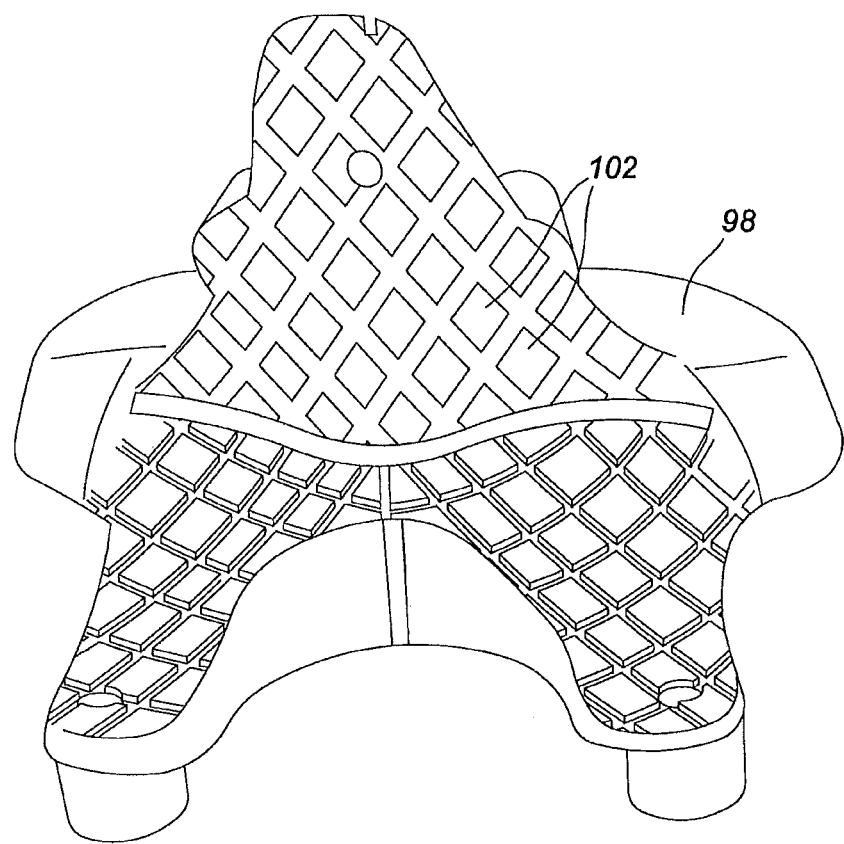
FIGS. 46 and 47 illustrate additional embodiments of patient-matched surgical instruments.
Figure 47:
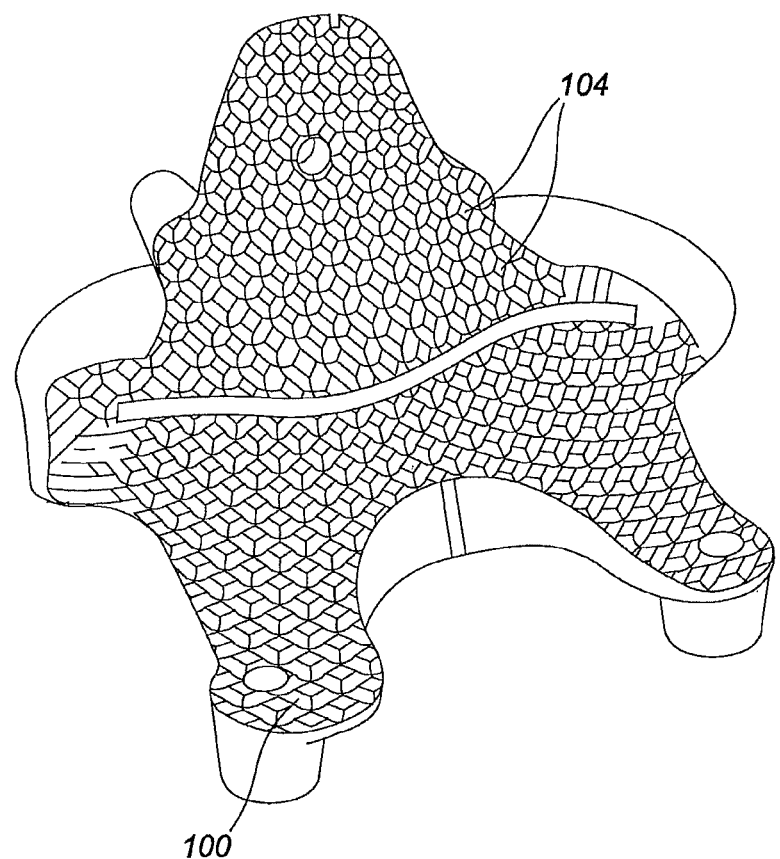

FIGS. 15-16 illustrate another embodiment of a patient matched tibial cutting guide 94 in which the anatomy contacting portions are several substantially point contacts 96. As shown, each point contact 96 includes a pad at its peak for contact with a point on the patient's anatomy. In some embodiments, the pad may be substantially square, and may range in size from 0.1 to 10 mm square (measured along a side of the square) in some embodiments, from 0.5 to 5 mm square in some embodiments, and from 1 to 3 mm square in some embodiments. FIGS. 46 and 47 schematically show other patient-matched instruments (femoral cutting guides 98 and 100 respectively) having different sized pads (102 and 104 respectively). In some embodiments, the pads are not square shaped, and may take on other shapes such as circles, triangles, rectangles, other polygons, or other shapes. In some embodiments, the substantially point contacts are not pads, but contact the anatomy at only one or a very limited number of points. For instance, in some embodiments, each substantially point contact may have a rounded apex or sharp apex (as opposed to the flat apexes shown) that only contacts the anatomy at a single point or very small number of points. In some embodiments, each substantially point contact may define multiple peaks that each contacts the anatomy in a limited number or only a single point.

FIGS. 17A-17C illustrate additional embodiments of patient matched surgical instruments. FIG. 17A illustrates a tibial cutting guide 106 similar to that shown in FIGS. 15-16 in that anatomy contacting portions 108 are provided on both the paddles 110 and the anterior portion 112 as a plurality of substantial point contacts (which, as mentioned earlier, make take on a variety of forms, including, but not limited to, a series of bumps, domes, spikes, cones, cylinders, polyhedrons (e.g., triangles, diamonds, pyramids), or other geometries or structures which would create substantially point contacts between the instrument and a patient's anatomy). As shown in FIG. 17A, however, central areas 114 of the anterior portion 112 are devoid of/have a lower concentration of anatomy contacting portions 108, whereas a larger concentration of anatomy contacting portions 108 is provided on a periphery or perimeter of the anterior portion 112 and areas of the instrument adjacent a guide structure 116. FIGS. 17B and 17C illustrate other embodiments of a customized surgical instrument for a tibia—each comprising a first region having one type of anatomy contacting portions, and a second region comprising another type of anatomy contacting portions. In particular, FIG. 17B shows an embodiment in which paddles of the instrument include dimples 118 configured for substantially point contact with a patient's unique anatomy, and the anterior portion of the customized surgical instrument includes raised splines 120 configured to present spline/substantial line contacts with respect to the patient's anatomy. FIG. 17C shows an embodiment in which the anterior portion of the patient-matched surgical instrument includes dimples 122 configured for providing a series of substantially point contacts with a patient's unique anatomy, and the paddles of the customized surgical instrument include raised splines 124 configured to present spline/substantially line contacts with respect to a patient's anatomy.

FIGS. 26-35 illustrate various method steps associated with the creation of some of the patient-matched surgical instruments shown and described herein, according to some embodiments. While the method steps are shown and described in conjunction with a patient's distal femur, it should be noted that the various method steps may be applied to any portion of a patient's anatomy, without limitation. In addition, the embodiments of the patient-matched surgical instruments discussed above for FIGS. 1-25, and other embodiments of patient-matched surgical instruments within the scope of the present disclosure, do not necessarily have to be created using the embodiments of methods illustrated in FIGS. 26-35 and can be created in a variety of other ways. Moreover, the methods shown and described below may be used to create patient-matched surgical instruments other than those shown in FIGS. 1-25.

Figure 48:
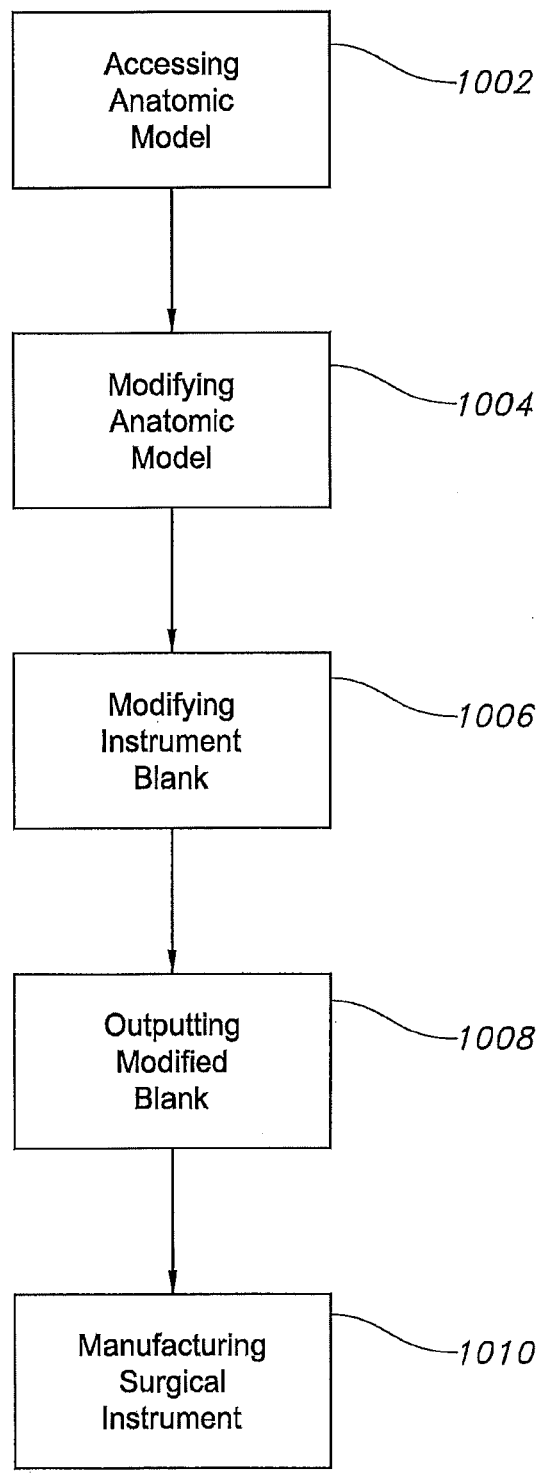
FIG. 48 schematically illustrates one embodiment of a method of designing and manufacturing a surgical instrument.

In general, the non-limiting embodiment illustrated in FIGS. 26-35 involves: (1) creating, obtaining or otherwise accessing a digital or other form of a three dimensional model of the patient's anatomy of interest; (2) applying one or more mesh or grid overlays onto portions of the bone model; (3) performing a sweep function that modifies the mesh or grid overlay(s) to create a geometric construct that defines areas where the anatomy contacting portions are and areas where the anatomy contacting portions are not on the anatomy facing side of the patient specific instrument; (4) merging the modified overlay(s) with the bone model; and (5) applying an oversized blank of the instrument to the modified bone model to identify portions of the blank for removal (in some embodiments, portions of a virtual blank for removal) such that patient-matched anatomy contacting portions are formed or otherwise present or created to define a patient-matched instrument. FIG. 48 schematically illustrates one embodiment of a method involving accessing a three dimensional anatomic model (1002), modifying the anatomic model (1004), using the modified anatomic model to modify an instrument blank (1006), outputting the modified instrument blank to a manufacturing device (1008), and manufacturing the surgical instrument (1010).

Figure 26:
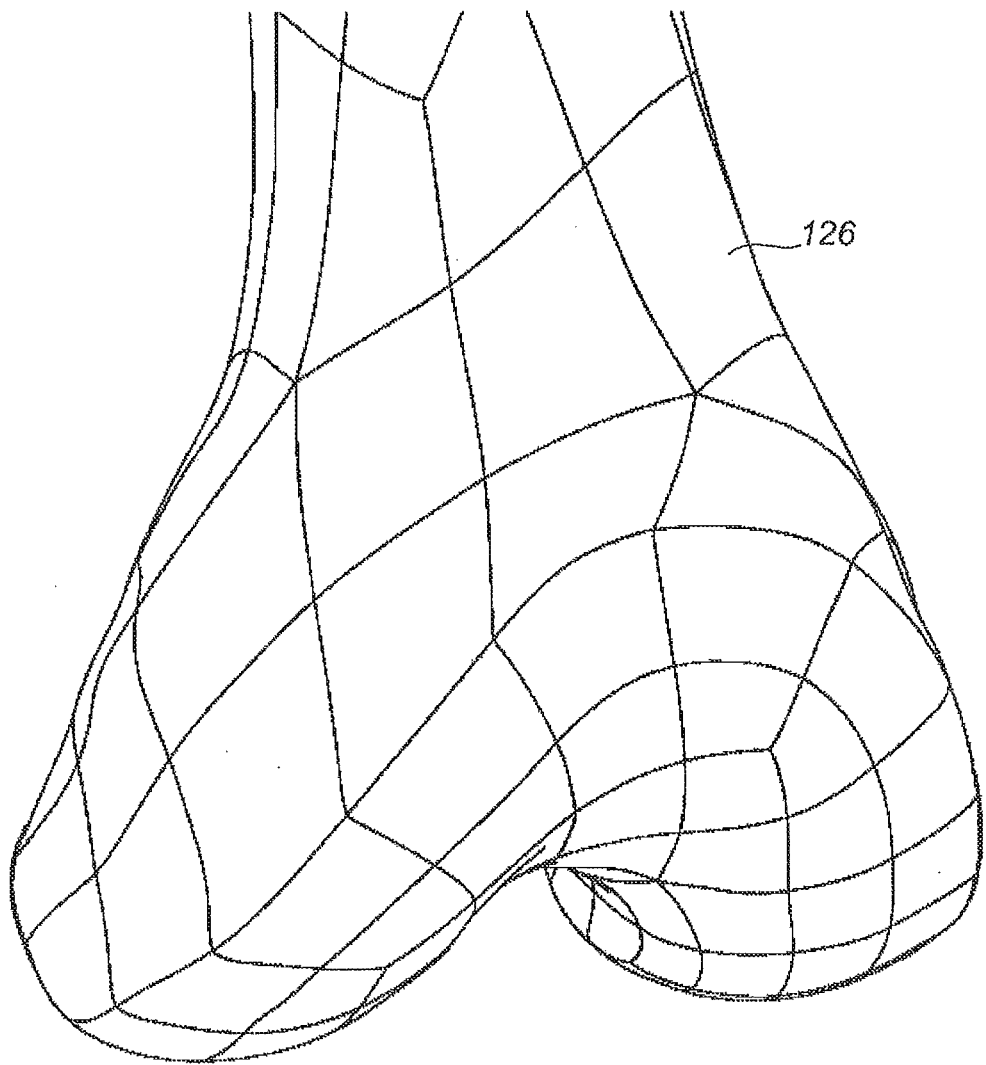
FIG. 26 illustrates a method step of creating a three-dimensional patient-specific anatomic model according to one embodiment.

FIG. 26 illustrates a method step of creating a first anatomic model 126 utilizing 3D imaging data obtained from a patient as conventionally done, such as by, but not limited to, magnetic resonance imaging, x-ray (including digital x-rays), ultrasound, or other techniques. In some embodiments, non-image based technologies may be used to obtain sufficient data about the 3D structure of the anatomy of interest to allow a patient-matched instrument in accordance with this disclosure to be created. In some embodiments, the first anatomic model is not a complete model of the particular portion of the anatomy of interest, but is only a model of certain key or desired anatomical points or portions of the anatomy of interest. The first anatomic model 126 may be electronically stored in a computer storage memory and imported into a computer assisted design (CAD) software package or other types of design software packages.

Figure 27A:
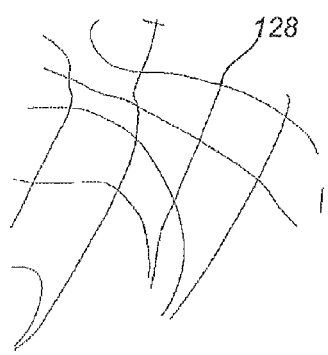
FIG. 27A illustrates an embodiment of a method step of creating and applying a first mesh structure to a first portion of a first anatomic model.

FIG. 27A illustrates a method step of creating and applying a first mesh structure 128 to a first portion of a first anatomic model 126. In some embodiments, the first mesh structure 128 (either by itself or in conjunction with other mesh structures) defines or at least roughly corresponds to at least some aspects of the number, position, and/or orientation of the anatomy contacting portions of the patient-matched instrument as well as the recessed portions interspersed among those anatomy contacting portions. Although the mesh structure 128 shown in FIG. 27A may be characterized as being defined by a square, uniform grid pattern, the mesh structure may have any geometric shape, size, porosity, or density, including a gradient density or porosity. The mesh structure may be evenly distributed, or may be random in nature, or otherwise have a predetermined pattern. Shown in FIG. 27A is one embodiment of an anterior mesh structure 128 for application to, or projection onto or "wrapping around" an anterior outer surface of the first model 126 shown in FIG. 26 (which here is a distal femur, the "anterior outer surface" being adjacent the trochlear groove, anterior cortex, and surrounding articular surfaces).

Figure 27B:
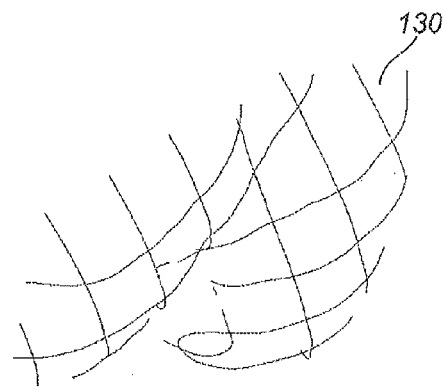
FIG. 27B illustrates an embodiment of a method step of creating and applying a second mesh structure to a second portion of the first anatomic model.

FIG. 27B illustrates a method step of creating and applying a second mesh structure 130 to a second portion of the first anatomic model 126 of FIG. 26. As previously mentioned, the mesh structure may have any geometric shape, size, porosity, or density, including a gradient density or porosity. The mesh structure may be evenly distributed, or may be random in nature, or otherwise have a predetermined pattern. Shown in FIG. 27B is an embodiment of a distal mesh 130 to be applied to or otherwise projected onto or "wrapped around" one or more inferior surfaces of the first model 126 (here, adjacent the condyles and intercondylar notch of the first bone model 126 shown in FIG. 26).

Figure 27C:
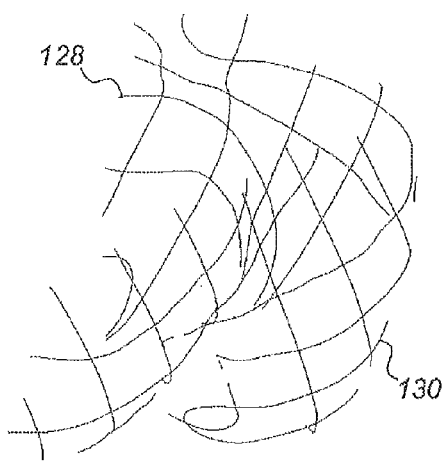
FIG. 27C illustrates an embodiment of a method step of creating a first mesh structure and a second mesh structure, and applying the first and second mesh structures to first and second portions of a first anatomic model, respectively.

FIG. 27C illustrates a method step of creating a first mesh structure 128 and a second mesh structure 130, and applying both the first and second mesh structures to first and second portions of the first anatomic model 126 (e.g. of FIG. 26), respectively. The first and second mesh structures 128 and 130 may be united as one homogenous mesh structure, or the mesh structures may be kept independent and distinct so that different sweep functions may be applied to each mesh structure to form different anatomy-contacting portion profiles on the different portions of the first anatomic model 126. As shown in FIG. 27C, the mesh structures 128 and 130 may overlap one another, although, in other embodiments, they may be designed not to overlap when applied to the first anatomic model 126.

Figure 27D:
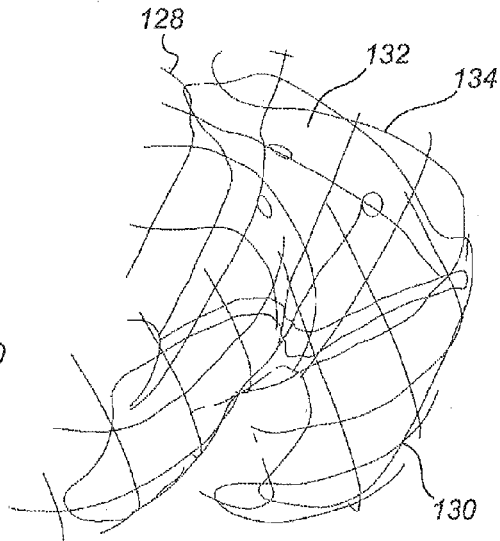
FIG. 27D illustrates the method step of FIG. 27C further including the method step of determining an intersection of a surgical instrument blank with respect to a first anatomic model.

FIG. 27D illustrates an embodiment of a method step of determining an intersection of a surgical instrument blank 132 with respect to the first anatomic model 126. As shown in FIG. 27D, and will be described in more detail hereinafter, the surgical instrument blank 132 (which may be sized according to an individual patient or "universal" for all patient sizes) is virtually merged with the first anatomic model 126 which includes the first and/or second mesh structures 128 and 130 (or other numbers and combinations of mesh structures in other embodiments). The intersection between the blank 132 and the first anatomic model 126 defines an intersection perimeter 134 (i.e., the border of the interface between the virtually merged blank and first anatomic model). The intersection perimeter 134 is shown to be superimposed over the first and second mesh structures 128 and 130 in FIG. 27D. In some embodiments, the mesh structures is designed in such a manner (or the method is otherwise altered) to avoid a separate step of determining intersections between the blank and the first anatomic model 126.

Figure 28:
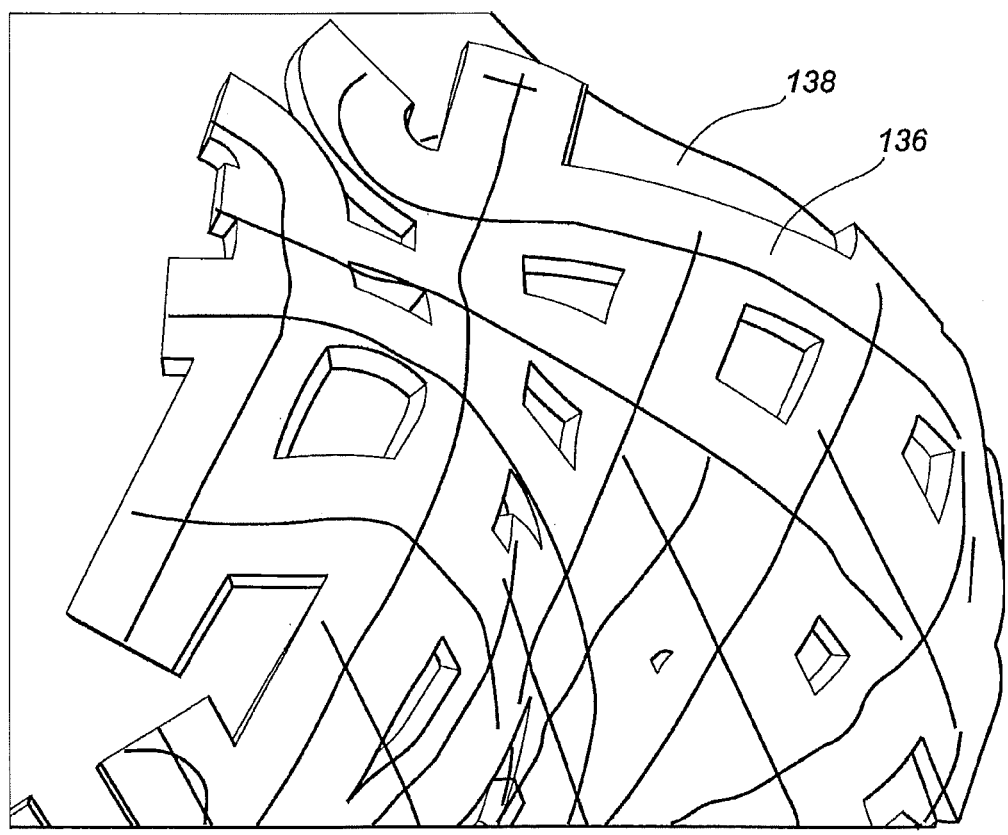
FIGS. 28-31 illustrate an embodiment of a method step of performing one or more sweep functions to a mesh structure, after said mesh structure is applied to an outer portion of a first anatomic model, to create a modified first anatomic model.

FIGS. 28-31 illustrate a method step of performing one or more sweep functions to the mesh structure(s) to create an expanded mesh structure 136. The one or more sweep functions may be executed before or after the mesh structures 128 and 130 are applied to the first anatomic model 126. In other embodiments, performing a sweep function is unnecessary and the geometry of the mesh structure may already include geometries other than simple lines or grids such that "expanding" on a line grid is not necessary. In the embodiment illustrated in FIGS. 28-31, after the one or more sweep functions are executed, the resulting volume of the expanded mesh structure 136 and the first anatomic model 126 are united to create a modified first anatomic model 138. Shown in FIG. 28 is a portion of a modified first anatomic model 138 incorporating the first anterior mesh structure 128 shown in FIG. 27A and the second distal mesh structure 130 shown in FIG. 27B, after the mesh structures have been expanded by one or more sweep functions in CAD software. The resulting volumes of the first and second expanded mesh structures are shown to be united with the volume of the first anatomic model 126 shown in FIG. 26. In the embodiment shown in FIG. 28, the indentations left in the modified first anatomic model 138 after the expanded mesh structure has been united with the anatomic model 126 may correspond (at least partially) to the locations, sizes, geometries and other aspects of the anatomy contacting portions of the patient-matched surgical instrument.

In some embodiments, the sweep function may be applied to a first mesh structure that is united with the bone model prior to applying the same or a different sweep function to a second mesh structure for uniting with the bone model. In other embodiments, the first and second mesh structures may both have the same or different sweep functions applied and then both be united with the bone model at the same time. It will be apparent to one of skill in the art that other combinations and different orderings of these method steps are possible and within the scope of possible embodiments discussed herein.

It should be noted that while the sweep function applied to the first and second mesh structures 128 and 130 shown in FIG. 28 include a flattened rectangular cross-section, any cross-sectional geometry may be applied to mesh structures described herein. For example, a triangular, polygonal, circular, oval, irregular, or other cross-sectional shape or profile may be applied to the mesh structures to obtain a different modified first anatomic model. Moreover, a different sweep function may be applied to each line, area, region, strut or segment of a mesh structure to obtain an irregular or asymmetric modified first anatomic model. Therefore, the drawings merely illustrate one particular embodiment of many possible permutations of a modified first bone model.

Figure 29:
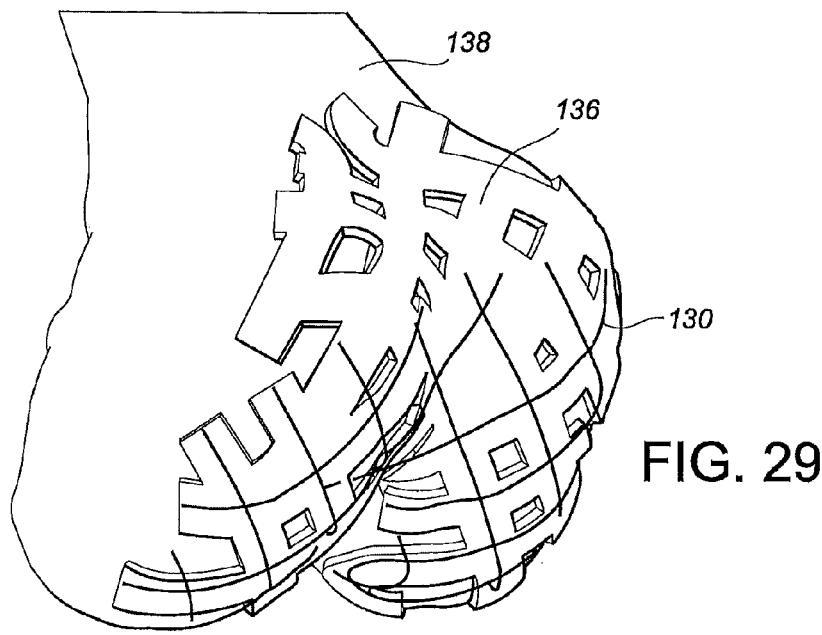
Figure 30:
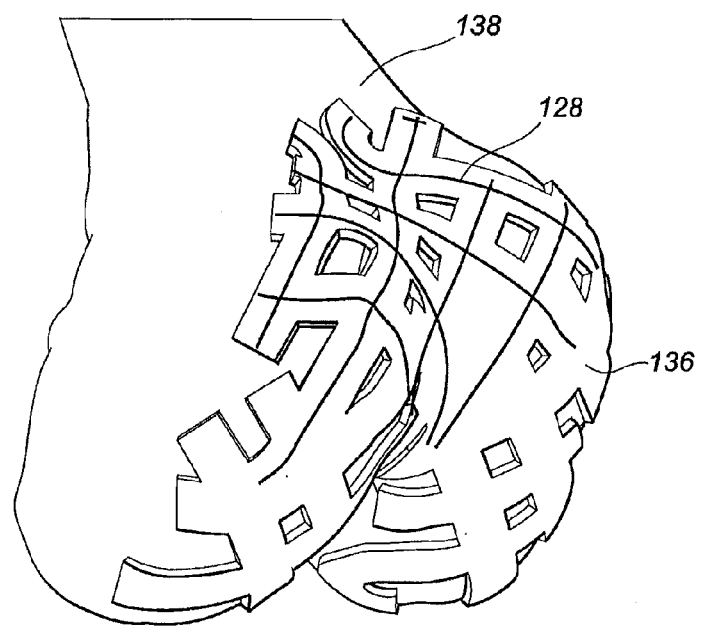
Figure 31:
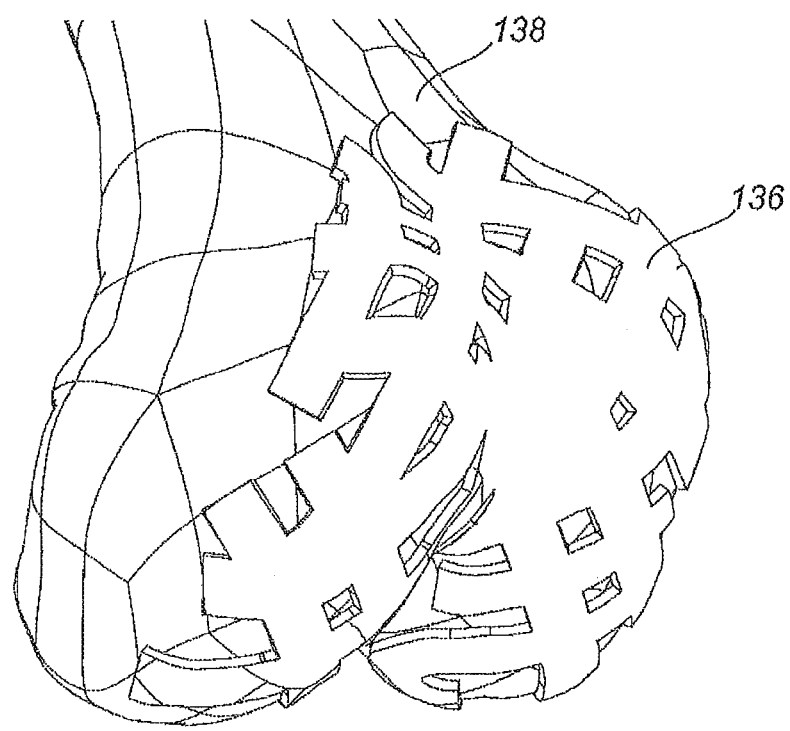

FIG. 29 illustrates the second (distal) mesh structure 130 of FIG. 27B superimposed on the modified first anatomic model 138 of FIG. 28. FIG. 30 illustrates the first (anterior) mesh structure 128 of FIG. 27A superimposed on the modified first anatomic model of FIG. 28. FIG. 31 further depicts the modified first anatomic model 138 of FIG. 28 according to some embodiments.

In some embodiments, the steps of applying one or more mesh structures and/or performing one or more sweep functions are unnecessary and a "modified" anatomic model may be created directly as a result of imaging of the patient's anatomy. For instance, in some embodiments, the software or other mechanisms obtaining, controlling and/or processing data related to the patient's anatomy may be programmed or operate such that only certain, limited portions of the anatomy of interest are imaged, such portions corresponding to areas where anatomy contacting portions of the patient-matched instrument are located.

Figures 32A, 32B, 32C:
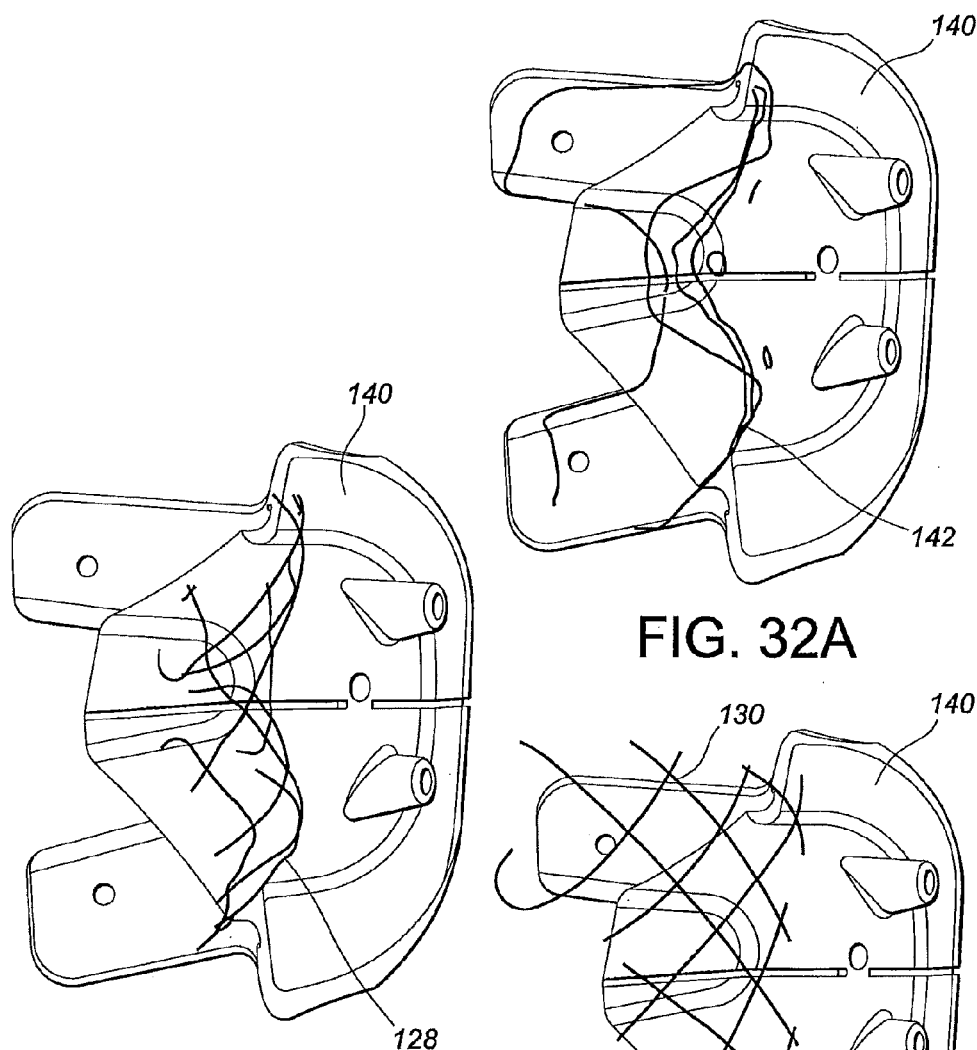
FIGS. 32A and 33A illustrate a surgical instrument blank for use with a modified first anatomic model according to some embodiments, having superimposed thereon a virtual intersection with the first modified anatomic model.
FIGS. 32B and 33B illustrate the surgical instrument blank of FIG. 32A, having superimposed thereon a first mesh structure applied to a first portion of a first anatomic model.
FIGS. 32C and 33C illustrate the surgical instrument blank of FIG. 32A, having superimposed thereon a second mesh structure applied to a second portion of a first anatomic model.
Figures 33A, 33B, 33C:
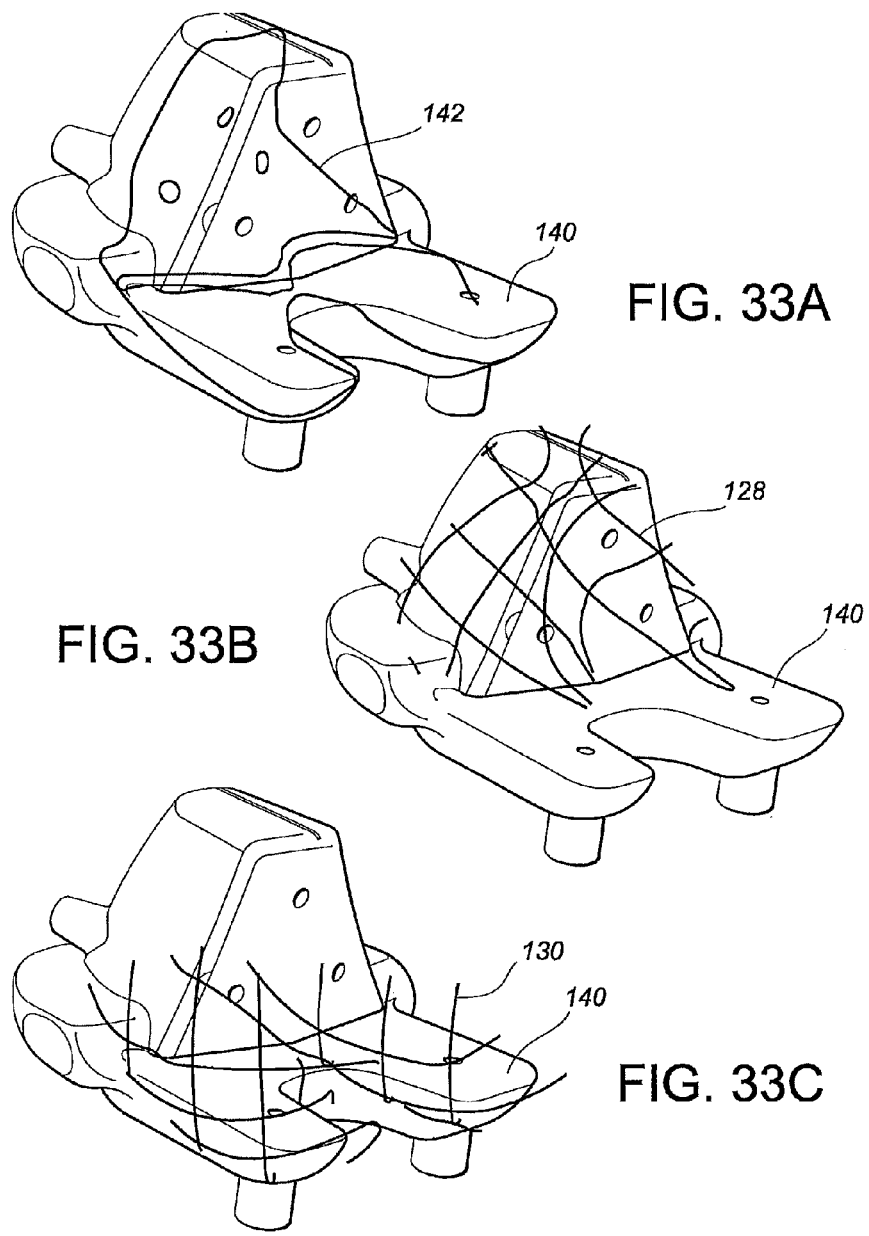

FIGS. 32A and 33A illustrate a surgical instrument blank 140 according to some embodiments. In the particular instance shown, the blank 140 is configured for use with a distal femur. The blank is generally oversized in volume so that it may be merged with a modified first anatomic model, such as the modified first anatomic model 138 shown in FIGS. 26-31. Subsequently, the volume of the modified first anatomic model 138 may be subtracted from the volume of the blank 140 to produce a patient-matched surgical instrument according to embodiments of the invention. In other embodiments, however, such as but not limited to the alternative embodiment discussed in the previous paragraph, the blank may be generally undersized such that material (or "virtual" material) is not taken away from it to create a patient-matched instrument but that material is added to it to define patient specific anatomy contacting portions on the anatomy facing face or faces of the instrument.

FIG. 32A shows a superior view of a patient-matched surgical instrument blank 140, and FIG. 33A shows a posterior isometric view of the blank 140. In both figures, a virtual intersection boundary 142 is superimposed, which represents an outer boundary of the volumetric intersection between the blank 140 and the modified first anatomic model 138 of FIG. 28.

FIGS. 32B and 33B illustrate the surgical instrument blank 140 of FIG. 32A, but instead of a virtual intersection boundary being superimposed thereon, a first mesh structure 128 is shown to be superimposed in relation to the blank 140 as it is applied to a first portion of the first anatomic model 126. In the particular instance shown, the first mesh structure 128 is an anterior mesh structure (as shown in FIG. 27A) that is applied to a portion of the first anatomic model 126 representing an anterior portion of a distal femur.

FIGS. 32C and 33C illustrate the surgical instrument blank 140 of FIG. 32A with a second mesh structure 130 superimposed in relation to the blank 140 as it is applied to a second portion of a first anatomic model 126. In the particular instance shown, the second mesh structure 130 is a distal mesh structure (as shown in FIG. 27B) that is applied to a portion of the first anatomic model 126 representing distal condylar and intercondylar portions of a distal femur.

Figure 34:
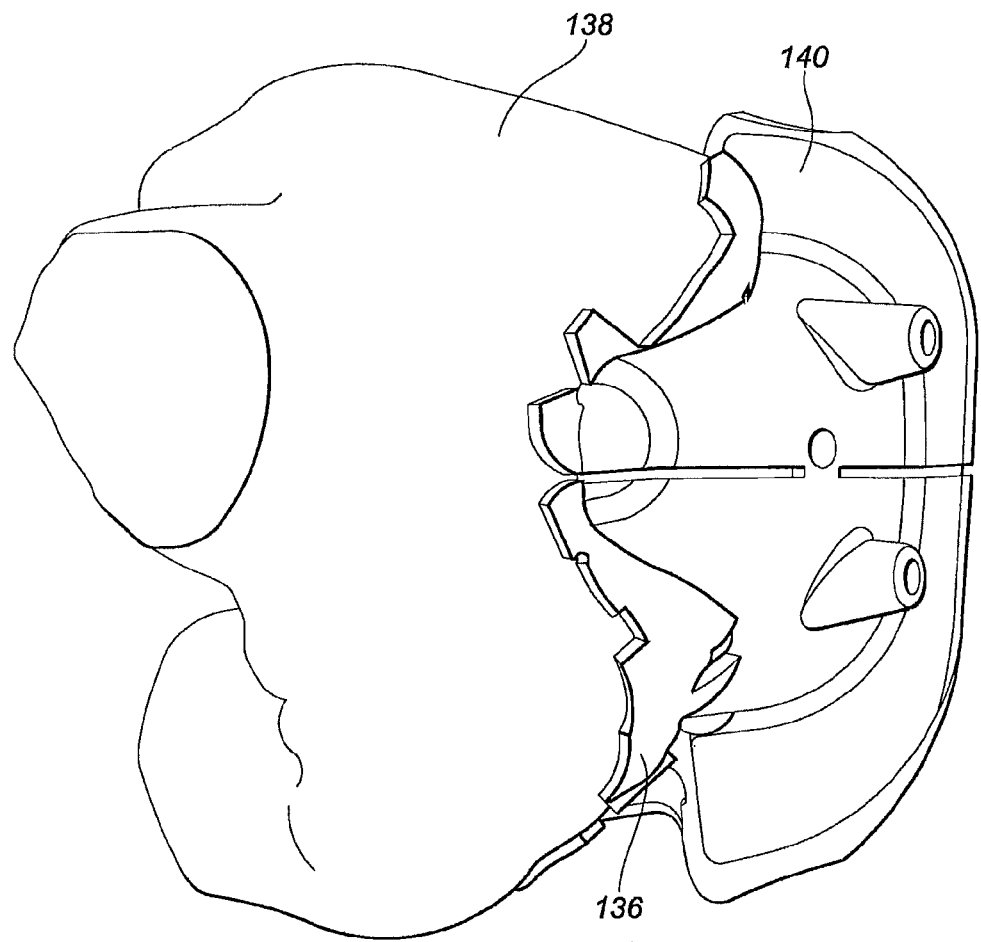
FIGS. 34 and 35 illustrate an embodiment of a method step of merging a surgical instrument blank with a modified first anatomic model, which may, in some embodiments, be followed by subtracting the modified first anatomic model from the surgical instrument blank to define a patient-matched surgical instrument.
Figure 35:
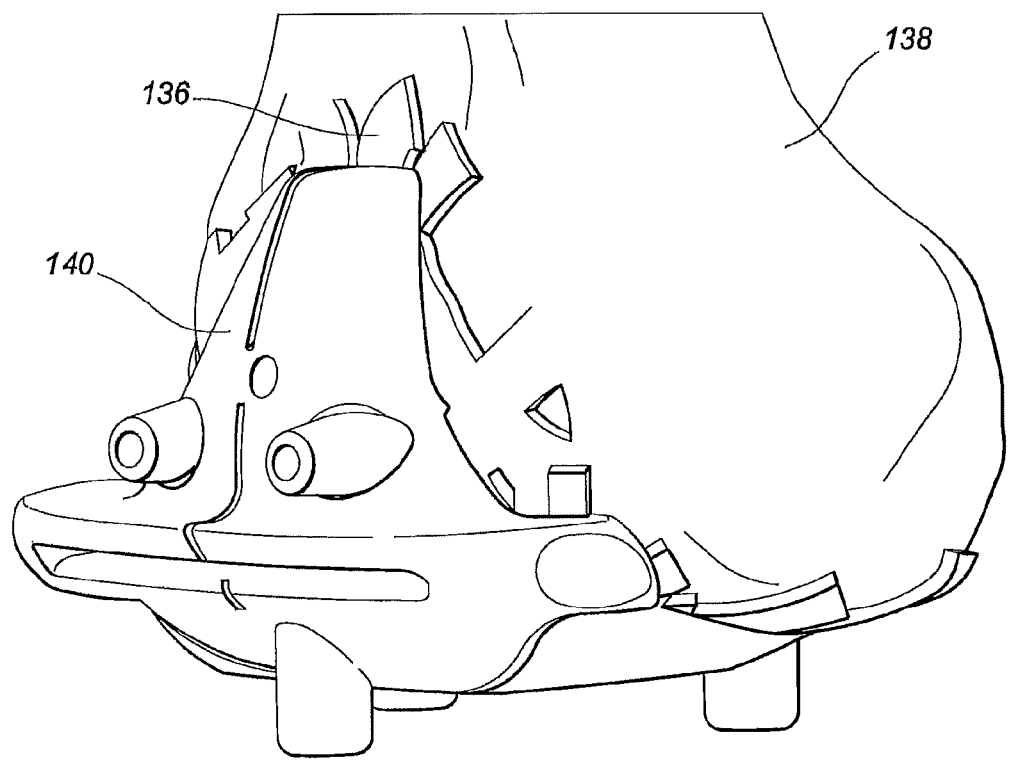

FIGS. 34 and 35 illustrate a method step of merging a surgical instrument blank 140 with a modified first anatomic model 138, and then subtracting the volume of said modified first anatomic model 138 from a volume of the surgical instrument blank 140. During the subtraction function in a CAD software package, the surgical instrument blank 140 is essentially transformed into a patient-matched surgical instrument having one or more anatomy-contacting portions as shown and described for instance in FIGS. 1 25.

Figure 36:
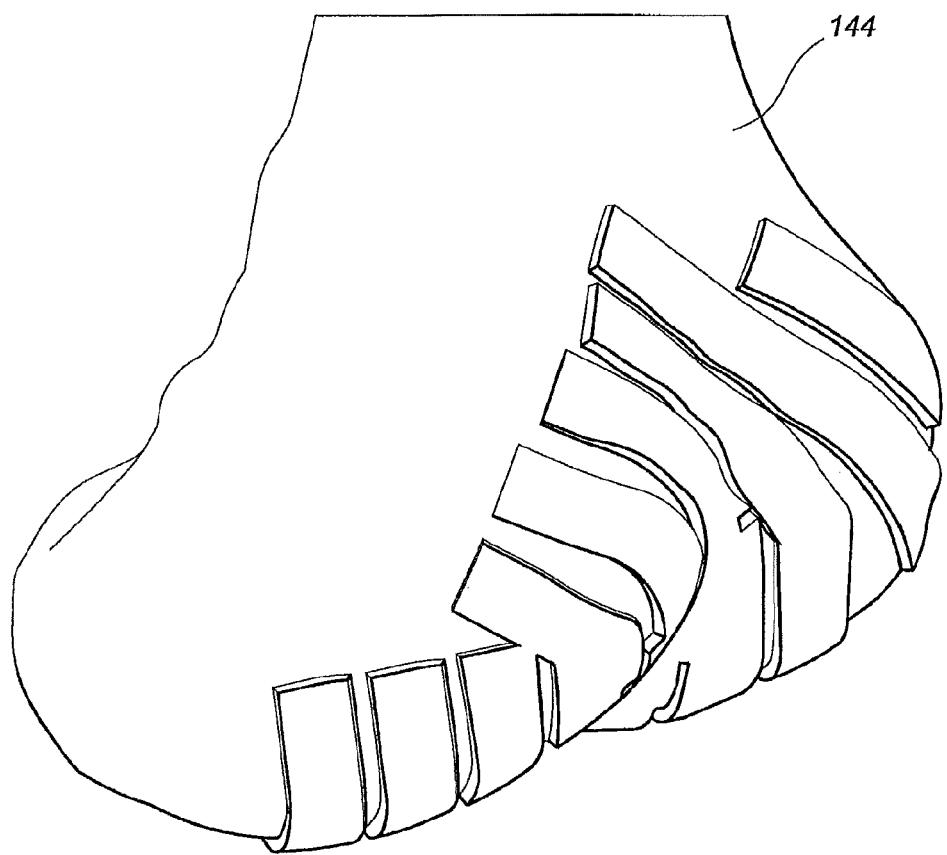
FIGS. 36-38 show another embodiment of a modified first anatomic model.
Figure 37:
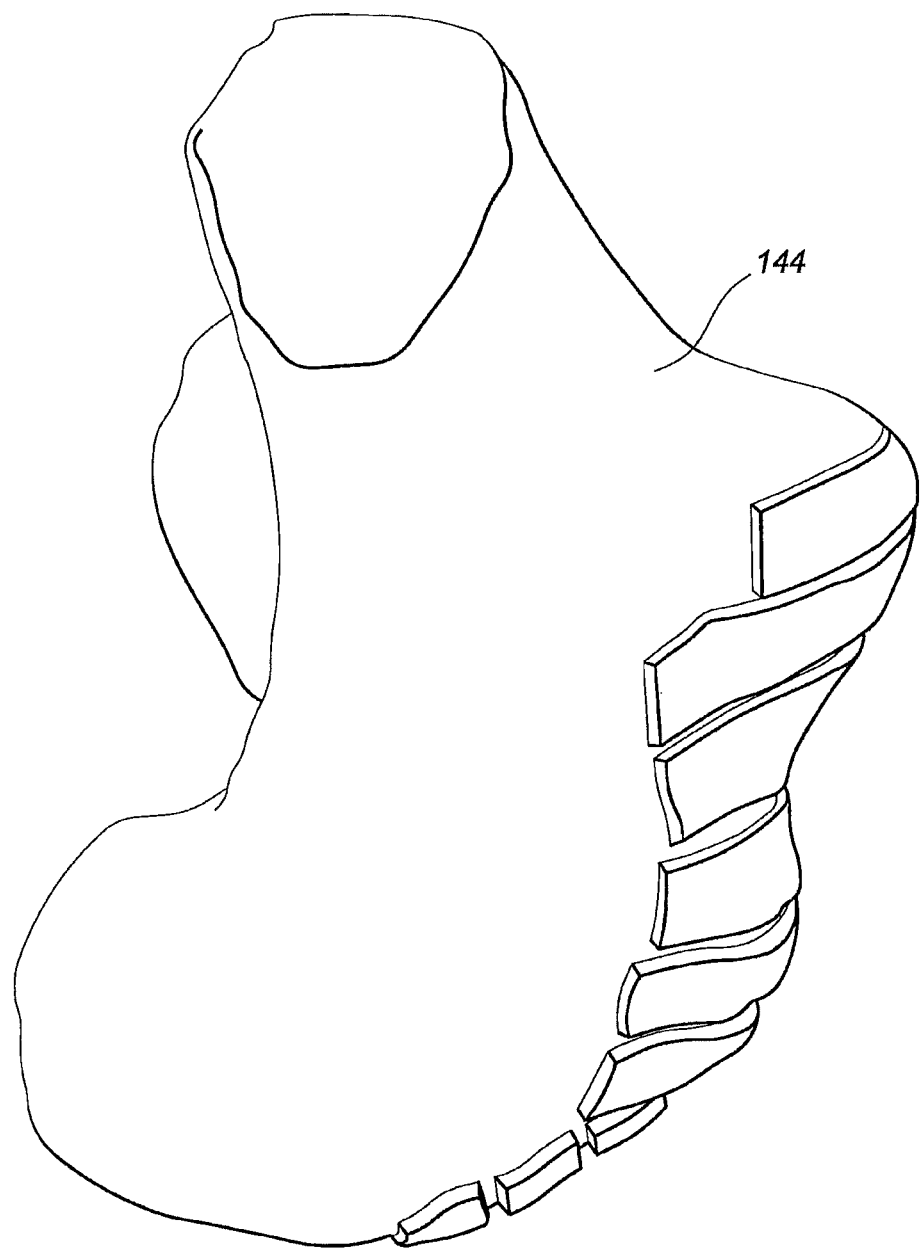
Figure 38:
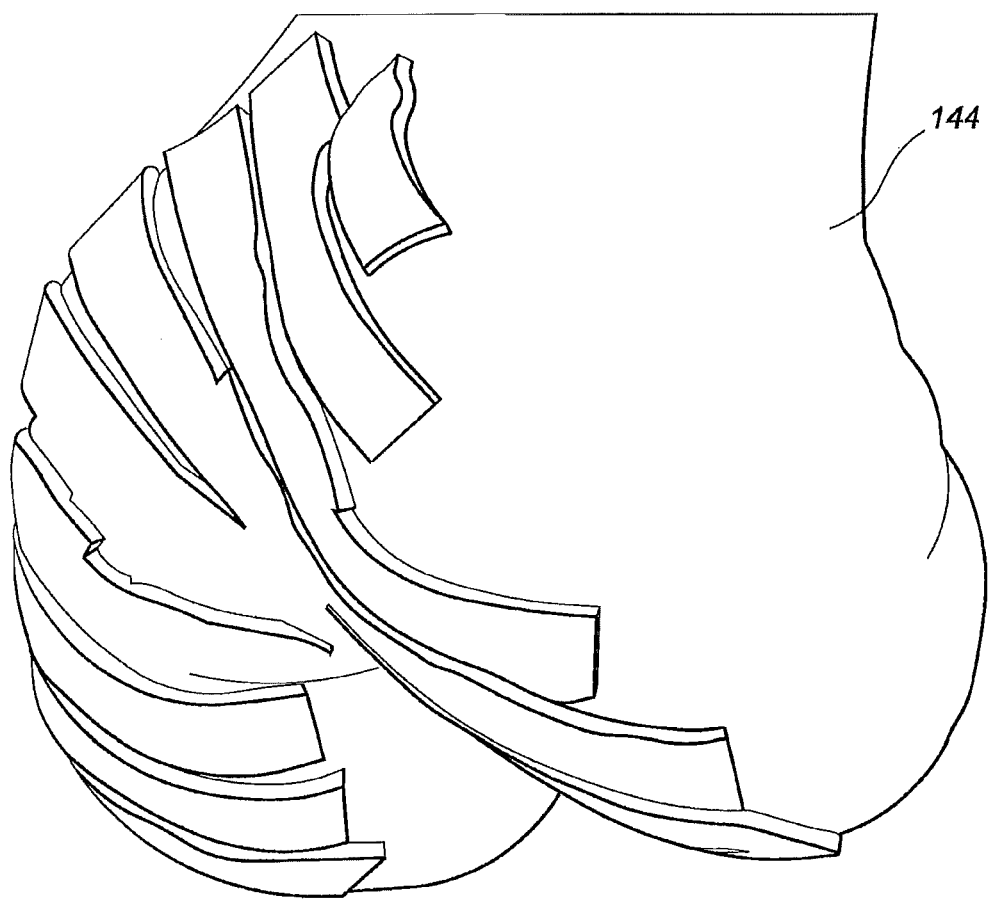

FIGS. 36-38 show an alternative embodiment of a modified first anatomic model 144, similar to that which is used to create a patient-matched surgical instrument having the anatomy contacting portions 28 shown in FIGS. 1-8.

Figure 39:
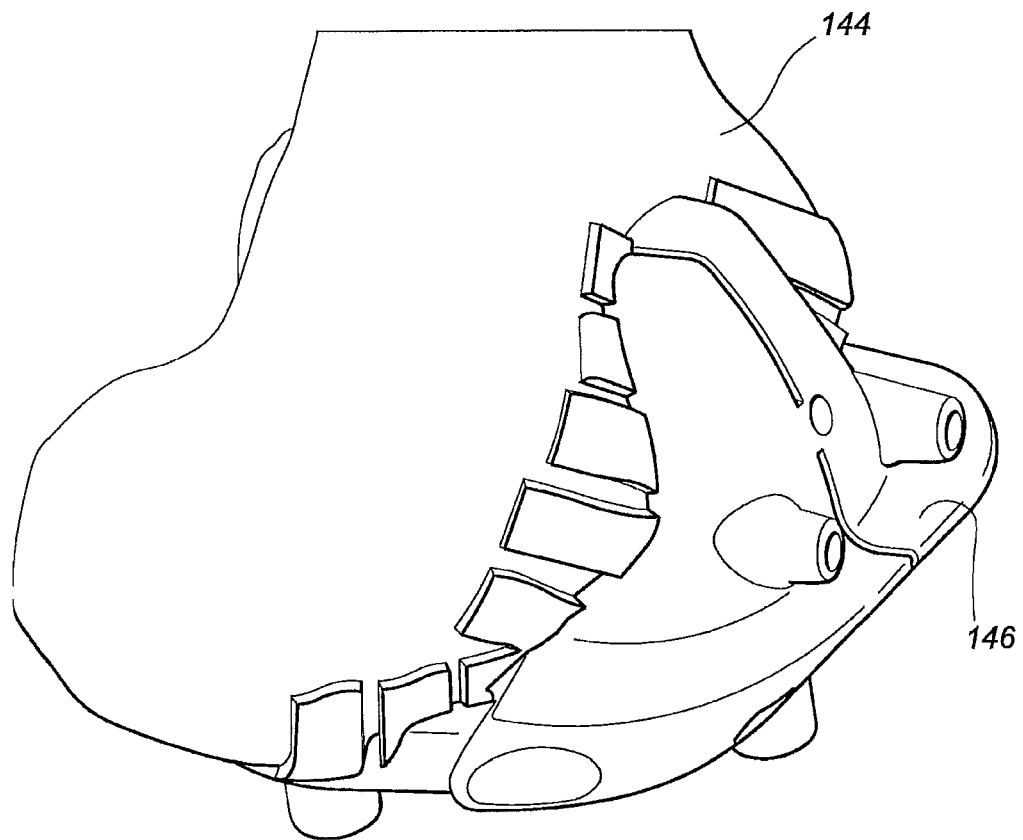
FIG. 39 illustrates an embodiment of a method step of merging a surgical instrument blank with the modified first anatomic model shown in FIGS. 36-38, and then subtracting the intersecting portions of the modified first anatomic model from the surgical instrument blank.

FIG. 39 illustrates a method step of merging a surgical instrument blank 146 with the modified first anatomic model 144 shown in FIGS. 36-38, before subtracting the volume of said modified first anatomic model 144 from the surgical instrument blank 146. After the subtraction function is executed within the CAD software package, the blank 146 is transformed into a patient-matched surgical instrument similar to the one shown in FIGS. 1-8.

Figure 40:
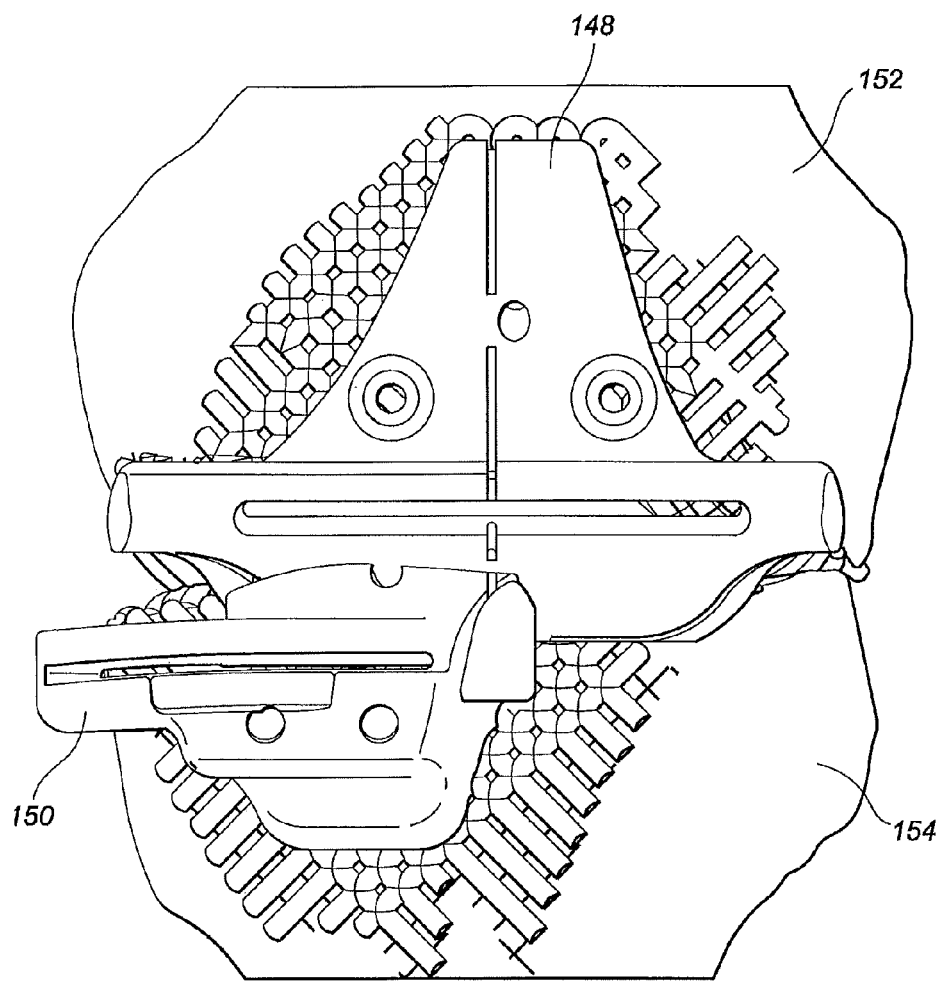
FIG. 40 illustrates an embodiment of a method step of merging first and second surgical instrument blanks with modified first and second anatomic 5 models, respectively.

FIG. 40 illustrates a method step of simultaneously merging first and second surgical instrument blanks 148 and 150 with modified first and second anatomic models 152 and 154, respectively. In the particular embodiment shown, the first modified anatomic model 152 is a distal femur model integrated with a plurality of expanded mesh structures of closely interwoven cylindrical struts or tubes, the negatives of which define the geometries and locations of patient specific pads on the surgical instrument. The second modified anatomic model 154 is a proximal tibia model integrated with a plurality of expanded mesh structures of closely interwoven cylindrical struts.

Figure 41:
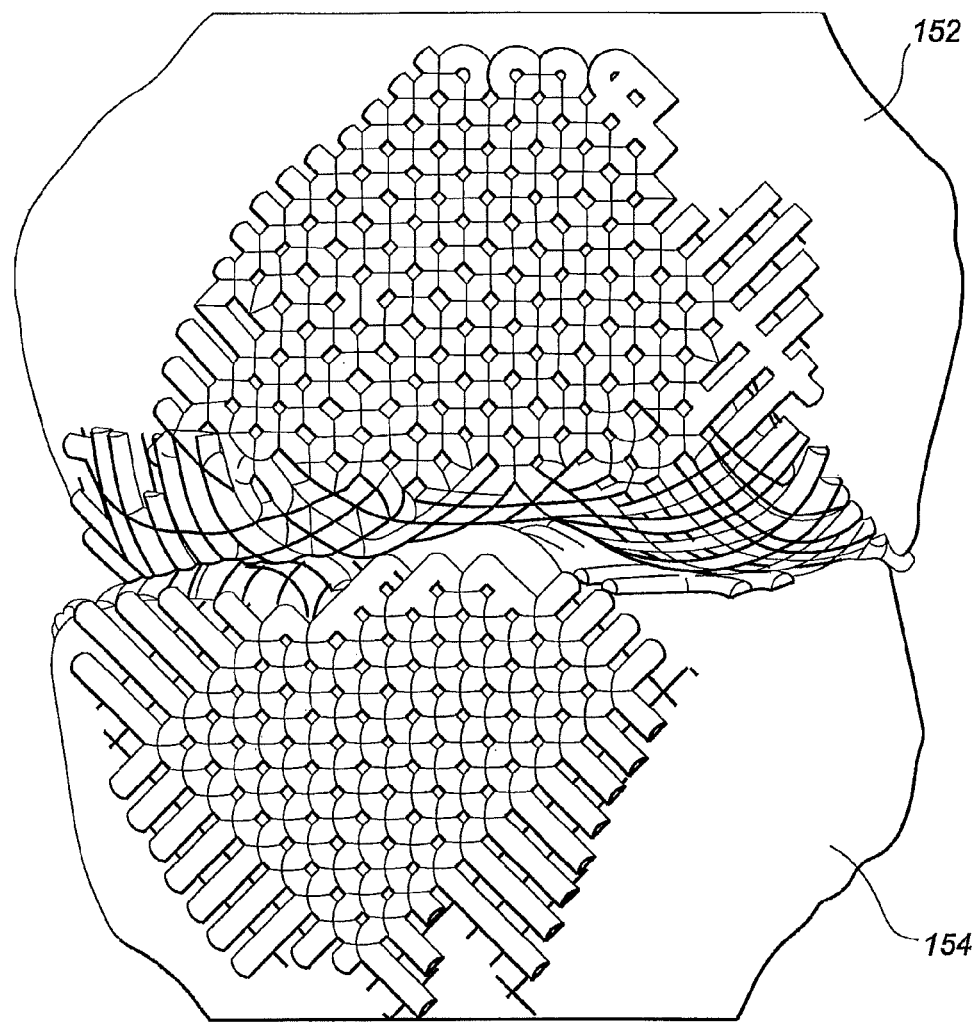
FIG. 41 illustrates an embodiment of modified first and second anatomic models, wherein one or more sweep functions are executed for mesh structures applied to first and second anatomic models.

FIG. 41 illustrates modified first and second anatomic models 152 and 154 according to the embodiment shown in FIG. 40. One or more sweep functions are executed for a plurality of mesh structures which have been applied to, projected onto, or "wrapped" over first and second anatomic models. In the particular embodiment shown, a small-radius cylinder is chosen as the cross-sectional profile to be applied to each strut within the mesh structures, a distal femur has been chosen as the first anatomic model, and a proximal tibia has been chosen as the second anatomic model. As shown in the figure, the sweep function need not be applied to an entire mesh structure and/or overlapping sections of mesh structures. Rather, it may be desirable in some instances to perform sweep functions in only select areas of the mesh structures. In some cases, such as for the embodiment shown in FIG. 17A, it may be desirable to increase the size or cross-sectional geometries of portions of the mesh structures (e.g., central areas of the mesh structures) in order to stagger, displace, or effectively remove some anatomy contacting portions 108 from desired regions of the patient-matched surgical instrument.

Figure 42A:
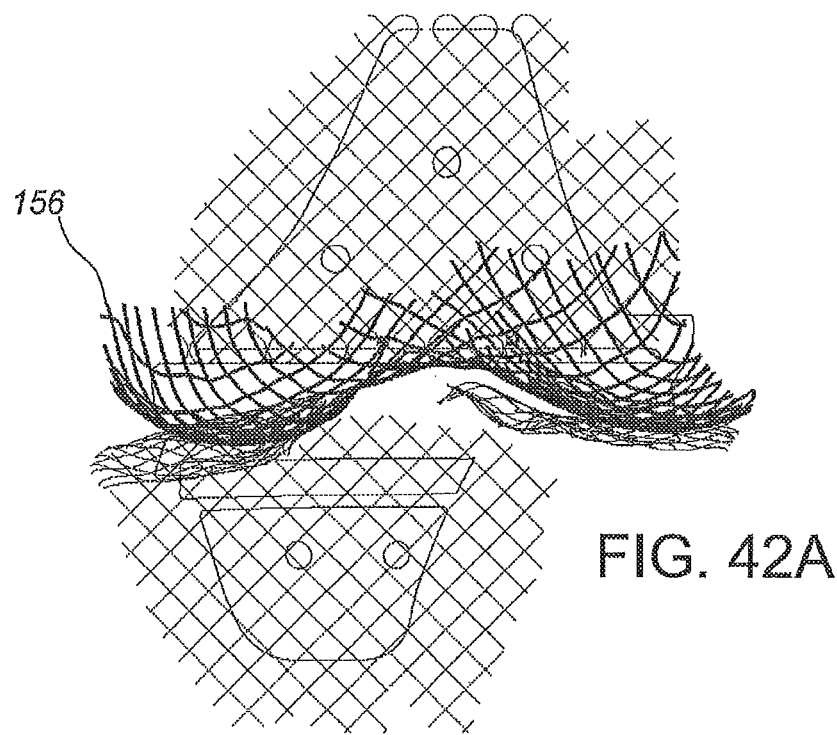
FIG. 42A illustrates a second mesh structure created and applied to a second portion of a first anatomic model according to some embodiments.

FIG. 42A illustrates a second mesh structure 156 (in bold) used to create the modified first anatomic model 152 shown in FIGS. 40 and 41. In the particular embodiment shown, the second mesh structure 156 is a distal femoral mesh structure which is applied to a distal femoral anatomic model proximate condylar and intercondylar regions.

Figure 42B:
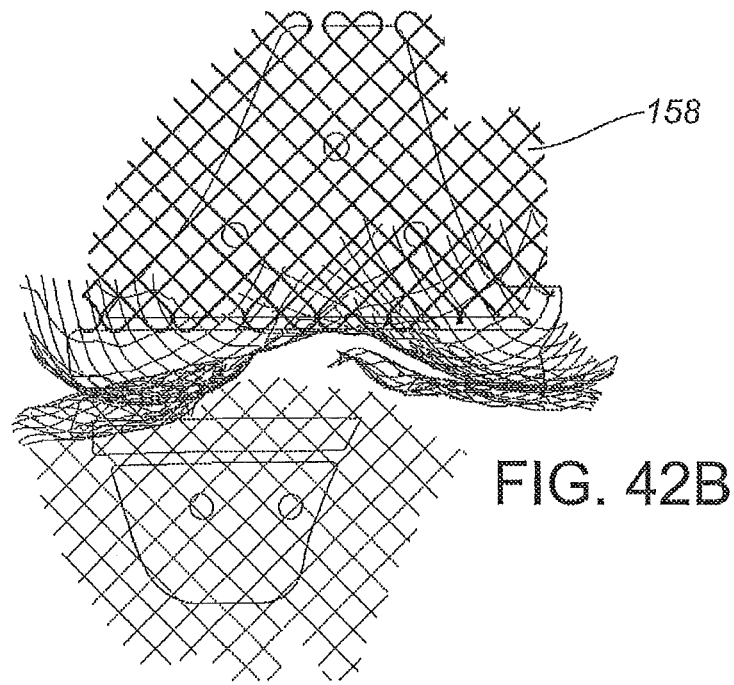
FIG. 42B illustrates a first mesh structure created and applied to a first portion of a first anatomic model according to some embodiments.

FIG. 42B illustrates a first mesh structure 158 (in bold) used to create the modified first anatomic model 152 shown in FIGS. 40 and 41. In the particular embodiment shown, the first mesh structure 158 is an anterior femoral mesh structure which is applied to an anterior portion of a distal femoral anatomic model adjacent the anterior femoral cortex and trochlear groove.

Figure 43A:
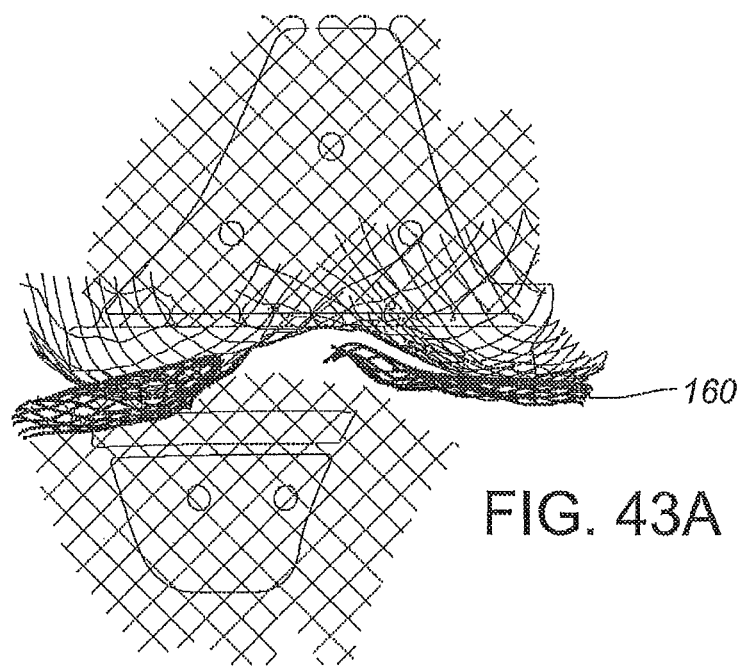
FIG. 43A illustrates a second mesh structure created and applied to a first portion of a second anatomic model according to some embodiments.

FIG. 43A illustrates a second mesh structure 160 (in bold) used to create the modified second anatomic model 154 shown in FIGS. 40 and 41. In the particular embodiment shown, the second mesh structure 160 is a proximal tibial mesh structure which is applied to a proximal tibial anatomic model proximate the medial and lateral sulcus portions of the tibial plateau.

Figure 43B:
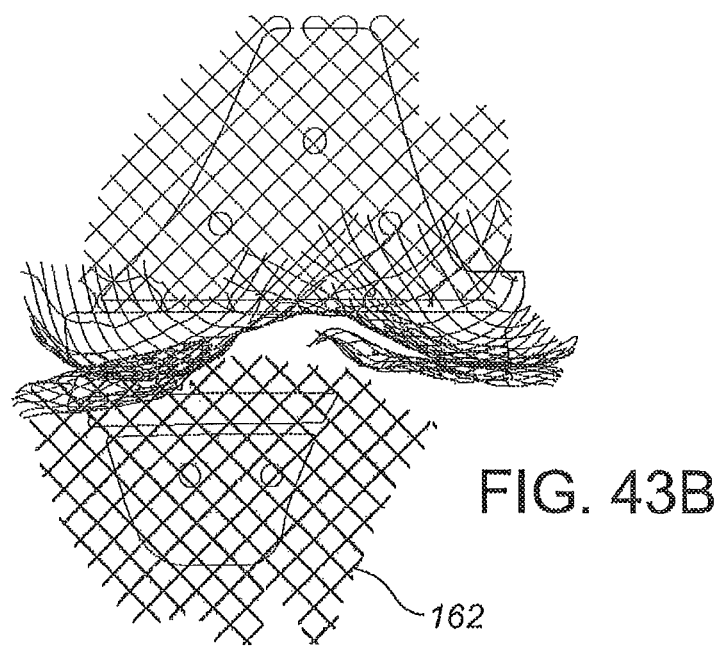
FIG. 43B illustrates a first mesh structure created and applied to a second portion of a second anatomic model according to some embodiments.

FIG. 43B illustrates a first mesh structure 162 (in bold) used to create the modified first anatomic model 154 shown in FIGS. 40 and 41. In the particular embodiment shown, the first mesh structure 162 is an anterior tibial mesh structure that is applied to an anterior cortex portion of a proximal tibial model adjacent the tibial tubercle.

Figure 44:
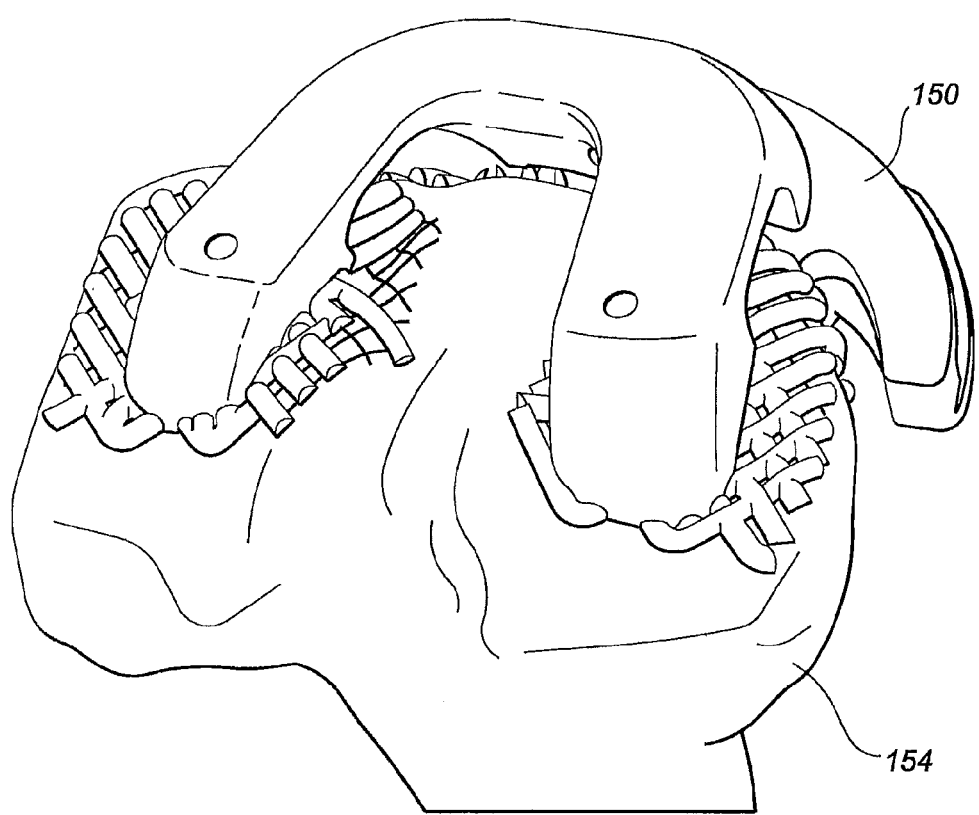
FIGS. 44 and 45 illustrate a method step of merging a second surgical instrument blank with a modified second anatomic model.
Figure 45:
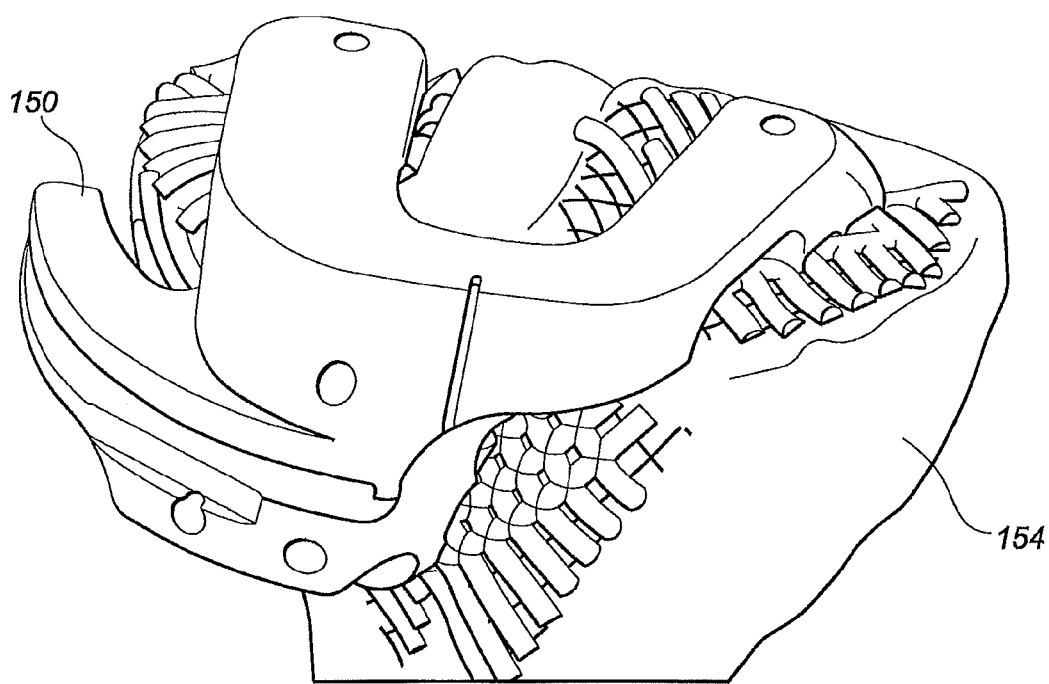

FIGS. 44 and 45 further illustrate a method step of merging a second surgical instrument blank 150 with a modified second anatomic model 154, and then subtracting a volume of said modified second anatomic model 154 from the volume of the second surgical instrument blank 150 to create a model of a patient-matched surgical instrument. In the particular embodiment shown, the patient-matched surgical instrument is a custom tibial cutting jig similar to the one shown in FIGS. 15-16. FIGS. 44 and 45 are derived from FIG. 40, showing only the modified second anatomic model 154 with the second surgical instrument blank 150 for clarity.

In some embodiments, one or more of the above described steps may be performed using computer equipment, whether stand alone or networked. Such computer equipment, in some embodiments, may include memory, a processor, and input/output features, which may facilitate performing at least some of the above identified steps, including creating one or more bone models, applying a mesh or meshes to such bone models, performing a sweep function on the mesh as applied to the bone model, merging a blank to the modified bone model, performing a subtraction function to define a patient specific instrument, and other functions. In some embodiments, the computer equipment may include or may be associated with a database in which is stored data about one or more mesh constructs, blanks, or other data. Some embodiments may include communication functionality to allow surgeons to remotely upload information about a patients' anatomy, and/or to participate or be able to provide feedback on a patient specific instrument.

While the instruments and methods shown and described are generally shown as configured for use in knee arthroplasty procedures, it is anticipated that the various anatomy-contacting portions and patterns thereof described herein may be applied to surgical instruments configured for use in other procedures. For instance, features of the described instruments and manufacturing methods thereof may be utilized with surgical instruments configured for contacting portions of a femoral head, acetabulum, glenoid, humerus, radius, ulna, fibula, tibia, proximal femur, foot, ankle, wrist, extremity, or other bony or cartilaginous regions.

As various modifications could be made to the exemplary embodiments, as described above with reference to the corresponding illustrations, without departing from the scope of the inventions described herein, it is intended that all matter contained in the foregoing description and shown in the accompanying drawings shall be interpreted as illustrative rather than limiting. Thus, the breadth and scope of the invention should not be limited by any of the above-described exemplary embodiments.

We claim:

1. A patient-matched surgical instrument matched to the anatomy of a particular patient, comprising
an anatomy facing side;
wherein the anatomy facing side includes a plurality of discrete, physically separate anatomy contacting portions, the plurality of anatomy contacting portions configured to match the anatomy of the particular patient;
wherein the anatomy facing side includes a plurality of discrete, physically separate recessed portions, wherein the plurality of recessed portions are recessed relative to parts of the anatomy contacting portions proximate the plurality of recessed portions;
wherein the plurality of anatomy contacting portions are at least one of:
non-uniform in distribution;
non-uniform in shape; and
non-uniform in surface area.

2. The patient-matched surgical instrument of claim 1, further comprising a pliant material located in at least one of the plurality of recessed portions.

3. The patient-matched surgical instrument of claim 1, wherein the plurality of anatomy contacting portions defines a first total area of the anatomy facing side and wherein the at least one recessed portion defines a second total area of the anatomy facing side;
wherein the second total area is greater than the first total area.

4. The patient-matched surgical instrument of claim 1, wherein the patient-matched surgical instrument is a femoral cutting guide,
wherein the anatomy facing side includes a patella-femoral groove portion, an intercondylar notch portion, a medial condyle portion, and a lateral condyle portion;
wherein the plurality of anatomy contacting portions comprise at least one anatomy contacting portion proximate the patella-femoral groove portion, at least one anatomy contacting portion proximate the intercondylar notch portion, at least one anatomy contacting portion proximate the medial condyle portion, and at least one anatomy contacting portion proximate the lateral condyle portion.

5. The patient-matched surgical instrument of claim 4, wherein a total area of the anatomy contacting portions proximate the patella-femoral groove portion and the intercondylar notch portion is greater than a total area of the anatomy contacting portions proximate the medial condyle portion and the lateral condyle portion.

6. The patient-matched surgical instrument of claim 4, wherein a total area of the anatomy contacting portions proximate the patella-femoral groove portion and the intercondylar notch portion is less than a total area of the anatomy contacting portions proximate the medial condyle portion and the lateral condyle portion.

7. The patient-matched surgical instrument of claim 4, wherein a density of anatomy contacting portions proximate the patella-femoral groove portion and the intercondylar notch portion is greater than a density of anatomy contacting portions proximate the medial condyle portion and the lateral condyle portion.

8. The patient-matched surgical instrument of claim 1, wherein the plurality of anatomy contacting portions comprise at least one anatomy contacting portion defining an area contact.

9. The patient-matched surgical instrument of claim 8, wherein the plurality of anatomy contacting portions further comprise at least one anatomy contacting portion defining a substantially linear contact.

10. The patient-matched surgical instrument of claim 8, wherein the plurality of anatomy contacting portions further comprise at least one anatomy contacting portion defining a substantially point contact.

11. The patient-matched surgical instrument of claim 1, wherein the anatomy facing side of the patient-matched surgical instrument includes areas of relatively greater contour and areas of relatively lower contour, wherein a concentration of the plurality of anatomy contacting portions is higher in the areas of relatively greater contour than in the areas of relatively lower contour.

12. The patient-matched surgical instrument of claim 1, wherein the anatomy facing side of the patient-matched surgical instrument includes areas of relatively greater contour and areas of relatively lower contour, wherein a concentration of the plurality of anatomy contacting portions is lower in the areas of relatively greater contour than in the areas of relatively lower contour.

13. The patient-matched surgical instrument of claim 1, wherein at least one of the plurality of anatomy contacting portions extends along a periphery of the anatomy facing side.

14. The patient-matched surgical instrument of claim 1, wherein the patient-matched surgical instrument is a tibial cutting guide comprising a medial paddle including at least one of the anatomy contacting portions and a lateral paddle including at least one of the anatomy contacting portions.

15. The patient-matched surgical instrument of claim 1, further comprising a guide extending through the patient-matched surgical instrument.

16. The patient-matched surgical instrument of claim 15, wherein the guide is a through slot including at least one planar surface.

17. A patient-matched surgical instrument matched to the anatomy of a particular patient, comprising:
an anatomy facing side;
wherein the anatomy facing side includes a plurality of discrete, physically separate and outwardly extending anatomy contacting portions, the plurality of anatomy contacting portions configured to match anatomy of the particular patient;
wherein the anatomy facing side includes a plurality of discrete, physically separate recessed portions extending between the anatomy contacting portions, wherein the plurality of recessed portions are recessed relative to parts of the anatomy contacting portions proximate the plurality of recessed portions; and
wherein the plurality of anatomy contacting portions define a first total area of the anatomy facing side and wherein the plurality of recessed portions define a second total area of the anatomy facing side; wherein the second total area is greater than the first total area.

18. The patient-matched surgical instrument of claim 17, wherein the patient-matched surgical instrument is a femoral cutting guide, wherein the anatomy facing side includes a patella-femoral groove portion, an intercondylar notch portion, a medial condyle portion, and a lateral condyle portion; wherein the plurality of anatomy contacting portions comprise at least one anatomy contacting portion proximate the patella-femoral groove portion, at least one anatomy contacting portion proximate the intercondylar notch portion, at least one anatomy contacting portion proximate the medial condyle portion, and at least one anatomy contacting portion proximate the lateral condyle portion.

19. The patient-matched surgical instrument of claim 18, wherein a total area of the anatomy contacting portions proximate the patella-femoral groove portion and the intercondylar notch portion is greater than a total area of the anatomy contacting portions proximate the medial condyle portion and the lateral condyle portion.

20. The patient-matched surgical instrument of claim 17, wherein the anatomy facing side of the patient-matched surgical instrument includes areas of relatively greater contour and areas of relatively lower contour, wherein a concentration of the plurality of anatomy contacting portions is lower in the areas of relatively greater contour than in the areas of relatively lower contour.

21. The patient-matched surgical instrument of claim 17, wherein the anatomy facing side of the patient-matched surgical instrument includes areas of relatively greater contour and areas of relatively lower contour, wherein a concentration of the plurality of anatomy contacting portions is higher in the areas of relatively greater contour than in the areas of relatively lower contour.

22. A patient-matched surgical instrument matched to the anatomy of a particular patient, comprising:
an anatomy facing side;
wherein the anatomy facing side includes a plurality of discrete, physically separate and outwardly extending anatomy contacting portions, the plurality of anatomy contacting portions configured to match the anatomy of the particular patient;
wherein the anatomy facing side includes a plurality of discrete, physically separate recessed portions, wherein the plurality of recessed portions extend between the plurality of anatomy contacting portions and are recessed relative to parts of the anatomy contacting portions proximate the plurality of recessed portions;
wherein the plurality of anatomy contacting portions are at least one of:
non-uniform in distribution;
non-uniform in shape; and
non-uniform in surface area; and
wherein the plurality of anatomy contacting portions define a first total area of the anatomy facing side and wherein the plurality of recessed portions defines a second total area of the anatomy facing side;
wherein the second total area is greater than the first total area.

* * * * *